United States Patent
Oruklu et al.

(10) Patent No.: US 10,874,793 B2
(45) Date of Patent: Dec. 29, 2020

(54) MULTI-SENSOR INFUSION SYSTEM FOR DETECTING AIR OR AN OCCLUSION IN THE INFUSION SYSTEM

(71) Applicant: ICU Medical, Inc., San Clemente, CA (US)

(72) Inventors: Meriyan Oruklu, Chicago, IL (US); Timothy L. Ruchti, Gurnee, IL (US); Paul T. Kotnik, Commerce Township, MI (US); Anatoly S. Belkin, Glenview, IL (US); Brian G. Markey, Park Forest, IL (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 16/039,637

(22) Filed: Jul. 19, 2018

(65) Prior Publication Data
US 2019/0117890 A1    Apr. 25, 2019

Related U.S. Application Data

(63) Continuation of application No. 14/285,797, filed on May 23, 2014, now Pat. No. 10,046,112.
(Continued)

(51) Int. Cl.
*A61M 5/168* (2006.01)
*A61M 5/36* (2006.01)
*A61M 5/50* (2006.01)

(52) U.S. Cl.
CPC ........ *A61M 5/16854* (2013.01); *A61M 5/365* (2013.01); *A61M 5/5086* (2013.01);
(Continued)

(58) Field of Classification Search
CPC .............. A61M 5/16854; A61M 5/365; A61M 5/5086; A61M 2005/16863;
(Continued)

(56) References Cited

U.S. PATENT DOCUMENTS

| | | |
|---|---|---|
| 3,401,337 A | 9/1968 | Beusman et al. |
| 3,484,681 A | 12/1969 | Grady, Jr. et al. |

(Continued)

FOREIGN PATENT DOCUMENTS

| | | |
|---|---|---|
| AU | 2013216679 | 9/2013 |
| BR | PI0704229-9 | 11/2009 |

(Continued)

OTHER PUBLICATIONS

Alaedeen et al., "Total Parenteral Nutrition-Associated Hyperglycemia Correlates with Prolonged Mechanical Ventilation and Hospital Stay in Septic Infants", Journal of Pediatric Surgery, Jan. 2006, vol. 41, No. 1, pp. 239-244.

(Continued)

*Primary Examiner* — Lauren P Farrar
(74) *Attorney, Agent, or Firm* — Knobbe Martens Olson & Bear, LLP

(57) ABSTRACT

An infusion system for being operatively connected to a fluid delivery line and to an infusion container includes a pump, a plurality of different types of sensors connected to the pump or the fluid delivery line, at least one processor, and a memory. The plurality of different types of sensors are configured to indicate whether air is in the fluid delivery line. The memory includes programming code for execution by the at least one processor. The programming code is configured to, based on measurements taken by the plurality of different types of sensors, determine: whether there is air in the fluid delivery line; whether there is a partial occlusion or a total occlusion in the fluid delivery line; or a percentage (Continued)

of the air present in the fluid delivery line or the probability of the air being in the fluid delivery line.

8 Claims, 13 Drawing Sheets

Related U.S. Application Data

(60) Provisional application No. 61/827,111, filed on May 24, 2013.

(52) U.S. Cl.
CPC .............. *A61M 2005/16863* (2013.01); *A61M 2005/16868* (2013.01); *A61M 2005/16872* (2013.01); *A61M 2205/18* (2013.01); *A61M 2205/332* (2013.01); *A61M 2205/3317* (2013.01); *A61M 2205/3331* (2013.01); *A61M 2205/3351* (2013.01); *A61M 2205/3355* (2013.01); *A61M 2205/3576* (2013.01); *A61M 2205/52* (2013.01)

(58) Field of Classification Search
CPC ......... A61M 2005/16868; A61M 2005/16872; A61M 2205/18; A61M 2205/3317; A61M 2205/332; A61M 2205/3331; A61M 2205/3351; A61M 2205/3355; A61M 2205/3576; A61M 2205/52
See application file for complete search history.

(56) References Cited

U.S. PATENT DOCUMENTS

| | | |
|---|---|---|
| 3,699,320 A | 10/1972 | Zimmerman et al. |
| 3,727,074 A | 4/1973 | Keller et al. |
| 3,731,679 A | 5/1973 | Wilhelmson et al. |
| 3,768,084 A | 10/1973 | Haynes |
| 3,770,354 A | 11/1973 | Tsuruta et al. |
| 3,778,702 A | 12/1973 | Finger |
| 3,806,821 A | 4/1974 | Niemeyer et al. |
| 3,838,565 A | 10/1974 | Carlyle |
| 3,854,038 A | 12/1974 | McKinley |
| 3,886,459 A | 5/1975 | Hufford et al. |
| 3,890,554 A | 6/1975 | Yoshitake et al. |
| 3,898,637 A | 8/1975 | Wolstenholme |
| 3,901,231 A | 8/1975 | Olson |
| 3,909,693 A | 9/1975 | Yoshitake et al. |
| 3,910,701 A | 10/1975 | Henderson |
| 3,911,343 A | 10/1975 | Oster |
| 3,919,608 A | 11/1975 | Usami et al. |
| 3,921,622 A | 11/1975 | Cole |
| 3,930,404 A | 1/1976 | Ryden, Jr. |
| 3,933,431 A | 1/1976 | Trujillo et al. |
| 3,935,876 A | 2/1976 | Massie et al. |
| 3,944,963 A | 3/1976 | Hively |
| 3,966,358 A | 6/1976 | Heimes et al. |
| 3,971,980 A | 7/1976 | Jungfer et al. |
| 3,974,681 A | 8/1976 | Namery |
| 3,974,683 A | 8/1976 | Martin |
| 3,985,467 A | 10/1976 | Lefferson |
| 3,990,444 A | 11/1976 | Vial |
| 3,997,888 A | 12/1976 | Kremer |
| 4,005,724 A | 2/1977 | Courtot |
| 4,014,206 A | 3/1977 | Taylor |
| 4,038,982 A | 8/1977 | Burke |
| 4,039,269 A | 8/1977 | Pickering |
| 4,048,474 A | 9/1977 | Olesen |
| 4,049,954 A | 9/1977 | Da Costa Vieira et al. |
| 4,055,175 A | 10/1977 | Clemens et al. |
| 4,068,521 A | 1/1978 | Cosentino et al. |
| 4,078,562 A | 3/1978 | Friedman |
| 4,089,227 A | 5/1978 | Falgari et al. |
| 4,094,318 A | 6/1978 | Burke |
| 4,105,028 A | 8/1978 | Sadlier et al. |
| 4,114,144 A | 9/1978 | Hyman |
| 4,151,845 A | 5/1979 | Clemens |
| 4,155,362 A | 5/1979 | Jess |
| 4,173,224 A | 11/1979 | Marx |
| 4,181,610 A | 1/1980 | Shintani et al. |
| 4,183,244 A | 1/1980 | Kohno et al. |
| 4,195,515 A | 4/1980 | Smoll |
| 4,210,138 A | 7/1980 | Jess et al. |
| 4,213,454 A | 7/1980 | Shim |
| 4,217,993 A | 8/1980 | Jess et al. |
| 4,240,294 A | 12/1980 | Grande |
| 4,240,438 A | 12/1980 | Updike et al. |
| 4,244,365 A | 1/1981 | McGill |
| 4,256,437 A | 3/1981 | Brown |
| 4,261,356 A | 4/1981 | Turner et al. |
| 4,264,861 A | 4/1981 | Radu et al. |
| 4,265,240 A | 5/1981 | Jenkins |
| 4,270,532 A | 6/1981 | Franetzki et al. |
| 4,277,226 A | 7/1981 | Archibald et al. |
| 4,278,085 A | 7/1981 | Shim |
| 4,280,495 A | 7/1981 | Lampert |
| 4,282,872 A | 8/1981 | Franetzki et al. |
| 4,286,202 A | 8/1981 | Clancy et al. |
| 4,290,346 A | 9/1981 | Bujan |
| 4,291,692 A | 9/1981 | Bowman et al. |
| 4,292,405 A | 9/1981 | Mascoli |
| 4,298,357 A | 11/1981 | Permic |
| 4,308,866 A | 1/1982 | Jeliffe |
| 4,312,341 A | 1/1982 | Zissimopoulos |
| 4,319,568 A | 3/1982 | Tregoning |
| 4,322,201 A | 3/1982 | Archibald |
| 4,323,849 A | 4/1982 | Smith |
| 4,324,662 A | 4/1982 | Schnell |
| 4,328,800 A | 5/1982 | Marx |
| 4,328,801 A | 5/1982 | Marx |
| 4,333,045 A | 6/1982 | Oltendorf |
| 4,343,316 A | 8/1982 | Jespersen |
| 4,344,429 A | 8/1982 | Gupton et al. |
| 4,346,707 A | 8/1982 | Whitney et al. |
| 4,360,019 A | 11/1982 | Portner et al. |
| 4,366,384 A | 12/1982 | Jensen |
| 4,367,736 A | 1/1983 | Gupton |
| 4,370,983 A | 2/1983 | Lichtenstein et al. |
| 4,373,527 A | 2/1983 | Fischell |
| 4,379,452 A | 4/1983 | DeVries |
| 4,381,005 A | 4/1983 | Bujan |
| 4,384,578 A | 5/1983 | Winkler |
| 4,385,247 A | 5/1983 | Satomi |
| 4,391,598 A | 7/1983 | Thompson |
| 4,392,849 A | 7/1983 | Petre et al. |
| 4,394,862 A | 7/1983 | Shim |
| 4,395,259 A | 7/1983 | Prestele et al. |
| 4,397,194 A | 8/1983 | Soltz |
| 4,399,362 A | 8/1983 | Cormier et al. |
| 4,407,659 A | 10/1983 | Adam |
| 4,411,651 A | 10/1983 | Schulman |
| 4,418,565 A | 12/1983 | St. John |
| 4,432,699 A | 2/1984 | Beckman et al. |
| 4,432,761 A | 2/1984 | Dawe |
| 4,432,762 A | 2/1984 | Dawe |
| 4,443,218 A | 4/1984 | Decant, Jr. et al. |
| 4,444,546 A | 4/1984 | Pazemenas |
| 4,447,191 A | 5/1984 | Bilstad et al. |
| 4,447,224 A | 5/1984 | Decant, Jr. et al. |
| 4,453,931 A | 6/1984 | Pastrone |
| 4,457,751 A | 7/1984 | Rodler |
| 4,463,301 A | 7/1984 | Moriguchi et al. |
| 4,464,170 A | 8/1984 | Clemens |
| 4,467,654 A | 8/1984 | Murakami et al. |
| 4,468,222 A | 8/1984 | Lundquist |
| 4,468,601 A | 8/1984 | Chamran et al. |
| 4,469,481 A | 9/1984 | Kobayashi |
| 4,475,666 A | 10/1984 | Bilbrey et al. |
| 4,475,901 A | 10/1984 | Kraegen et al. |
| 4,477,756 A | 10/1984 | Moriguchi |
| 4,479,760 A | 10/1984 | Bilstad et al. |
| 4,480,218 A | 10/1984 | Hair |
| 4,480,483 A | 11/1984 | McShane |

(56) References Cited

U.S. PATENT DOCUMENTS

| | | | |
|---|---|---|---|
| 4,483,202 | A | 11/1984 | Ogua et al. |
| 4,487,601 | A | 12/1984 | Lindemann |
| 4,492,909 | A | 1/1985 | Hartwig |
| 4,496,346 | A | 1/1985 | Mosteller |
| 4,498,843 | A | 2/1985 | Schneider et al. |
| 4,501,531 | A | 2/1985 | Bilstad et al. |
| 4,504,263 | A | 3/1985 | Steuer |
| 4,507,112 | A | 3/1985 | Hillel |
| 4,510,266 | A | 4/1985 | Eertink |
| 4,515,584 | A | 5/1985 | Abe et al. |
| 4,519,792 | A | 5/1985 | Dawe |
| 4,521,212 | A | 6/1985 | Ruschke |
| 4,525,163 | A | 6/1985 | Slavik et al. |
| 4,526,568 | A | 7/1985 | Clemens et al. |
| 4,526,574 | A | 7/1985 | Pekkarinen |
| 4,529,401 | A | 7/1985 | Leslie et al. |
| 4,533,350 | A | 8/1985 | Danby et al. |
| 4,543,955 | A | 10/1985 | Schroeppel |
| 4,551,134 | A | 11/1985 | Slavik et al. |
| 4,553,958 | A | 11/1985 | LeCocq |
| 4,559,036 | A | 12/1985 | Wunsch |
| 4,559,037 | A | 12/1985 | Franetzki et al. |
| 4,559,044 | A | 12/1985 | Robinson |
| 4,559,454 | A | 12/1985 | Kramer |
| 4,565,500 | A | 1/1986 | Jeensalaute et al. |
| 4,583,981 | A | 4/1986 | Urquhart et al. |
| 4,587,473 | A | 5/1986 | Turvey |
| 4,607,520 | A | 8/1986 | Dam |
| 4,617,014 | A | 10/1986 | Cannon et al. |
| 4,624,661 | A | 11/1986 | Arimond |
| 4,627,835 | A | 12/1986 | Fenton, Jr. |
| 4,633,878 | A | 1/1987 | Bombardieri |
| 4,634,426 | A | 1/1987 | Kamen |
| 4,634,427 | A | 1/1987 | Hannula et al. |
| 4,636,144 | A | 1/1987 | Abe et al. |
| 4,637,813 | A | 1/1987 | DeVries |
| 4,645,489 | A | 2/1987 | Krumme |
| 4,648,869 | A | 3/1987 | Bobo, Jr. |
| 4,652,260 | A | 3/1987 | Fenton, Jr. et al. |
| 4,658,244 | A | 4/1987 | Meijer |
| 4,668,216 | A | 5/1987 | Martin |
| 4,668,945 | A | 5/1987 | Aldrovandi et al. |
| 4,673,334 | A | 6/1987 | Allington et al. |
| 4,673,389 | A | 6/1987 | Archibald et al. |
| 4,676,776 | A | 6/1987 | Howson et al. |
| 4,677,359 | A | 6/1987 | Enami et al. |
| 4,678,979 | A | 7/1987 | Hori |
| 4,678,998 | A | 7/1987 | Muramatsu |
| 4,679,562 | A | 7/1987 | Luksha |
| 4,683,428 | A | 7/1987 | Gete |
| 4,685,903 | A | 8/1987 | Cable et al. |
| 4,690,673 | A | 9/1987 | Bloomquist |
| 4,691,153 | A | 9/1987 | Nishimura |
| 4,692,145 | A | 9/1987 | Weyant |
| 4,696,671 | A | 9/1987 | Epstein et al. |
| 4,697,129 | A | 9/1987 | Enami et al. |
| 4,702,675 | A | 10/1987 | Aldrovandi et al. |
| 4,705,506 | A | 11/1987 | Archibald et al. |
| 4,710,106 | A | 12/1987 | Iwata et al. |
| 4,714,462 | A | 12/1987 | DiDomenico |
| 4,714,463 | A | 12/1987 | Archibald et al. |
| 4,718,576 | A | 1/1988 | Tamura et al. |
| 4,720,636 | A | 1/1988 | Benner |
| 4,722,224 | A | 2/1988 | Scheller et al. |
| 4,722,734 | A | 2/1988 | Kolin |
| 4,731,051 | A | 3/1988 | Fischell |
| 4,731,057 | A | 3/1988 | Tanaka et al. |
| 4,737,711 | A | 4/1988 | O'Hare |
| 4,739,346 | A | 4/1988 | Buckley |
| 4,741,732 | A | 5/1988 | Crankshaw et al. |
| 4,741,736 | A | 5/1988 | Brown |
| 4,748,857 | A | 6/1988 | Nakagawa |
| 4,751,445 | A | 6/1988 | Sakai |
| 4,756,706 | A | 7/1988 | Kerns et al. |
| 4,758,228 | A | 7/1988 | Williams |
| 4,763,525 | A | 8/1988 | Cobb |
| 4,764,166 | A | 8/1988 | Spani et al. |
| 4,764,697 | A | 8/1988 | Christiaens |
| 4,776,842 | A | 10/1988 | Franetzki et al. |
| 4,781,687 | A | 11/1988 | Wall |
| 4,784,576 | A | 11/1988 | Bloom et al. |
| 4,785,184 | A | 11/1988 | Bien et al. |
| 4,785,799 | A | 11/1988 | Schoon et al. |
| 4,785,969 | A | 11/1988 | McLaughlin |
| 4,786,800 | A | 11/1988 | Kamen |
| 4,789,014 | A | 12/1988 | DiGianfilippo |
| 4,797,655 | A | 1/1989 | Orndal et al. |
| 4,803,389 | A | 2/1989 | Ogawa et al. |
| 4,803,625 | A | 2/1989 | Fu et al. |
| 4,818,186 | A | 4/1989 | Pastrone et al. |
| 4,820,281 | A | 4/1989 | Lawler |
| 4,821,558 | A | 4/1989 | Pastrone et al. |
| 4,828,545 | A | 5/1989 | Epstein et al. |
| 4,828,693 | A | 5/1989 | Lindsay |
| 4,829,448 | A | 5/1989 | Balding et al. |
| 4,838,856 | A | 6/1989 | Mulreany et al. |
| 4,838,857 | A | 6/1989 | Strowe et al. |
| 4,840,542 | A | 6/1989 | Abbott |
| 4,842,584 | A | 6/1989 | Pastrone et al. |
| 4,845,487 | A | 7/1989 | Frantz et al. |
| 4,846,792 | A | 7/1989 | Bobo et al. |
| 4,850,805 | A | 7/1989 | Madsen et al. |
| 4,851,755 | A | 7/1989 | Fincher |
| 4,854,324 | A | 8/1989 | Hirschman et al. |
| 4,856,339 | A | 8/1989 | Williams |
| 4,857,048 | A | 8/1989 | Simons et al. |
| 4,857,050 | A | 8/1989 | Lentz et al. |
| 4,858,154 | A | 8/1989 | Anderson et al. |
| 4,863,425 | A | 9/1989 | Slate et al. |
| 4,865,584 | A | 9/1989 | Epstein et al. |
| 4,869,722 | A | 9/1989 | Heyman |
| 4,874,359 | A | 10/1989 | White et al. |
| 4,881,413 | A | 11/1989 | Georgi et al. |
| 4,882,575 | A | 11/1989 | Kawahara |
| 4,884,013 | A | 11/1989 | Jackson et al. |
| 4,884,065 | A | 11/1989 | Crouse et al. |
| 4,886,422 | A | 12/1989 | Takeuchi et al. |
| 4,898,576 | A | 2/1990 | Philip |
| 4,898,578 | A | 2/1990 | Rubalcaba, Jr. |
| 4,906,103 | A | 3/1990 | Kao |
| 4,908,017 | A | 3/1990 | Howson et al. |
| 4,910,475 | A | 3/1990 | Lin |
| 4,919,595 | A | 4/1990 | Likuski et al. |
| 4,919,596 | A | 4/1990 | Slate et al. |
| 4,925,444 | A | 5/1990 | Orkin et al. |
| 4,927,411 | A | 5/1990 | Pastrone et al. |
| 4,930,358 | A | 6/1990 | Motegi et al. |
| 4,936,820 | A | 6/1990 | Dennehey |
| 4,936,828 | A | 6/1990 | Chiang |
| 4,938,079 | A | 7/1990 | Goldberg |
| 4,943,279 | A | 7/1990 | Samiotes et al. |
| 4,946,439 | A | 8/1990 | Eggers |
| 4,947,856 | A | 8/1990 | Beard |
| 4,950,235 | A | 8/1990 | Slate et al. |
| 4,950,244 | A | 8/1990 | Fellingham |
| 4,959,050 | A | 9/1990 | Bobo, Jr. |
| 4,966,579 | A | 10/1990 | Polaschegg |
| 4,968,941 | A | 11/1990 | Rogers |
| 4,972,842 | A | 11/1990 | Korten et al. |
| 4,976,687 | A | 12/1990 | Martin |
| 4,978,335 | A | 12/1990 | Arthur, III |
| 4,979,940 | A | 12/1990 | Lapp et al. |
| 4,981,467 | A | 1/1991 | Bobo et al. |
| 5,000,663 | A | 3/1991 | Gorton |
| 5,000,739 | A | 3/1991 | Kulisz et al. |
| 5,006,050 | A | 4/1991 | Cooke et al. |
| 5,010,473 | A | 4/1991 | Jacobs |
| 5,014,714 | A | 5/1991 | Millay et al. |
| 5,018,945 | A | 5/1991 | D'Silva |
| 5,026,348 | A | 6/1991 | Venegas |
| 5,028,857 | A | 7/1991 | Taghezout |
| 5,032,112 | A | 7/1991 | Fairchild et al. |
| 5,034,004 | A | 7/1991 | Crankshaw |
| 5,035,143 | A | 7/1991 | Latimer et al. |

(56) References Cited

U.S. PATENT DOCUMENTS

| | | |
|---|---|---|
| 5,041,086 A | 8/1991 | Koenig et al. |
| 5,043,706 A | 8/1991 | Oliver |
| 5,045,069 A | 9/1991 | Imparato |
| 5,049,047 A | 9/1991 | Polaschegg et al. |
| 5,052,230 A | 10/1991 | Lang |
| 5,053,747 A | 10/1991 | Slate et al. |
| 5,055,761 A | 10/1991 | Mills |
| 5,056,992 A | 10/1991 | Simons |
| 5,058,161 A | 10/1991 | Weiss |
| 5,059,171 A | 10/1991 | Bridge |
| 5,063,603 A | 11/1991 | Burt |
| 5,064,412 A | 11/1991 | Henke et al. |
| 5,078,683 A | 1/1992 | Sancoff et al. |
| 5,084,663 A | 1/1992 | Olsson |
| 5,084,828 A | 1/1992 | Kaufman et al. |
| 5,088,981 A | 2/1992 | Howson et al. |
| 5,096,385 A | 3/1992 | Georgi et al. |
| 5,097,505 A | 3/1992 | Weiss |
| 5,100,380 A | 3/1992 | Epstein et al. |
| 5,102,392 A | 4/1992 | Sakai et al. |
| 5,103,211 A | 4/1992 | Daoud et al. |
| 5,104,374 A | 4/1992 | Bishko et al. |
| 5,108,367 A | 4/1992 | Epstein et al. |
| 5,109,850 A | 5/1992 | Blanco et al. |
| 5,116,203 A | 5/1992 | Nartwick et al. |
| 5,116,312 A | 5/1992 | Blakenship et al. |
| 5,116,316 A | 5/1992 | Sertic |
| 5,123,275 A | 6/1992 | Daoud et al. |
| 5,124,627 A | 6/1992 | Okada |
| 5,125,499 A | 6/1992 | Saathoff et al. |
| 5,131,816 A | 7/1992 | Brown |
| 5,132,603 A | 7/1992 | Yoshimoto |
| 5,153,827 A | 10/1992 | Coutre et al. |
| 5,158,441 A | 10/1992 | Aid |
| 5,161,222 A | 11/1992 | Montejo et al. |
| 5,174,472 A | 12/1992 | Raque et al. |
| 5,176,631 A | 1/1993 | Koenig |
| 5,176,646 A | 1/1993 | Kuroda |
| 5,179,340 A | 1/1993 | Rogers |
| 5,180,287 A * | 1/1993 | Natwick ............... A61M 5/142 417/43 |
| 5,181,910 A | 1/1993 | Scanlon |
| 5,186,057 A | 2/1993 | Everhart |
| 5,188,603 A | 2/1993 | Vaillancourt |
| 5,190,522 A | 3/1993 | Wocicki et al. |
| 5,191,795 A | 3/1993 | Fellingham et al. |
| 5,192,340 A | 3/1993 | Grant et al. |
| 5,194,796 A | 3/1993 | Domeki et al. |
| 5,198,776 A | 3/1993 | Carr |
| 5,200,090 A | 4/1993 | Ford |
| 5,205,819 A | 4/1993 | Ross et al. |
| 5,206,522 A | 4/1993 | Danby et al. |
| 5,207,642 A | 5/1993 | Orkin et al. |
| 5,211,626 A | 5/1993 | Frank et al. |
| 5,213,573 A | 5/1993 | Sorich et al. |
| 5,215,450 A | 6/1993 | Tamari |
| 5,216,597 A | 6/1993 | Beckers |
| 5,219,099 A | 6/1993 | Spence et al. |
| 5,219,327 A | 6/1993 | Okada |
| 5,221,268 A | 6/1993 | Barton et al. |
| 5,229,713 A | 7/1993 | Bullock et al. |
| 5,232,476 A | 8/1993 | Grant |
| 5,233,571 A | 8/1993 | Wirtschafter |
| 5,237,309 A | 8/1993 | Frantz et al. |
| 5,242,406 A | 9/1993 | Gross et al. |
| 5,242,408 A | 9/1993 | Jhuboo et al. |
| 5,243,982 A | 9/1993 | Möstl et al. |
| 5,244,463 A | 9/1993 | Cordner, Jr. et al. |
| 5,244,568 A | 9/1993 | Lindsay et al. |
| 5,254,096 A | 10/1993 | Rondelet et al. |
| 5,256,155 A | 10/1993 | Yerlikaya et al. |
| 5,256,156 A | 10/1993 | Kern et al. |
| 5,256,157 A | 10/1993 | Samiotes et al. |
| 5,260,665 A | 11/1993 | Goldberg |
| 5,257,206 A | 12/1993 | Hanson |
| 5,267,980 A | 12/1993 | Dirr et al. |
| 5,274,316 A | 12/1993 | Evans et al. |
| 5,276,610 A | 1/1994 | Maeda et al. |
| 5,280,728 A | 1/1994 | Sato et al. |
| 5,283,510 A | 2/1994 | Tamaki et al. |
| 5,287,851 A | 2/1994 | Beran et al. |
| 5,292,306 A | 3/1994 | Wynkoop et al. |
| 5,295,967 A | 3/1994 | Rondelet et al. |
| 5,298,021 A | 3/1994 | Sherer |
| 5,303,585 A | 4/1994 | Lichte |
| 5,304,126 A | 4/1994 | Epstein et al. |
| 5,308,333 A | 5/1994 | Skakoon |
| 5,317,506 A | 5/1994 | Coutre et al. |
| 5,319,363 A | 6/1994 | Welch et al. |
| 5,319,979 A | 6/1994 | Abrahamson |
| 5,321,392 A | 6/1994 | Skakoon et al. |
| 5,325,170 A | 6/1994 | Bornhop |
| 5,325,728 A | 7/1994 | Zimmerman et al. |
| 5,328,460 A | 7/1994 | Lord et al. |
| 5,330,634 A | 7/1994 | Wong et al. |
| 5,333,497 A | 8/1994 | Braend et al. |
| 5,336,051 A | 8/1994 | Tamari |
| 5,338,157 A | 8/1994 | Blomquist |
| 5,342,298 A | 8/1994 | Michaels |
| 5,343,734 A | 9/1994 | Maeda et al. |
| 5,343,885 A | 9/1994 | Grant |
| 5,346,466 A | 9/1994 | Yerlikaya et al. |
| 5,356,378 A | 10/1994 | Doan et al. |
| 5,359,271 A | 10/1994 | Husher |
| D352,778 S | 11/1994 | Irvin et al. |
| 5,364,346 A | 11/1994 | Schrezenmeir |
| 5,366,346 A | 11/1994 | Danby |
| 5,368,562 A | 11/1994 | Blomquist et al. |
| 5,374,865 A | 12/1994 | Yoshimura et al. |
| 5,376,070 A | 12/1994 | Purvis et al. |
| 5,378,231 A | 1/1995 | Johnson et al. |
| 5,382,232 A | 1/1995 | Hague et al. |
| 5,383,369 A | 1/1995 | Khuri-Yakub et al. |
| 5,389,071 A | 2/1995 | Kawahara et al. |
| 5,389,078 A | 2/1995 | Zalesky et al. |
| 5,392,638 A | 2/1995 | Kawahara |
| 5,394,732 A | 3/1995 | Johnson et al. |
| 5,395,320 A | 3/1995 | Padda et al. |
| 5,399,171 A | 3/1995 | Bowman et al. |
| 5,406,954 A | 4/1995 | Tomita |
| 5,408,326 A | 4/1995 | Priestley |
| 5,415,528 A | 5/1995 | Ogden et al. |
| 5,417,119 A | 5/1995 | Smoll |
| 5,417,222 A | 5/1995 | Dempsey et al. |
| 5,417,395 A | 5/1995 | Fowler et al. |
| 5,418,443 A | 5/1995 | Kikuchi |
| 5,421,208 A | 6/1995 | Packard et al. |
| 5,423,748 A | 6/1995 | Uhala |
| 5,423,759 A | 6/1995 | Campbell |
| 5,428,284 A | 6/1995 | Kaneda et al. |
| 5,429,485 A | 7/1995 | Dodge |
| 5,429,601 A | 7/1995 | Conley |
| 5,429,602 A | 7/1995 | Hauser |
| 5,431,627 A | 7/1995 | Pastrone et al. |
| 5,434,508 A | 7/1995 | Ishida |
| 5,437,624 A | 8/1995 | Langley et al. |
| 5,444,316 A | 8/1995 | Ohya et al. |
| 5,444,378 A | 8/1995 | Rogers |
| 5,445,621 A | 8/1995 | Poli et al. |
| 5,450,758 A | 9/1995 | Smoll |
| 5,451,881 A | 9/1995 | Finger |
| 5,455,423 A | 10/1995 | Mount et al. |
| 5,455,851 A | 10/1995 | Chaco et al. |
| 5,463,906 A | 11/1995 | Spani et al. |
| 5,464,392 A | 11/1995 | Epstein et al. |
| 5,465,082 A | 11/1995 | Chaco |
| 5,469,851 A | 11/1995 | Lipschutz |
| 5,473,948 A | 12/1995 | Moss et al. |
| 5,480,294 A | 1/1996 | Di Perna et al. |
| 5,482,438 A | 1/1996 | Anderson et al. |
| 5,485,408 A | 1/1996 | Blomquist |
| 5,486,286 A | 1/1996 | Peterson et al. |
| 5,489,265 A | 2/1996 | Montalvo et al. |
| 5,495,566 A | 2/1996 | Kwatinetz |

(56) References Cited

U.S. PATENT DOCUMENTS

| | | |
|---|---|---|
| 5,496,273 A | 3/1996 | Pastrone et al. |
| 5,505,696 A | 4/1996 | Miki |
| 5,505,828 A | 4/1996 | Wong et al. |
| 5,507,288 A | 4/1996 | Bocker et al. |
| 5,507,412 A | 4/1996 | Ebert et al. |
| 5,520,637 A | 5/1996 | Pager et al. |
| 5,522,798 A | 6/1996 | Johnson et al. |
| 5,522,799 A | 6/1996 | Furukawa |
| 5,527,630 A | 6/1996 | Nagata |
| 5,533,389 A | 7/1996 | Kamen et al. |
| 5,537,853 A | 7/1996 | Finburgh et al. |
| 5,542,040 A | 7/1996 | Chang et al. |
| 5,545,140 A | 8/1996 | Conero et al. |
| 5,547,470 A | 8/1996 | Johnson et al. |
| 5,551,850 A | 9/1996 | Williamson et al. |
| 5,554,013 A | 9/1996 | Owens et al. |
| 5,554,115 A | 9/1996 | Thomas et al. |
| 5,558,638 A | 9/1996 | Evers et al. |
| 5,562,615 A | 10/1996 | Nassif |
| 5,563,486 A | 10/1996 | Yamamoto et al. |
| 5,572,105 A | 11/1996 | Nojima et al. |
| 5,573,502 A | 11/1996 | LeCocq et al. |
| 5,583,280 A | 12/1996 | Mo et al. |
| 5,584,667 A | 12/1996 | Davis |
| 5,584,806 A | 12/1996 | Amano |
| 5,586,868 A | 12/1996 | Lawless et al. |
| 5,590,653 A | 1/1997 | Aida et al. |
| 5,594,786 A | 1/1997 | Chaco et al. |
| 5,600,073 A | 2/1997 | Hill |
| 5,601,420 A | 2/1997 | Warner et al. |
| 5,609,575 A | 3/1997 | Larson et al. |
| 5,609,576 A | 3/1997 | Voss |
| 5,611,784 A | 3/1997 | Barresi et al. |
| 5,616,124 A | 4/1997 | Hague et al. |
| 5,620,312 A | 4/1997 | Hyman et al. |
| 5,620,608 A | 4/1997 | Rosa et al. |
| 5,626,140 A | 5/1997 | Feldman et al. |
| 5,626,151 A | 5/1997 | Linden |
| 5,626,563 A | 5/1997 | Dodge et al. |
| 5,627,443 A | 5/1997 | Kimura et al. |
| 5,628,309 A | 5/1997 | Brown |
| 5,628,731 A | 5/1997 | Dodge et al. |
| 5,630,710 A | 5/1997 | Tune et al. |
| 5,634,896 A | 6/1997 | Bryant et al. |
| 5,637,095 A | 6/1997 | Nason et al. |
| 5,640,075 A | 6/1997 | Brasseur et al. |
| 5,640,150 A | 6/1997 | Atwater |
| 5,643,212 A | 7/1997 | Coutre et al. |
| 5,648,710 A | 7/1997 | Ikeda |
| 5,649,536 A | 7/1997 | Ogura et al. |
| 5,651,775 A | 7/1997 | Walker et al. |
| 5,657,000 A | 8/1997 | Ellingboe |
| 5,658,133 A | 8/1997 | Anderson et al. |
| 5,658,250 A | 8/1997 | Blomquist et al. |
| 5,659,234 A | 8/1997 | Cresens |
| 5,661,245 A | 8/1997 | Svoboda et al. |
| 5,662,612 A | 9/1997 | Niehoff |
| 5,665,065 A | 9/1997 | Colman et al. |
| 5,669,877 A | 9/1997 | Blomquist |
| 5,672,154 A | 9/1997 | Sillén et al. |
| 5,672,832 A | 9/1997 | Cucci et al. |
| 5,681,285 A | 10/1997 | Ford et al. |
| 5,681,286 A | 10/1997 | Niehoff |
| 5,685,844 A | 11/1997 | Marttila |
| 5,687,717 A | 11/1997 | Halpern et al. |
| 5,689,229 A | 11/1997 | Chaco et al. |
| 5,691,613 A | 11/1997 | Gutwillinger |
| 5,695,464 A | 12/1997 | Viallet |
| 5,695,473 A | 12/1997 | Olsen |
| 5,697,899 A | 12/1997 | Hillman et al. |
| 5,697,916 A | 12/1997 | Schraga |
| 5,712,795 A | 1/1998 | Layman et al. |
| 5,713,856 A | 2/1998 | Eggers et al. |
| 5,714,691 A | 2/1998 | Hill |
| 5,718,562 A | 2/1998 | Lawless et al. |
| 5,718,569 A | 2/1998 | Holst |
| 5,720,721 A | 2/1998 | Dumas et al. |
| 5,722,417 A | 3/1998 | Rudolph |
| 5,728,074 A | 3/1998 | Castellano et al. |
| 5,728,948 A | 3/1998 | Bignell et al. |
| 5,733,257 A | 3/1998 | Stemby |
| 5,733,259 A | 3/1998 | Valcke et al. |
| 5,738,659 A | 4/1998 | Neer et al. |
| 5,743,856 A | 4/1998 | Oka et al. |
| 5,744,027 A | 4/1998 | Connell et al. |
| 5,744,929 A | 4/1998 | Miyazaki |
| 5,745,378 A | 4/1998 | Barker et al. |
| 5,752,813 A | 5/1998 | Tyner et al. |
| 5,752,918 A | 5/1998 | Fowler et al. |
| 5,752,919 A | 5/1998 | Schrimpf |
| 5,755,691 A | 5/1998 | Hilborne |
| 5,758,643 A | 6/1998 | Wong et al. |
| 5,761,072 A | 6/1998 | Bardsley, Jr. et al. |
| 5,764,034 A | 6/1998 | Bowman et al. |
| 5,766,155 A | 6/1998 | Hyman et al. |
| 5,772,635 A | 6/1998 | Dastur et al. |
| 5,778,256 A | 7/1998 | Darbee |
| 5,781,442 A | 7/1998 | Engleson et al. |
| 5,782,805 A | 7/1998 | Meinzer et al. |
| 5,788,669 A | 8/1998 | Peterson |
| 5,788,674 A | 8/1998 | McWilliams |
| 5,789,923 A | 8/1998 | Shimoyama et al. |
| 5,792,069 A | 8/1998 | Greenwald et al. |
| 5,793,211 A | 8/1998 | Shimoyama et al. |
| 5,795,327 A | 8/1998 | Wilson et al. |
| 5,798,934 A | 8/1998 | Saigo et al. |
| 5,800,387 A * | 9/1998 | Duffy .................. A61M 5/142 604/65 |
| 5,803,712 A | 9/1998 | Davis et al. |
| 5,803,917 A | 9/1998 | Butterfield |
| 5,805,455 A | 9/1998 | Lipps |
| 5,807,322 A | 9/1998 | Lindsey et al. |
| 5,810,770 A | 9/1998 | Chin et al. |
| 5,813,972 A | 9/1998 | Nazarian et al. |
| 5,814,004 A | 9/1998 | Tamari |
| 5,814,015 A | 9/1998 | Gargano et al. |
| 5,816,779 A | 10/1998 | Lawless et al. |
| 5,822,715 A | 10/1998 | Worthington et al. |
| 5,827,179 A | 10/1998 | Lichter et al. |
| 5,827,223 A | 10/1998 | Butterfield |
| 5,832,448 A | 11/1998 | Brown |
| 5,836,910 A | 11/1998 | Duffy et al. |
| 5,841,261 A | 11/1998 | Nojima et al. |
| 5,841,284 A | 11/1998 | Takahashi |
| 5,843,035 A | 12/1998 | Bowman |
| 5,848,971 A | 12/1998 | Fowler et al. |
| 5,850,344 A | 12/1998 | Conkright |
| 5,857,843 A | 1/1999 | Leason et al. |
| 5,864,330 A | 1/1999 | Haynes |
| 5,865,805 A | 2/1999 | Ziemba |
| 5,867,821 A | 2/1999 | Ballantyne et al. |
| 5,871,465 A | 2/1999 | Vasko |
| 5,872,453 A | 2/1999 | Shimoyama et al. |
| 5,875,195 A | 2/1999 | Dixon |
| 5,882,300 A | 3/1999 | Malinouskas et al. |
| 5,882,339 A | 3/1999 | Beiser et al. |
| 5,885,245 A | 3/1999 | Lynch et al. |
| 5,889,379 A | 3/1999 | Yanagi et al. |
| 5,891,051 A | 4/1999 | Han et al. |
| 5,894,209 A | 4/1999 | Takagi et al. |
| 5,897,493 A | 4/1999 | Brown |
| 5,897,498 A | 4/1999 | Canfield, II et al. |
| 5,898,292 A | 4/1999 | Takemoto et al. |
| 5,899,665 A | 5/1999 | Makino et al. |
| 5,901,150 A | 5/1999 | Jhuboo et al. |
| 5,904,666 A | 5/1999 | DeDecker et al. |
| 5,904,668 A | 5/1999 | Hyman et al. |
| 5,905,207 A | 5/1999 | Schalk |
| 5,906,598 A | 5/1999 | Giesler |
| 5,910,252 A | 6/1999 | Truitt et al. |
| 5,915,240 A | 6/1999 | Karpf |
| 5,920,263 A | 7/1999 | Huttenhoff et al. |
| 5,923,159 A | 7/1999 | Ezell |
| 5,924,074 A | 7/1999 | Evans |

(56) References Cited

U.S. PATENT DOCUMENTS

| | | |
|---|---|---|
| 5,927,349 A | 7/1999 | Martucci |
| 5,932,119 A | 8/1999 | Kaplan et al. |
| 5,932,987 A | 8/1999 | McLoughlin |
| 5,935,099 A | 8/1999 | Peterson et al. |
| 5,935,106 A | 8/1999 | Olsen |
| 5,938,634 A | 8/1999 | Packard |
| 5,938,636 A | 8/1999 | Kramer et al. |
| 5,941,846 A | 8/1999 | Duffy et al. |
| 5,944,660 A | 8/1999 | Kimball et al. |
| 5,947,911 A | 9/1999 | Wong et al. |
| 5,954,527 A | 9/1999 | Jhuboo et al. |
| 5,954,696 A | 9/1999 | Ryan et al. |
| 5,956,023 A | 9/1999 | Lyle et al. |
| 5,956,501 A | 9/1999 | Brown |
| 5,957,885 A | 9/1999 | Bollish et al. |
| 5,957,890 A | 9/1999 | Mann et al. |
| 5,971,594 A | 10/1999 | Sahai et al. |
| 5,973,497 A | 10/1999 | Bergk et al. |
| 5,975,081 A | 11/1999 | Hood et al. |
| 5,989,222 A | 11/1999 | Cole et al. |
| 5,990,838 A | 11/1999 | Burns et al. |
| 5,991,525 A | 11/1999 | Shah et al. |
| 5,993,393 A | 11/1999 | Ryan et al. |
| 5,994,876 A | 11/1999 | Canny et al. |
| 5,997,476 A | 12/1999 | Brown |
| 6,000,828 A | 12/1999 | Leet |
| 6,003,006 A | 12/1999 | Colella et al. |
| 6,003,388 A | 12/1999 | Oeftering |
| 6,012,034 A | 1/2000 | Hamparian et al. |
| 6,017,318 A | 1/2000 | Gauthier et al. |
| 6,017,493 A | 1/2000 | Cambron |
| 6,021,392 A | 2/2000 | Lester et al. |
| 6,023,977 A | 2/2000 | Langdon et al. |
| 6,024,539 A | 2/2000 | Blomquist |
| 6,027,441 A | 2/2000 | Cantu |
| 6,032,676 A | 3/2000 | Moore |
| 6,033,561 A | 3/2000 | Schoendorfer |
| 6,036,017 A | 3/2000 | Bayliss, IV |
| 6,068,612 A | 5/2000 | Bowman |
| 6,068,615 A | 5/2000 | Brown et al. |
| 6,073,106 A | 6/2000 | Rozen et al. |
| 6,077,246 A | 6/2000 | Kullas et al. |
| 6,083,206 A | 7/2000 | Molko |
| 6,089,104 A | 7/2000 | Chang |
| 6,104,295 A | 8/2000 | Gaisser et al. |
| 6,110,152 A | 8/2000 | Kovelman |
| 6,110,153 A | 8/2000 | Davis |
| RE36,871 E | 9/2000 | Epstein et al. |
| 6,120,459 A | 9/2000 | Nitzan et al. |
| 6,122,536 A | 9/2000 | Sun et al. |
| 6,142,008 A | 11/2000 | Cole et al. |
| 6,150,942 A | 11/2000 | O'Brien |
| 6,157,914 A | 12/2000 | Seto et al. |
| 6,158,288 A | 12/2000 | Smith |
| 6,158,965 A | 12/2000 | Butterfield et al. |
| 6,159,147 A | 12/2000 | Lichter et al. |
| 6,159,186 A | 12/2000 | Wickham et al. |
| 6,164,921 A | 12/2000 | Moubayed et al. |
| 6,168,561 B1 | 1/2001 | Cantu |
| 6,178,827 B1 | 1/2001 | Feller |
| 6,182,667 B1 | 2/2001 | Hanks et al. |
| 6,186,141 B1 | 2/2001 | Pike et al. |
| 6,189,105 B1 | 2/2001 | Lopes |
| 6,192,752 B1 | 2/2001 | Blaine |
| 6,195,589 B1 | 2/2001 | Ketcham |
| 6,202,711 B1 | 3/2001 | Martucci |
| 6,203,528 B1 | 3/2001 | Deckert |
| 6,208,107 B1 | 3/2001 | Maske et al. |
| 6,212,936 B1 | 4/2001 | Meisberger |
| 6,213,972 B1 | 4/2001 | Butterfield |
| 6,231,320 B1 | 5/2001 | Lawless et al. |
| 6,234,176 B1 | 5/2001 | Domae et al. |
| 6,236,326 B1 | 5/2001 | Murphy et al. |
| 6,237,398 B1 | 5/2001 | Porat et al. |
| 6,241,704 B1 | 6/2001 | Peterson et al. |
| 6,248,067 B1 | 6/2001 | Causey, III et al. |
| 6,250,132 B1 | 6/2001 | Drzewiecki |
| 6,259,355 B1 | 7/2001 | Chaco et al. |
| 6,259,587 B1 | 7/2001 | Sheldon et al. |
| 6,261,065 B1 | 7/2001 | Nayak |
| 6,262,946 B1 | 7/2001 | Khuri-Yakub et al. |
| 6,267,559 B1 | 7/2001 | Mossman et al. |
| 6,267,725 B1 | 7/2001 | Dubberstein et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,277,099 B1 | 8/2001 | Strowe et al. |
| 6,280,380 B1 | 8/2001 | Bardy |
| 6,280,391 B1 | 8/2001 | Olson et al. |
| 6,280,408 B1 | 8/2001 | Sipin |
| 6,283,761 B1 | 9/2001 | Joao |
| 6,285,155 B1 | 9/2001 | Maske et al. |
| 6,312,378 B1 | 11/2001 | Bardy |
| 6,322,516 B1 | 11/2001 | Masuda et al. |
| 6,330,351 B1 | 12/2001 | Yasunaga |
| 6,337,675 B1 | 1/2002 | Toffolo et al. |
| 6,345,539 B1 | 2/2002 | Rawes et al. |
| 6,347,553 B1 | 2/2002 | Morris et al. |
| 6,349,740 B1 | 2/2002 | Cho et al. |
| 6,358,225 B1 | 3/2002 | Butterfield |
| 6,358,387 B1 | 3/2002 | Kopf-Sill et al. |
| 6,362,591 B1 | 3/2002 | Moberg |
| 6,385,505 B1 | 5/2002 | Lipps |
| 6,386,050 B1 | 5/2002 | Yin et al. |
| 6,394,958 B1 | 5/2002 | Bratteli et al. |
| 6,396,583 B1 | 5/2002 | Clare |
| 6,398,760 B1 | 6/2002 | Danby |
| 6,405,076 B1 | 6/2002 | Taylor et al. |
| 6,408,679 B1 | 6/2002 | Kline-Schoder et al. |
| 6,413,238 B1 | 7/2002 | Maget |
| 6,416,291 B1 | 7/2002 | Butterfield et al. |
| 6,418,334 B1 | 7/2002 | Unger et al. |
| 6,418,535 B1 | 7/2002 | Kulakowski et al. |
| 6,445,053 B1 | 9/2002 | Cho |
| 6,456,245 B1 | 9/2002 | Crawford |
| 6,457,346 B1 | 10/2002 | Kline-Schoder et al. |
| 6,463,785 B1 | 10/2002 | Kline-Schoder et al. |
| 6,467,331 B1 | 10/2002 | Kline-Schoder et al. |
| 6,468,242 B1 | 10/2002 | Wilson et al. |
| 6,475,178 B1 | 11/2002 | Krajewski |
| 6,481,980 B1 | 11/2002 | Vandlik |
| 6,482,158 B2 | 11/2002 | Mault |
| 6,482,185 B1 | 11/2002 | Hartmann |
| 6,485,263 B1 | 11/2002 | Bryant et al. |
| 6,485,418 B2 | 11/2002 | Yasushi et al. |
| 6,485,465 B2 | 11/2002 | Moberg et al. |
| 6,487,916 B1 | 12/2002 | Gomm et al. |
| 6,489,896 B1 | 12/2002 | Platt |
| 6,494,694 B2 | 12/2002 | Lawless et al. |
| 6,494,831 B1 | 12/2002 | Koritzinsky |
| 6,497,680 B1 | 12/2002 | Holst et al. |
| 6,503,221 B1 | 1/2003 | Briggs |
| 6,512,944 B1 | 1/2003 | Kovtun et al. |
| 6,516,667 B1 | 2/2003 | Broad et al. |
| 6,517,482 B1 | 2/2003 | Eiden et al. |
| 6,519,569 B1 | 2/2003 | White et al. |
| 6,529,751 B1 | 3/2003 | Van Driel et al. |
| 6,531,708 B1 | 3/2003 | Malmstrom |
| 6,539,315 B1 | 3/2003 | Adams et al. |
| 6,540,672 B1 | 4/2003 | Simonsen et al. |
| 6,544,212 B2 | 4/2003 | Galley et al. |
| 6,544,228 B1 | 4/2003 | Heitmeier |
| 6,558,125 B1 | 5/2003 | Futterknecht |
| 6,558,351 B1 | 5/2003 | Steil et al. |
| 6,562,012 B1 | 5/2003 | Brown et al. |
| 6,564,825 B1 | 5/2003 | Lowery et al. |
| 6,565,509 B1 | 5/2003 | Say et al. |
| 6,568,416 B2 | 5/2003 | Tucker et al. |
| 6,572,542 B1 | 6/2003 | Houben et al. |
| 6,572,545 B2 | 6/2003 | Knobbe et al. |
| 6,572,576 B2 | 6/2003 | Brugger et al. |
| 6,578,422 B2 | 6/2003 | Lam et al. |
| 6,578,435 B2 | 6/2003 | Gould et al. |

(56) References Cited

U.S. PATENT DOCUMENTS

| | | |
|---|---|---|
| 6,581,117 B1 | 6/2003 | Klein et al. |
| RE38,189 E | 7/2003 | Walker et al. |
| 6,585,675 B1 | 7/2003 | O'Mahony et al. |
| 6,589,229 B1 | 7/2003 | Connelly et al. |
| 6,589,792 B1 | 7/2003 | Malachowski |
| 6,599,281 B1 | 7/2003 | Struys et al. |
| 6,599,282 B2 | 7/2003 | Burko |
| 6,602,191 B2 | 8/2003 | Quy |
| 6,605,072 B2 | 8/2003 | Struys et al. |
| 6,609,047 B1 | 8/2003 | Lipps |
| 6,615,674 B2 | 9/2003 | Ohnishi |
| 6,616,633 B1 | 9/2003 | Butterfield et al. |
| 6,617,564 B2 | 9/2003 | Ockerse et al. |
| 6,618,916 B1 | 9/2003 | Eberle et al. |
| 6,622,542 B2 | 9/2003 | Derek |
| 6,622,561 B2 | 9/2003 | Lam et al. |
| D481,121 S | 10/2003 | Evans |
| 6,629,449 B1 | 10/2003 | Kline-Schoder et al. |
| 6,634,233 B2 | 10/2003 | He |
| 6,640,246 B1 | 10/2003 | Gardy, Jr. et al. |
| 6,641,533 B2 | 11/2003 | Causey, III et al. |
| 6,641,541 B1 | 11/2003 | Lovett et al. |
| 6,648,861 B2 | 11/2003 | Platt et al. |
| 6,652,455 B1 | 11/2003 | Kocher |
| 6,653,937 B2 | 11/2003 | Nelson et al. |
| 6,659,980 B2 | 12/2003 | Moberg et al. |
| D485,356 S | 1/2004 | Evans |
| 6,685,668 B1 | 2/2004 | Cho et al. |
| 6,685,678 B2 | 2/2004 | Evans et al. |
| 6,689,069 B2 | 2/2004 | Bratteli et al. |
| 6,689,091 B2 | 2/2004 | Bui et al. |
| 6,692,241 B2 | 2/2004 | Watanabe et al. |
| 6,716,004 B2 | 4/2004 | Vandlik |
| 6,719,535 B2 | 4/2004 | Rakestraw et al. |
| 6,721,582 B2 | 4/2004 | Trepagnier et al. |
| 6,722,211 B1 | 4/2004 | Ciobanu et al. |
| 6,725,200 B1 | 4/2004 | Rost |
| 6,725,721 B2 | 4/2004 | Venczel |
| 6,731,989 B2 | 5/2004 | Engleson et al. |
| 6,732,595 B2 | 5/2004 | Lynnworth |
| 6,738,052 B1 | 5/2004 | Manke et al. |
| 6,740,072 B2 | 5/2004 | Starkweather et al. |
| 6,741,212 B2 | 5/2004 | Kralovec et al. |
| 6,748,808 B2 | 6/2004 | Lam et al. |
| 6,749,403 B2 | 6/2004 | Bryant et al. |
| 6,752,787 B1 | 6/2004 | Causey, III et al. |
| 6,753,842 B1 | 6/2004 | Williams et al. |
| 6,759,007 B1 | 7/2004 | Westberg |
| 6,760,643 B2 | 7/2004 | Lipps |
| 6,768,920 B2 | 7/2004 | Lange |
| 6,773,412 B2 | 8/2004 | O'Mahony |
| 6,780,156 B2 | 8/2004 | Haueter et al. |
| 6,783,328 B2 | 8/2004 | Lucke et al. |
| 6,785,573 B2 | 8/2004 | Kovtun et al. |
| 6,786,885 B2 | 9/2004 | Hochman et al. |
| 6,789,426 B2 | 9/2004 | Yaralioglu et al. |
| 6,790,198 B1 | 9/2004 | White et al. |
| 6,793,625 B2 | 9/2004 | Cavallaro et al. |
| 6,801,227 B2 | 10/2004 | Bocionek et al. |
| 6,805,671 B2 | 10/2004 | Stergiopoulos et al. |
| 6,807,965 B1 | 10/2004 | Hickle |
| 6,809,653 B1 | 10/2004 | Mann et al. |
| 6,813,964 B1 | 11/2004 | Clark et al. |
| 6,814,547 B2 | 11/2004 | Childers |
| 6,824,528 B1 | 11/2004 | Faries |
| 6,830,558 B2 | 12/2004 | Flaherty et al. |
| 6,840,113 B2 | 1/2005 | Fukumura et al. |
| 6,846,161 B2 | 1/2005 | Kline |
| 6,852,094 B2 | 2/2005 | Beck |
| 6,852,104 B2 | 2/2005 | Blomquist |
| 6,854,338 B2 | 2/2005 | Khuri-Yakub et al. |
| 6,857,318 B1 | 2/2005 | Silber et al. |
| 6,869,425 B2 | 3/2005 | Briggs et al. |
| 6,873,268 B2 | 3/2005 | Lebel et al. |
| 6,883,376 B2 | 4/2005 | He |
| 6,885,881 B2 | 4/2005 | Leonhardt |
| 6,887,216 B2 | 5/2005 | Hochman et al. |
| 6,898,301 B2 | 5/2005 | Iwanaga |
| 6,907,361 B2 | 6/2005 | Molenaar |
| 6,907,792 B2 | 6/2005 | Ohnishi |
| 6,915,170 B2 | 7/2005 | Engleson et al. |
| 6,920,795 B2 | 7/2005 | Bischoff et al. |
| 6,923,763 B1 | 8/2005 | Kovatchev et al. |
| 6,928,338 B1 | 8/2005 | Buchser et al. |
| 6,929,619 B2 | 8/2005 | Fago et al. |
| 6,929,751 B2 | 8/2005 | Bowman |
| 6,932,114 B2 | 8/2005 | Sparks |
| 6,932,796 B2 | 8/2005 | Sage et al. |
| 6,935,192 B2 | 8/2005 | Sobek et al. |
| 6,936,029 B2 | 8/2005 | Mann et al. |
| 6,941,005 B2 | 9/2005 | Lary et al. |
| 6,942,636 B2 | 9/2005 | Holst et al. |
| 6,945,954 B2 | 9/2005 | Hochman et al. |
| 6,958,705 B2 | 10/2005 | Lebel et al. |
| 6,964,204 B2 | 11/2005 | Clark et al. |
| 6,973,374 B2 | 12/2005 | Ader |
| 6,974,437 B2 | 12/2005 | Lebel et al. |
| 6,975,922 B2 | 12/2005 | Duncan et al. |
| 6,978,779 B2 | 12/2005 | Haveri et al. |
| 6,979,326 B2 | 12/2005 | Mann et al. |
| 6,981,960 B2 | 1/2006 | Cho et al. |
| 6,984,218 B2 | 1/2006 | Nayak et al. |
| 6,985,768 B2 | 1/2006 | Hemming et al. |
| 6,985,870 B2 | 1/2006 | Martucci et al. |
| 6,986,347 B2 | 1/2006 | Hickle |
| 6,986,753 B2 | 1/2006 | Bui |
| 6,997,905 B2 | 2/2006 | Gillespie, Jr. et al. |
| 6,997,920 B2 | 2/2006 | Mann et al. |
| 7,006,005 B2 | 2/2006 | Nazarian et al. |
| 7,017,623 B2 | 3/2006 | Tribble et al. |
| 7,021,148 B2 | 4/2006 | Kuhn |
| 7,025,743 B2 | 4/2006 | Mann et al. |
| 7,029,455 B2 | 4/2006 | Flaherty |
| 7,029,456 B2 | 4/2006 | Ware et al. |
| 7,059,184 B2 | 6/2006 | Kanouola et al. |
| 7,060,059 B2 | 6/2006 | Keith et al. |
| 7,069,793 B2 | 7/2006 | Ishikawa et al. |
| 7,072,725 B2 | 7/2006 | Bristol et al. |
| 7,074,209 B2 | 7/2006 | Evans et al. |
| 7,080,557 B2 | 7/2006 | Adnan |
| 7,082,843 B2 | 8/2006 | Clark et al. |
| 7,087,444 B2 | 8/2006 | Wong et al. |
| 7,092,796 B2 | 8/2006 | Vanderveen |
| 7,092,797 B2 | 8/2006 | Gaines et al. |
| 7,093,502 B2 | 8/2006 | Kupnik et al. |
| 7,096,729 B2 | 8/2006 | Repko et al. |
| 7,103,419 B2 | 9/2006 | Engleson et al. |
| 7,104,763 B2 | 9/2006 | Bouton et al. |
| 7,104,769 B2 | 9/2006 | Davis |
| 7,108,680 B2 | 9/2006 | Rohr et al. |
| 7,109,878 B2 | 9/2006 | Mann et al. |
| 7,115,113 B2 | 10/2006 | Evans et al. |
| 7,117,041 B2 | 10/2006 | Engleson et al. |
| 7,137,964 B2 | 11/2006 | Flaherty |
| 7,141,037 B2 | 11/2006 | Butterfield et al. |
| 7,152,490 B1 | 12/2006 | Freund, Jr. et al. |
| 7,154,397 B2 | 12/2006 | Zerhusen et al. |
| 7,161,488 B2 | 1/2007 | Frasch |
| 7,162,290 B1 | 1/2007 | Levin |
| 7,162,927 B1 | 1/2007 | Selvan et al. |
| 7,171,277 B2 | 1/2007 | Engleson et al. |
| 7,174,789 B2 | 2/2007 | Orr et al. |
| 7,185,288 B2 | 2/2007 | McKeever |
| 7,197,943 B2 | 4/2007 | Lee et al. |
| 7,201,734 B2 | 4/2007 | Hickle |
| 7,204,823 B2 | 4/2007 | Estes et al. |
| 7,206,715 B2 | 4/2007 | Vanderveen et al. |
| 7,213,009 B2 | 5/2007 | Pestotnik |
| 7,220,240 B2 | 5/2007 | Struys et al. |
| 7,229,430 B2 | 6/2007 | Hickle et al. |
| 7,230,529 B2 | 6/2007 | Ketcherside |
| 7,232,430 B2 | 6/2007 | Carlisle |
| 7,238,164 B2 | 7/2007 | Childers et al. |
| 7,247,154 B2 | 7/2007 | Hickle |

(56) References Cited

U.S. PATENT DOCUMENTS

| | | |
|---|---|---|
| 7,253,779 B2 | 8/2007 | Greer et al. |
| 7,254,425 B2 | 8/2007 | Lowery et al. |
| 7,258,534 B2 | 8/2007 | Fathallah et al. |
| 7,267,664 B2 | 9/2007 | Rizzo |
| 7,267,665 B2 | 9/2007 | Steil et al. |
| 7,272,529 B2 | 9/2007 | Hogan et al. |
| 7,278,983 B2 | 10/2007 | Ireland et al. |
| 7,291,123 B2 | 11/2007 | Baraldi et al. |
| 7,293,461 B1 | 11/2007 | Gimdt |
| 7,294,109 B2 | 11/2007 | Lovett et al. |
| 7,296,482 B2 | 11/2007 | Schaffer et al. |
| 7,300,418 B2 | 11/2007 | Zaleski |
| 7,305,883 B2 | 12/2007 | Khuri-Yakub et al. |
| 7,327,273 B2 | 2/2008 | Hung et al. |
| 7,338,470 B2 | 3/2008 | Katz |
| 7,347,836 B2 | 3/2008 | Peterson et al. |
| 7,354,420 B2 | 4/2008 | Steil et al. |
| 7,356,382 B2 | 4/2008 | Vanderveen |
| 7,360,999 B2 | 4/2008 | Nelson et al. |
| 7,364,562 B2 | 4/2008 | Braig et al. |
| 7,367,942 B2 | 5/2008 | Grage et al. |
| 7,369,948 B1 | 5/2008 | Ferenczi et al. |
| 7,384,410 B2 | 6/2008 | Eggers et al. |
| 7,397,166 B1 | 7/2008 | Morgan et al. |
| 7,398,183 B2 | 7/2008 | Holland et al. |
| 7,399,277 B2 | 7/2008 | Saidara et al. |
| 7,402,153 B2 | 7/2008 | Steil et al. |
| 7,402,154 B2 | 7/2008 | Mendez |
| 7,407,489 B2 | 8/2008 | Mendez |
| 7,414,534 B1 | 8/2008 | Kroll et al. |
| 7,415,895 B2 | 8/2008 | Kurisaki et al. |
| 7,426,443 B2 | 9/2008 | Simon |
| 7,430,675 B2 | 9/2008 | Lee et al. |
| 7,447,566 B2 | 11/2008 | Knauper et al. |
| 7,447,643 B1 | 11/2008 | Olson |
| 7,452,190 B2 | 11/2008 | Bouton et al. |
| 7,454,314 B2 | 11/2008 | Holland et al. |
| 7,471,994 B2 | 12/2008 | Ford et al. |
| 7,482,818 B2 | 1/2009 | Greenwald et al. |
| 7,483,756 B2 | 1/2009 | Engleson et al. |
| 7,490,021 B2 | 2/2009 | Holland et al. |
| 7,491,187 B2 | 2/2009 | Van Den Berghe et al. |
| 7,503,903 B2 | 3/2009 | Carlisle et al. |
| 7,517,332 B2 | 4/2009 | Tonelli et al. |
| 7,523,401 B1 | 4/2009 | Aldridge |
| 7,545,075 B2 | 6/2009 | Huang et al. |
| 7,556,616 B2 | 7/2009 | Fathallah et al. |
| 7,561,986 B2 | 7/2009 | Vanderveen et al. |
| 7,571,024 B2 | 8/2009 | Duncan et al. |
| 7,645,258 B2 | 1/2010 | White et al. |
| 7,654,127 B2 | 2/2010 | Krulevitch et al. |
| 7,657,443 B2 | 2/2010 | Crass |
| 7,668,731 B2 | 2/2010 | Martucci et al. |
| 7,678,048 B1 | 3/2010 | Urbano et al. |
| 7,693,697 B2 | 4/2010 | Westenkow et al. |
| 7,699,806 B2 | 4/2010 | Ware et al. |
| 7,705,727 B2 | 4/2010 | Pestotnik |
| 7,766,873 B2 | 8/2010 | Moberg et al. |
| 7,775,126 B2 | 8/2010 | Eckhardt |
| 7,775,127 B2 | 8/2010 | Wade |
| 7,785,284 B2 | 8/2010 | Baralsi et al. |
| 7,785,313 B2 | 8/2010 | Mastrototaro |
| 7,786,909 B2 | 8/2010 | Udupa et al. |
| 7,806,886 B2 | 10/2010 | Kanderian, Jr. et al. |
| 7,826,981 B2 | 11/2010 | Goode, Jr. et al. |
| 7,847,276 B2 | 12/2010 | Carlisle |
| 7,860,583 B2 | 12/2010 | Condurso et al. |
| 7,871,394 B2 | 1/2011 | Halbert et al. |
| 7,876,443 B2 | 1/2011 | Bernacki |
| 7,895,053 B2 | 2/2011 | Holland et al. |
| 7,895,882 B2 | 3/2011 | Carlisle |
| 7,896,834 B2 | 3/2011 | Smisson, III |
| 7,896,842 B2 | 3/2011 | Palmroos et al. |
| 7,905,710 B2 | 3/2011 | Wang et al. |
| 7,933,780 B2 | 4/2011 | de la Huerga |
| 7,945,452 B2 | 5/2011 | Fathallah et al. |
| 7,981,073 B2 | 7/2011 | Mollstam |
| 7,981,082 B2 | 7/2011 | Wang et al. |
| 8,034,020 B2 | 10/2011 | Dewey |
| 8,038,593 B2 | 10/2011 | Friedman et al. |
| 8,065,161 B2 | 11/2011 | Howard et al. |
| 8,067,760 B2 | 11/2011 | Carlisle |
| 8,075,546 B2 | 12/2011 | Carlisle et al. |
| 8,078,983 B2 | 12/2011 | Davis et al. |
| 8,121,857 B2 | 2/2012 | Galasso et al. |
| 8,149,131 B2 | 4/2012 | Blornquist |
| 8,175,668 B1 | 5/2012 | Nabutovsky et al. |
| 8,177,739 B2 | 5/2012 | Cartledge et al. |
| 8,185,322 B2 | 5/2012 | Schroeder et al. |
| 8,219,413 B2 | 7/2012 | Martinez et al. |
| 8,226,597 B2 | 7/2012 | Jacobson et al. |
| 8,231,578 B2 | 7/2012 | Fathallah et al. |
| 8,234,128 B2 | 7/2012 | Martucci et al. |
| 8,271,106 B2 | 9/2012 | Wehba et al. |
| 8,287,514 B2 | 10/2012 | Miller et al. |
| 8,291,337 B2 | 10/2012 | Gannin et al. |
| 8,313,308 B2 | 11/2012 | Lawless et al. |
| 8,317,698 B2 | 11/2012 | Lowery |
| 8,317,750 B2 | 11/2012 | Ware et al. |
| 8,317,752 B2 | 11/2012 | Cozmi et al. |
| 8,318,094 B1 | 11/2012 | Bayandorian et al. |
| 8,340,792 B2 | 12/2012 | Condurso et al. |
| 8,347,731 B2 | 1/2013 | Genosar |
| 8,359,338 B2 | 1/2013 | Butterfield et al. |
| 8,361,021 B2 | 1/2013 | Wang et al. |
| 8,378,837 B2 | 2/2013 | Wang et al. |
| 8,388,598 B2 | 3/2013 | Steinkogler |
| 8,398,616 B2 | 3/2013 | Budiman |
| 8,403,908 B2 | 3/2013 | Jacobson et al. |
| 8,449,524 B2 | 5/2013 | Braig et al. |
| 8,477,307 B1 | 7/2013 | Yufa et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,539,812 B2 | 9/2013 | Stringham et al. |
| 8,543,416 B2 | 9/2013 | Palmroos et al. |
| 8,577,692 B2 | 11/2013 | Silkaitis et al. |
| 8,622,990 B2 | 1/2014 | Estes et al. |
| 8,630,722 B2 | 1/2014 | Condurso et al. |
| 8,665,214 B2 | 3/2014 | Forutanpour et al. |
| 8,666,769 B2 | 3/2014 | Butler et al. |
| 8,700,421 B2 | 4/2014 | Feng et al. |
| 8,706,233 B2 | 4/2014 | Su et al. |
| 8,721,584 B2 | 5/2014 | Braithwaite et al. |
| 8,761,906 B2 | 6/2014 | Condurso et al. |
| 8,768,719 B2 | 7/2014 | Wehba et al. |
| 8,771,251 B2 | 7/2014 | Ruchti et al. |
| 8,792,981 B2 | 7/2014 | Yudovsky et al. |
| 8,821,432 B2 | 9/2014 | Unverdorben |
| 8,823,382 B2 | 9/2014 | Rondoni et al. |
| 8,857,269 B2 | 10/2014 | Johnson et al. |
| 8,858,185 B2 | 10/2014 | Johnson et al. |
| 8,964,185 B1 | 2/2015 | Luo et al. |
| 9,005,150 B2 | 4/2015 | Ware et al. |
| 9,026,370 B2 | 5/2015 | Rubalcaba et al. |
| 9,084,855 B2 | 7/2015 | Ware et al. |
| 9,114,217 B2 | 8/2015 | Sur et al. |
| 9,134,735 B2 | 9/2015 | Lowery et al. |
| 9,134,736 B2 | 9/2015 | Lowery et al. |
| 9,138,526 B2 | 9/2015 | Ware et al. |
| 9,190,010 B2 | 11/2015 | Vik et al. |
| 9,240,002 B2 | 1/2016 | Hume et al. |
| 9,272,089 B2 | 3/2016 | Jacobson et al. |
| 9,333,291 B2 | 5/2016 | Jacobson et al. |
| 9,381,296 B2 | 7/2016 | Arrizza et al. |
| 9,393,362 B2 | 7/2016 | Cozmi et al. |
| 9,468,718 B2 | 10/2016 | Hung et al. |
| 9,498,583 B2 | 11/2016 | Sur et al. |
| 9,707,341 B2 | 7/2017 | Dumas, III et al. |
| 9,943,269 B2 | 4/2018 | Muhsin et al. |
| 9,995,611 B2 | 6/2018 | Ruchti et al. |
| 10,022,498 B2 | 7/2018 | Ruchti et al. |
| 10,046,112 B2 | 8/2018 | Oruklu et al. |

(56) References Cited

U.S. PATENT DOCUMENTS

| | | |
|---|---|---|
| 2001/0007636 A1 | 7/2001 | Butterfield |
| 2001/0014769 A1 | 8/2001 | Bufe et al. |
| 2001/0015099 A1 | 8/2001 | Blaine |
| 2001/0016056 A1 | 8/2001 | Westphal et al. |
| 2001/0032099 A1 | 10/2001 | Joao |
| 2001/0037060 A1 | 11/2001 | Thompson et al. |
| 2001/0041869 A1 | 11/2001 | Causey et al. |
| 2001/0044731 A1 | 11/2001 | Coffman et al. |
| 2002/0003892 A1 | 1/2002 | Iwanaga |
| 2002/0007116 A1 | 1/2002 | Zatezalo et al. |
| 2002/0013545 A1 | 1/2002 | Soltanpour et al. |
| 2002/0013551 A1 | 1/2002 | Zaitsu et al. |
| 2002/0015018 A1 | 2/2002 | Shimazu et al. |
| 2002/0018720 A1 | 2/2002 | Carlisle et al. |
| 2002/0029776 A1 | 3/2002 | Blomquist |
| 2002/0031838 A1 | 3/2002 | Meinhart et al. |
| 2002/0032583 A1 | 3/2002 | Joao |
| 2002/0040208 A1 | 4/2002 | Flaherty et al. |
| 2002/0044059 A1 | 4/2002 | Reeder et al. |
| 2002/0045806 A1 | 4/2002 | Baker, Jr. et al. |
| 2002/0082728 A1 | 6/2002 | Mueller et al. |
| 2002/0083771 A1 | 7/2002 | Khuri-Yakub et al. |
| 2002/0085952 A1 | 7/2002 | Ellingboe et al. |
| 2002/0087115 A1 | 7/2002 | Hartlaub |
| 2002/0095486 A1 | 7/2002 | Bahl |
| 2002/0099282 A1 | 7/2002 | Knobbe et al. |
| 2002/0099334 A1 | 7/2002 | Hanson et al. |
| 2002/0143580 A1 | 10/2002 | Bristol et al. |
| 2002/0147389 A1 | 10/2002 | Cavallaro et al. |
| 2002/0152239 A1 | 10/2002 | Bautista-Lloyd et al. |
| 2002/0168278 A1 | 11/2002 | Jeon et al. |
| 2002/0173703 A1 | 11/2002 | Lebel et al. |
| 2002/0183693 A1 | 12/2002 | Peterson et al. |
| 2003/0009244 A1 | 1/2003 | Engleson |
| 2003/0013959 A1 | 1/2003 | Grunwald et al. |
| 2003/0018308 A1 | 1/2003 | Tsai |
| 2003/0025602 A1 | 2/2003 | Medema et al. |
| 2003/0028082 A1 | 2/2003 | Thompson |
| 2003/0030001 A1 | 2/2003 | Cooper et al. |
| 2003/0045840 A1 | 3/2003 | Burko |
| 2003/0050621 A1 | 3/2003 | Lebel et al. |
| 2003/0060688 A1 | 3/2003 | Ciarniello et al. |
| 2003/0060765 A1 | 3/2003 | Campbell et al. |
| 2003/0065537 A1 | 4/2003 | Evans |
| 2003/0065589 A1 | 4/2003 | Giacchetti |
| 2003/0073954 A1 | 4/2003 | Moberg et al. |
| 2003/0079746 A1 | 5/2003 | Hickle |
| 2003/0083583 A1 | 5/2003 | Kovtun et al. |
| 2003/0091442 A1 | 5/2003 | Bush et al. |
| 2003/0104982 A1 | 6/2003 | Wittmann et al. |
| 2003/0106553 A1 | 6/2003 | Vanderveen |
| 2003/0125662 A1 | 7/2003 | Bui |
| 2003/0130616 A1 | 7/2003 | Steil |
| 2003/0135087 A1 | 7/2003 | Hickle et al. |
| 2003/0136193 A1 | 7/2003 | Fujimoto |
| 2003/0139701 A1 | 7/2003 | White et al. |
| 2003/0140928 A1 | 7/2003 | Bui et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158508 A1 | 8/2003 | DiGianfilippo |
| 2003/0160683 A1 | 8/2003 | Blomquist |
| 2003/0163789 A1 | 8/2003 | Blomquist |
| 2003/0173408 A1 | 9/2003 | Mosher, Jr. et al. |
| 2003/0187338 A1 | 10/2003 | Say et al. |
| 2003/0200116 A1 | 10/2003 | Forrester |
| 2003/0204274 A1 | 10/2003 | Ullestad et al. |
| 2003/0204416 A1 | 10/2003 | Acharya |
| 2003/0212364 A1 | 11/2003 | Mann et al. |
| 2003/0212379 A1 | 11/2003 | Bylund et al. |
| 2003/0217962 A1 | 11/2003 | Childers et al. |
| 2003/0233071 A1 | 12/2003 | Gillespie, Jr. et al. |
| 2004/0030277 A1 | 2/2004 | O'Mahony et al. |
| 2004/0047736 A1 | 3/2004 | Nose et al. |
| 2004/0057226 A1 | 3/2004 | Berthou et al. |
| 2004/0064342 A1 | 4/2004 | Browne et al. |
| 2004/0073125 A1 | 4/2004 | Lovett et al. |
| 2004/0073161 A1 | 4/2004 | Tachibana |
| 2004/0077996 A1 | 4/2004 | Jasperson et al. |
| 2004/0082908 A1 | 4/2004 | Whitehurst |
| 2004/0082918 A1 | 4/2004 | Evans et al. |
| 2004/0104271 A1 | 6/2004 | Martucci et al. |
| 2004/0119753 A1 | 6/2004 | Zencke |
| 2004/0120825 A1 | 6/2004 | Bouton et al. |
| 2004/0145114 A1 | 6/2004 | Ippolito et al. |
| 2004/0128162 A1 | 7/2004 | Schlotterbeck et al. |
| 2004/0133166 A1 | 7/2004 | Moberg et al. |
| 2004/0147034 A1 | 7/2004 | Gore et al. |
| 2004/0149823 A1 | 8/2004 | Aptekar |
| 2004/0152970 A1 | 8/2004 | Hunter et al. |
| 2004/0158193 A1 | 8/2004 | Bui et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172289 A1 | 9/2004 | Kozic et al. |
| 2004/0172302 A1 | 9/2004 | Martucci et al. |
| 2004/0176984 A1 | 9/2004 | White et al. |
| 2004/0181314 A1 | 9/2004 | Zaleski |
| 2004/0193025 A1 | 9/2004 | Steil et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204638 A1 | 10/2004 | Diab et al. |
| 2004/0204673 A1 | 10/2004 | Flaherty et al. |
| 2004/0220517 A1 | 11/2004 | Starkweather et al. |
| 2004/0225252 A1 | 11/2004 | Gillespie et al. |
| 2004/0225409 A1 | 11/2004 | Duncan et al. |
| 2004/0232219 A1 | 11/2004 | Fowler |
| 2004/0247445 A1 | 12/2004 | Nelson et al. |
| 2004/0253123 A1 | 12/2004 | Xie et al. |
| 2004/0254434 A1 | 12/2004 | Goodnow et al. |
| 2004/0254513 A1 | 12/2004 | Shang et al. |
| 2005/0021006 A1 | 1/2005 | Tonnies |
| 2005/0021297 A1 | 1/2005 | Hartlaub |
| 2005/0022274 A1 | 1/2005 | Campbell et al. |
| 2005/0038680 A1 | 2/2005 | McMahon |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0075544 A1 | 4/2005 | Shapiro et al. |
| 2005/0096593 A1 | 5/2005 | Pope et al. |
| 2005/0099624 A1 | 5/2005 | Staehr |
| 2005/0107923 A1 | 5/2005 | Vanderveen |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0143864 A1 | 6/2005 | Blomquist |
| 2005/0145010 A1 | 7/2005 | Vanderveen et al. |
| 2005/0171503 A1 | 8/2005 | Van Den Berghe et al. |
| 2005/0171815 A1 | 8/2005 | Vanderveen |
| 2005/0177045 A1 | 8/2005 | Degertekin et al. |
| 2005/0177096 A1 | 8/2005 | Bollish et al. |
| 2005/0182306 A1 | 8/2005 | Sloan |
| 2005/0182355 A1 | 8/2005 | Bui |
| 2005/0182366 A1 | 8/2005 | Vogt et al. |
| 2005/0187515 A1 | 8/2005 | Varrichio et al. |
| 2005/0192529 A1 | 9/2005 | Butterfield et al. |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0209563 A1 | 9/2005 | Hopping et al. |
| 2005/0209793 A1 | 9/2005 | Yamada |
| 2005/0224083 A1 | 10/2005 | Crass |
| 2005/0235732 A1 | 10/2005 | Rush |
| 2005/0238506 A1 | 10/2005 | Mescher et al. |
| 2005/0240305 A1 | 10/2005 | Bogash et al. |
| 2005/0273059 A1 | 12/2005 | Mernoe et al. |
| 2005/0277890 A1 | 12/2005 | Stewart et al. |
| 2005/0279419 A1 | 12/2005 | Tribble et al. |
| 2006/0002799 A1 | 1/2006 | Schann et al. |
| 2006/0009727 A1 | 1/2006 | O'Mahony et al. |
| 2006/0009734 A1 | 1/2006 | Martin |

(56) References Cited

U.S. PATENT DOCUMENTS

| | | |
|---|---|---|
| 2006/0042633 A1 | 3/2006 | Bishop et al. |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0064053 A1 | 3/2006 | Bollish et al. |
| 2006/0079768 A1 | 4/2006 | Small et al. |
| 2006/0079831 A1 | 4/2006 | Gilbert |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0116639 A1 | 6/2006 | Russell |
| 2006/0117856 A1 | 6/2006 | Orr et al. |
| 2006/0117867 A1 | 6/2006 | Froehlich et al. |
| 2006/0122867 A1 | 6/2006 | Eggers et al. |
| 2006/0135939 A1 | 6/2006 | Brown |
| 2006/0135940 A1 | 6/2006 | Joshi |
| 2006/0136271 A1 | 6/2006 | Eggers et al. |
| 2006/0140798 A1 | 6/2006 | Kutsuzawa |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0180916 A1 | 8/2006 | Wyland |
| 2006/0181695 A1 | 8/2006 | Sage, Jr. |
| 2006/0187069 A1 | 8/2006 | Duan |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0224181 A1 | 10/2006 | McEwen et al. |
| 2006/0226088 A1 | 10/2006 | Robinson et al. |
| 2006/0226089 A1 | 10/2006 | Robinson et al. |
| 2006/0226090 A1 | 10/2006 | Robinson et al. |
| 2006/0229557 A1 | 10/2006 | Fathallah et al. |
| 2006/0229918 A1 | 10/2006 | Fotsch et al. |
| 2006/0235353 A1 | 10/2006 | Gelfand et al. |
| 2006/0258985 A1 | 11/2006 | Russell |
| 2006/0260416 A1 | 11/2006 | Sage et al. |
| 2006/0264895 A1 | 11/2006 | Flanders |
| 2006/0265246 A1 | 11/2006 | Hoag |
| 2006/0266128 A1 | 11/2006 | Clark et al. |
| 2006/0270971 A1 | 11/2006 | Gelfand et al. |
| 2006/0271286 A1 | 11/2006 | Rosenberg |
| 2006/0272421 A1 | 12/2006 | Frinak et al. |
| 2006/0275142 A1 | 12/2006 | Bouton et al. |
| 2007/0015972 A1 | 1/2007 | Wang et al. |
| 2007/0036511 A1 | 2/2007 | Lundquist et al. |
| 2007/0060796 A1 | 3/2007 | Kim |
| 2007/0060871 A1 | 3/2007 | Istoc |
| 2007/0060872 A1 | 3/2007 | Hall et al. |
| 2007/0060874 A1 | 3/2007 | Nesbitt et al. |
| 2007/0062250 A1 | 3/2007 | Krulevitch et al. |
| 2007/0065363 A1 | 3/2007 | Dalal et al. |
| 2007/0078314 A1 | 4/2007 | Grounsell |
| 2007/0083152 A1 | 4/2007 | Williams, Jr. et al. |
| 2007/0084288 A1 | 4/2007 | Thomas et al. |
| 2007/0088271 A1 | 4/2007 | Richards |
| 2007/0088333 A1 | 4/2007 | Levin et al. |
| 2007/0100222 A1 | 5/2007 | Mastrototaro et al. |
| 2007/0100665 A1 | 5/2007 | Brown |
| 2007/0112298 A1 | 5/2007 | Mueller et al. |
| 2007/0118405 A1 | 5/2007 | Campbell et al. |
| 2007/0129618 A1 | 6/2007 | Goldberger et al. |
| 2007/0142822 A1 | 6/2007 | Remde |
| 2007/0156452 A1 | 7/2007 | Batch |
| 2007/0179436 A1 | 8/2007 | Braig et al. |
| 2007/0191817 A1 | 8/2007 | Martin |
| 2007/0214003 A1 | 9/2007 | Holland et al. |
| 2007/0215545 A1 | 9/2007 | Bissler et al. |
| 2007/0233035 A1 | 10/2007 | Wehba et al. |
| 2007/0233049 A1 | 10/2007 | Wehba et al. |
| 2007/0240497 A1 | 10/2007 | Robinson et al. |
| 2007/0255250 A1 | 11/2007 | Moberg et al. |
| 2007/0257788 A1 | 11/2007 | Carlson |
| 2007/0267945 A1 | 11/2007 | Sudol |
| 2007/0270747 A1 | 11/2007 | Remde |
| 2007/0274843 A1 | 11/2007 | Vanderveen et al. |
| 2007/0289384 A1 | 12/2007 | Sakai et al. |
| 2008/0009684 A1 | 1/2008 | Corsetti et al. |
| 2008/0028868 A1 | 2/2008 | Konzelmann et al. |
| 2008/0033361 A1 | 2/2008 | Evans et al. |
| 2008/0039777 A1 | 2/2008 | Katz et al. |
| 2008/0048211 A1 | 2/2008 | Khuri-Yakub et al. |
| 2008/0058773 A1 | 3/2008 | John |
| 2008/0060448 A1 | 3/2008 | Wiest et al. |
| 2008/0065420 A1 | 3/2008 | Tirinato et al. |
| 2008/0071210 A1 | 3/2008 | Moubayed et al. |
| 2008/0071496 A1 | 3/2008 | Glascock |
| 2008/0071580 A1 | 3/2008 | Marcus et al. |
| 2008/0091466 A1 | 4/2008 | Butler et al. |
| 2008/0097288 A1 | 4/2008 | Levin et al. |
| 2008/0097289 A1 | 4/2008 | Steil et al. |
| 2008/0097317 A1 | 4/2008 | Alholm et al. |
| 2008/0098798 A1 | 5/2008 | Riley et al. |
| 2008/0119822 A1 | 5/2008 | Knauper |
| 2008/0125701 A1 | 5/2008 | Moberg et al. |
| 2008/0139907 A1 | 6/2008 | Rao et al. |
| 2008/0145249 A1 | 6/2008 | Smisson |
| 2008/0172030 A1 | 7/2008 | Blomquist et al. |
| 2008/0177254 A1 | 7/2008 | Shelton et al. |
| 2008/0184784 A1 | 8/2008 | Dam |
| 2008/0188789 A1 | 8/2008 | Galavotti et al. |
| 2008/0188796 A1 | 8/2008 | Steil et al. |
| 2008/0200870 A1 | 8/2008 | Palmroos et al. |
| 2008/0208484 A1 | 8/2008 | Butterfield et al. |
| 2008/0214919 A1 | 9/2008 | Harmon et al. |
| 2008/0221521 A1 | 9/2008 | Getz et al. |
| 2008/0221522 A1 | 9/2008 | Moberg et al. |
| 2008/0243055 A1 | 10/2008 | Fathallah et al. |
| 2008/0262469 A1 | 10/2008 | Bristol et al. |
| 2008/0269663 A1 | 10/2008 | Arnold et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2009/0001908 A1 | 1/2009 | Shubinsky et al. |
| 2009/0005703 A1 | 1/2009 | Fasciano |
| 2009/0006061 A1 | 1/2009 | Thukral et al. |
| 2009/0006129 A1 | 1/2009 | Thukral |
| 2009/0006133 A1 | 1/2009 | Weinert |
| 2009/0015824 A1 | 1/2009 | Shubinsky et al. |
| 2009/0043171 A1 | 2/2009 | Rule |
| 2009/0054743 A1 | 2/2009 | Stewart |
| 2009/0054754 A1 | 2/2009 | McMahon et al. |
| 2009/0069743 A1 | 3/2009 | Krishnamoorthy et al. |
| 2009/0077248 A1 | 3/2009 | Castellucci et al. |
| 2009/0082676 A1 | 3/2009 | Bennison |
| 2009/0088731 A1 | 4/2009 | Campbell et al. |
| 2009/0097029 A1 | 4/2009 | Tokhtuev et al. |
| 2009/0112155 A1 | 4/2009 | Zhao |
| 2009/0124963 A1 | 5/2009 | Hogard et al. |
| 2009/0124964 A1 | 5/2009 | Leach et al. |
| 2009/0131861 A1 | 5/2009 | Braig et al. |
| 2009/0135196 A1 | 5/2009 | Holland et al. |
| 2009/0143726 A1 | 6/2009 | Bouton et al. |
| 2009/0144025 A1 | 6/2009 | Bouton et al. |
| 2009/0144026 A1 | 6/2009 | Bouton et al. |
| 2009/0149743 A1 | 6/2009 | Barron et al. |
| 2009/0156922 A1 | 6/2009 | Goldberger et al. |
| 2009/0156975 A1 | 6/2009 | Robinson et al. |
| 2009/0157040 A1* | 6/2009 | Jacobson .......... A61M 5/16804 604/505 |
| 2009/0177146 A1 | 7/2009 | Nesbitt et al. |
| 2009/0177188 A1 | 7/2009 | Steinkogler |
| 2009/0177248 A1 | 7/2009 | Roberts |
| 2009/0177769 A1 | 7/2009 | Roberts |
| 2009/0177992 A1 | 7/2009 | Rubalcaba et al. |
| 2009/0178485 A1 | 7/2009 | Thomas et al. |
| 2009/0183147 A1 | 7/2009 | Davis et al. |
| 2009/0192367 A1 | 7/2009 | Braig et al. |
| 2009/0205426 A1 | 8/2009 | Balschat et al. |
| 2009/0209938 A1 | 8/2009 | Aalto-Setala |
| 2009/0209945 A1 | 8/2009 | Lobl et al. |

(56) References Cited

U.S. PATENT DOCUMENTS

| | | |
|---|---|---|
| 2009/0212966 A1 | 8/2009 | Panduro |
| 2009/0221890 A1 | 9/2009 | Saffer et al. |
| 2009/0223294 A1 | 9/2009 | Thomas et al. |
| 2009/0227939 A1 | 9/2009 | Memoe et al. |
| 2009/0264720 A1 | 10/2009 | Torjman et al. |
| 2009/0270810 A1 | 10/2009 | DeBelser |
| 2009/0270833 A1 | 10/2009 | DeBelser |
| 2010/0022988 A1 | 1/2010 | Wochner |
| 2010/0280430 A1 | 1/2010 | Caleffi et al. |
| 2010/0036310 A1 | 2/2010 | Hillman |
| 2010/0056992 A1 | 3/2010 | Hayter |
| 2010/0069892 A1 | 3/2010 | Steinbach et al. |
| 2010/0077866 A1 | 4/2010 | Graboi et al. |
| 2010/0079760 A1 | 4/2010 | Bernacki |
| 2010/0094251 A1 | 4/2010 | Estes et al. |
| 2010/0106082 A1 | 4/2010 | Zhou |
| 2010/0121170 A1 | 5/2010 | Rule |
| 2010/0121415 A1 | 5/2010 | Skelton et al. |
| 2010/0130933 A1 | 5/2010 | Holland et al. |
| 2010/0131434 A1 | 5/2010 | Magent et al. |
| 2010/0141460 A1 | 6/2010 | Tokhtuev et al. |
| 2010/0147081 A1 | 6/2010 | Thomas et al. |
| 2010/0152554 A1 | 6/2010 | Steine et al. |
| 2010/0160854 A1 | 6/2010 | Gauthier |
| 2010/0168535 A1 | 7/2010 | Robinson et al. |
| 2010/0177375 A1 | 7/2010 | Seyfried |
| 2010/0185142 A1 | 7/2010 | Kamen et al. |
| 2010/0198034 A1 | 8/2010 | Thomas et al. |
| 2010/0198182 A1 | 8/2010 | Lanigan et al. |
| 2010/0198183 A1 | 8/2010 | Lanigan et al. |
| 2010/0211002 A1 | 8/2010 | Davis |
| 2010/0212407 A1 | 8/2010 | Stringham et al. |
| 2010/0212675 A1 | 8/2010 | Walling et al. |
| 2010/0214110 A1 | 8/2010 | Wang et al. |
| 2010/0217154 A1 | 8/2010 | Deshmukh et al. |
| 2010/0217621 A1 | 8/2010 | Schoenberg |
| 2010/0271479 A1 | 10/2010 | Heydlauf |
| 2010/0273738 A1 | 10/2010 | Valcke et al. |
| 2010/0292634 A1 | 11/2010 | Kircher |
| 2010/0295686 A1 | 11/2010 | Sloan et al. |
| 2010/0298765 A1 | 11/2010 | Budiman et al. |
| 2010/0317093 A1 | 12/2010 | Turewicz et al. |
| 2010/0318025 A1 | 12/2010 | John |
| 2011/0000560 A1 | 1/2011 | Miller et al. |
| 2011/0001605 A1 | 1/2011 | Kiani et al. |
| 2011/0004186 A1 | 1/2011 | Butterfield |
| 2011/0009797 A1 | 1/2011 | Kelly et al. |
| 2011/0028885 A1 | 2/2011 | Eggers et al. |
| 2011/0040247 A1 | 2/2011 | Mandro et al. |
| 2011/0046558 A1 | 2/2011 | Gravesen et al. |
| 2011/0062703 A1 | 3/2011 | Lopez et al. |
| 2011/0064612 A1 | 3/2011 | Franzoni et al. |
| 2011/0071464 A1 | 3/2011 | Palerm |
| 2011/0072379 A1 | 3/2011 | Gannon |
| 2011/0077480 A1 | 3/2011 | Bloom et al. |
| 2011/0078608 A1 | 3/2011 | Gannon et al. |
| 2011/0099313 A1 | 4/2011 | Bolanowski |
| 2011/0105983 A1 | 5/2011 | Kelly et al. |
| 2011/0137241 A1 | 6/2011 | DelCastilio et al. |
| 2011/0144595 A1 | 6/2011 | Cheng |
| 2011/0160649 A1 | 6/2011 | Pan |
| 2011/0162647 A1 | 7/2011 | Huby et al. |
| 2011/0172918 A1 | 7/2011 | Tome |
| 2011/0175728 A1 | 7/2011 | Baker, Jr. |
| 2011/0190598 A1 | 8/2011 | Shusterman |
| 2011/0190694 A1 | 8/2011 | Lanier et al. |
| 2011/0238013 A1* | 9/2011 | Wang .............. A61M 5/365 604/123 |
| 2011/0264006 A1 | 10/2011 | Ali et al. |
| 2011/0264043 A1 | 10/2011 | Kotnick et al. |
| 2011/0282321 A1 | 11/2011 | Steil et al. |
| 2011/0320049 A1 | 12/2011 | Chossat et al. |
| 2012/0025995 A1 | 2/2012 | Moberg et al. |
| 2012/0035535 A1 | 2/2012 | Johnson et al. |
| 2012/0059234 A1 | 3/2012 | Barrett et al. |
| 2012/0068001 A1 | 3/2012 | Pushkarsky et al. |
| 2012/0095433 A1 | 4/2012 | Hungerford et al. |
| 2012/0123322 A1 | 5/2012 | Scarpaci et al. |
| 2012/0143116 A1 | 6/2012 | Ware et al. |
| 2012/0180790 A1 | 7/2012 | Montgomery |
| 2012/0185267 A1 | 7/2012 | Kamen et al. |
| 2012/0191059 A1 | 7/2012 | Cummings et al. |
| 2012/0194341 A1 | 8/2012 | Peichel et al. |
| 2012/0203177 A1 | 8/2012 | Lanier |
| 2012/0226350 A1 | 9/2012 | Rudser et al. |
| 2012/0245525 A1 | 9/2012 | Pope et al. |
| 2012/0259278 A1 | 10/2012 | Hayes et al. |
| 2013/0006666 A1 | 1/2013 | Schneider |
| 2013/0009551 A1 | 1/2013 | Knapp |
| 2013/0012917 A1 | 1/2013 | Miller et al. |
| 2013/0041342 A1 | 2/2013 | Bernini et al. |
| 2013/0083191 A1 | 4/2013 | Lowery et al. |
| 2013/0085443 A1 | 4/2013 | Lowery et al. |
| 2013/0085689 A1 | 4/2013 | Sur et al. |
| 2013/0110538 A1 | 5/2013 | Butterfield et al. |
| 2013/0150766 A1 | 6/2013 | Olde et al. |
| 2013/0150821 A1 | 6/2013 | Bollish et al. |
| 2013/0158504 A1 | 6/2013 | Ruchti et al. |
| 2013/0201482 A1 | 8/2013 | Munro |
| 2013/0116649 A1 | 9/2013 | Kouyoumjian et al. |
| 2013/0253430 A1 | 9/2013 | Kouyoumjian et al. |
| 2013/0261993 A1 | 10/2013 | Ruchti et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0318158 A1 | 11/2013 | Teng et al. |
| 2013/0345658 A1 | 12/2013 | Browne et al. |
| 2013/0345666 A1 | 12/2013 | Panduro et al. |
| 2014/0039446 A1 | 2/2014 | Day |
| 2014/0224829 A1 | 8/2014 | Capone et al. |
| 2014/0267563 A1 | 9/2014 | Baca et al. |
| 2014/0358077 A1 | 12/2014 | Oruklu et al. |
| 2015/0025453 A1 | 1/2015 | Ledford et al. |
| 2015/0033073 A1 | 1/2015 | Yang et al. |
| 2015/0168958 A1 | 6/2015 | Downie et al. |
| 2015/0246175 A1 | 9/2015 | Shubinsky et al. |
| 2015/0343141 A1 | 12/2015 | Lindo et al. |
| 2016/0042264 A1 | 2/2016 | Borges et al. |
| 2016/0103960 A1 | 4/2016 | Hume et al. |
| 2016/0110088 A1 | 4/2016 | Vik et al. |
| 2016/0151560 A1 | 6/2016 | Toro et al. |
| 2016/0151562 A1 | 6/2016 | Magers et al. |
| 2016/0175517 A1 | 6/2016 | Sileika et al. |
| 2016/0193604 A1 | 7/2016 | McFarland et al. |
| 2016/0256622 A1 | 9/2016 | Day et al. |
| 2017/0043089 A1 | 2/2017 | Handler |
| 2018/0028749 A1 | 2/2018 | Dumas, III et al. |

FOREIGN PATENT DOCUMENTS

| | | |
|---|---|---|
| DE | 31 12 762 | 1/1983 |
| DE | 34 35 647 | 7/1985 |
| DE | 35 30 747 | 3/1987 |
| DE | 37 20 664 | 1/1989 |
| DE | 38 27 444 | 2/1990 |
| DE | 197 34 002 | 9/1998 |
| DE | 199 01 078 | 2/2000 |
| DE | 198 40 965 | 3/2000 |
| DE | 198 44 252 | 3/2000 |
| DE | 199 32 147 | 1/2001 |
| DE | 102 49 238 | 5/2004 |
| DE | 103 52 456 | 7/2005 |
| EP | 0 282 323 | 9/1988 |
| EP | 0 291 727 | 11/1988 |
| EP | 0 319 272 | 6/1989 |
| EP | 0 319 275 | 6/1989 |
| EP | 0 335 385 | 10/1989 |
| EP | 0 337 092 | 10/1989 |
| EP | 0 341 582 | 11/1989 |
| EP | 0 370 162 | 5/1990 |
| EP | 0 387 724 | 9/1990 |
| EP | 0 429 866 | 6/1991 |
| EP | 0 441 323 | 8/1991 |
| EP | 0 453 211 | 10/1991 |

(56) References Cited

FOREIGN PATENT DOCUMENTS

| | | |
|---|---|---|
| EP | 0 462 405 | 12/1991 |
| EP | 0 501 234 | 9/1992 |
| EP | 0 516 130 | 12/1992 |
| EP | 0 519 765 | 12/1992 |
| EP | 0 643 301 | 3/1995 |
| EP | 0 683 465 | 11/1995 |
| EP | 0 431 310 | 1/1996 |
| EP | 0 589 439 | 8/1998 |
| EP | 0 880 936 | 12/1998 |
| EP | 0 954 090 | 11/1999 |
| EP | 0 960 627 | 12/1999 |
| EP | 1 174 817 | 1/2002 |
| EP | 1 177 802 | 2/2002 |
| EP | 1 197 178 | 4/2002 |
| EP | 1 500 025 | 4/2003 |
| EP | 1 813 188 | 8/2007 |
| EP | 2 062 527 | 5/2009 |
| EP | 2 228 004 | 9/2010 |
| EP | 2 243 506 | 10/2010 |
| EP | 2 381 260 | 10/2011 |
| ES | 254513 | 10/1981 |
| FR | 2 717 919 | 9/1995 |
| GB | 2 121 971 | 1/1984 |
| GB | 2 303 706 | 2/1997 |
| GB | 2 312 022 | 10/1997 |
| GB | 2 312 046 | 10/1997 |
| JP | 01-301118 | 12/1989 |
| JP | 01-308568 | 12/1989 |
| JP | 04-231966 | 8/1992 |
| JP | 07-289638 | 11/1995 |
| JP | 11-128344 | 5/1999 |
| JP | 2000-111374 | 4/2000 |
| JP | 2000-510575 | 8/2000 |
| JP | 2001-356034 | 12/2001 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2008-249400 | 10/2008 |
| JP | 4322661 | 6/2009 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/050526 | 6/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/026420 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2010/017279 | 2/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/135646 | 11/2010 |
| WO | WO 2010/135654 | 11/2010 |
| WO | WO 2010/135670 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |
| WO | WO 2011/109774 | 9/2011 |
| WO | WO 2012/042763 | 4/2012 |
| WO | WO 2013/028524 | 2/2013 |
| WO | WO 2013/096769 | 6/2013 |
| WO | WO 2014/004216 | 1/2014 |
| WO | WO 2015/134478 | 9/2015 |
| WO | WO 2017/051271 | 3/2017 |
| WO | WO 2017/197024 | 11/2017 |

OTHER PUBLICATIONS

Allegro, "3955—Full-Bridge PWM Microstepping Motor Drive", Datasheet, 1997, pp. 16.

Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.

Baxter, "Baxter Receives 510(k) Clearance for Next-Generation SIGMA Spectrum Infusion Pump with Master Drug Library" Press Release, May 8, 2014, pp. 2. http://web.archive.org/web/20160403140025/http://www.baxter.com/news-media/newsrom/press-releases/2014/05_08_14_sigma.page.

Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.

(56) References Cited

OTHER PUBLICATIONS

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.
Bode et al., "Intravenous Insulin Infusion Therapy: Indications, Methods, and Transition to Subcutaneous Insulin Therapy", Endocrine Practice, Mar./Apr. 2004, vol. 10, Supplement 2, pp. 71-80.
Cannon, MD et al., "Automated Heparin-Delivery System to Control Activated Partial Thromboplastin Time", Circulation, Feb. 16, 1999, vol. 99, pp. 751-756.
"CareAware® Infusion Management", Cerner Store, as printed May 12, 2011, pp. 3, https://store.cerner.com/items/7.
Chen et al., "Enabling Location-Based Services on Wireless LANs", The 11th IEEE International Conference on Networks, ICON 2003, Sep. 28-Oct. 1, 2003, pp. 567-572.
Cheung et al., "Hyperglycemia is Associated with Adverse Outcomes in Patients Receiving Total Parenteral Nutrition", Diabetes Care, Oct. 2005, vol. 28, No. 10, pp. 2367-2371.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Goldberg et al., "Clinical Results of an Updated Insulin Infusion Protocol in Critically Ill Patients", Diabetes Spectrum, 2005, vol. 18, No. 3, pp. 188-191.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hospira, "Plum A+™ Infusion System" as archived Dec. 1, 2012, pp. 2. www.hospira.com/products_and_services/infusion_pumps/plum/index.
Hospira, "Plum XL™ Series Infusion System" Technical Service Manual, Feb. 2005, Lake Forest, Illinois, USA, pp. i-vii, 5-14, 8-3.
International Preliminary Report on Patentability and Written Opinion received in PCT Application No. PCT/US2014/039347, dated Dec. 3, 2015 in 8 pages.
International Search Report and Written Opinion received in PCT Application No. PCT/US2014/039347, dated Oct. 16, 2014 in 9 pages.
Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.
Magaji et al., "Inpatient Management of Hyperglycemia and Diabetes", Clinical Diabetes, 2011, vol. 29, No. 1, pp. 3-9.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.
Microchip Technology Inc., "MTA11200B; TrueGauge™ Intelligent Battery Management I.C.", https://www.elektronik.ropla.eu/pdf/stock/mcp/mta11200b.pdf, 1995, pp. 44.
Moghissi, Etie, MD, FACP, FACE, "Hyperglycemia in Hospitalized Patients", A Supplement to ACP Hospitalist, Jun. 15, 2008, pp. 32.
Nuckols et al., "Programmable Infusion Pumps in ICUs: An Analysis of Corresponding Adverse Drug Events", Journal of General Internal Medicine, 2007, vol. 23, Supp. 1, pp. 41-45.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
SGS-Thomson Microelectronics, "L6219—Stepper Motor Drive", Datasheet, Dec. 1996, pp. 10.
SGS-Thomson Microelectronics, "PBL3717A—Stepper Motor Drive", Datasheet, Apr. 1993, pp. 11.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Smith, Joe, "Infusion Pump Informatics", CatalyzeCare: Transforming Healthcare, as printed May 12, 2011, pp. 2.
Tang et al., "Linear Dimensionality Reduction Using Relevance Weighted LDA", Pattern Recognition, 2005, vol. 38, pp. 485-493, http://staff.ustc.edu.cn/~ketang/papers/TangSuganYaoQin_PR04.pdf.
Thomas et al., "Implementation of a Tight Glycaemic Control Protocol Using a Web-Based Insulin Dose Calculator", Anaesthesia, 2005, vol. 60, pp. 1093-1100.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Westbrook et al., "Errors in the Administration of Intravenous Medications in Hospital and the Role of Correct Procedures and Nurse Experience", BMJ Quality & Safety, 2011, vol. 20, pp. 1027-1034.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
Alaris® Medical Systems, "Signature Edition® GOLD—Single & Dual Channel Infusion System", San Diego, CA, USA, date unknown, but believed to be at least as early as Nov. 29, 2008, pp. 70-74, 2-88 & 2-91.
Buhrdorf et al., "Capacitive Micromachined Ultrasonic Transducers and their Application", Proceedings of the IEEE Ultrasonics Symposium, Feb. 2001, vol. 2, pp. 933-940.
Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.
"Continually vs Continuously", https://web.archive.org/web/20090813092423/http://www.diffen.com/difference/Continually_vs_Continuously, as accessed Aug. 13 2009 in 4 pages.
"CritiCore® Monitor: Critical Fluid Output and Core Bladder Temperature Monitor", BARD Urological Catheter Systems, Advertisement, 2005, pp. 2.
"Differential Pressure Transmitter, Series PD-39 X", SensorsOne Ltd., Advertisement, Dec. 2005, pp. 2.
Dunster et al., "Flow Continuity of Infusion Systems at Low Flow Rates", Anaesthesia and Intensive Care, Oct. 1995, vol. 23, No. 5, pp. 5.
"Froth", http://www.merriam-webster.com/dictionary/froth, as accessed May 13, 2015 in 1 page.
Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.
Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.

(56) References Cited

OTHER PUBLICATIONS

JMS Co., Ltd., "Infusion Pump: OT-701", Tokyo, Japan, 2002, pp. 4.

Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology vol. 6, No. 6, pp. 1413-1419.

Kutcher et al., "The Effect of Lighting Conditions on Caries Interpretation with a Laptop Computer in a Clinical Setting", Elsevier, Oct. 2006, vol. 102, No. 4, pp. 537-543.

Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.

Merry et al., "A New, Safety-Oriented, Integrated Drug Administration and Automated Anesthesia Record System", Anesthesia & Analgesia, Aug. 2001, vol. 93, No. 2 pp. 385-390.

\* cited by examiner

MULTI-SENSOR INFUSION SYSTEM FOR DETECTING AIR OR AN OCCLUSION IN THE INFUSION SYSTEM

FIELD OF THE DISCLOSURE

This disclosure relates to detection systems and methods for detecting air or occlusions in an infusion system.

BACKGROUND

Existing strategies for detecting air in the line of an infusion device often involve the use of ultrasonic sensors that are physically located on opposite sides of a tubing segment. When fluid is present in the tube, propagation of the acoustic signal is efficient and produces a large electrical signal via the receiver circuit. On the other hand, the presence of air in the tube causes an acoustical open circuit which substantially attenuates the detected signal. In current practice, detection of air in the tubing segment is performed on the basis of a simple (static) air-fluid boundary or threshold that is applied to the sensor voltage signal. When the air sensor signal moves beyond the pre-defined air/fluid threshold, an alarm condition occurs and the IV infusion is paused.

Additionally, in current practice, there exist methods/algorithms that utilize the plunger force sensor readings to detect the presence of air in the plunger chamber. Several Hospira™ pumps involve the use of a cassette with a chamber that is compressed by an actuated plunger to pump fluid at a controlled rate from the drug container to the patient. The measured force during a pumping cycle is directly related to the type of fluid in the chamber. For instance, fluids are relatively incompressible and generate a higher and different force profile than air. Similarly, a combination of fluid and air in the chamber results in a hybrid force profile that is indicative of the mixture percentages.

Both methods described above rely on observations from a single sensor (i.e., air sensor or force sensor). Faulty sensor observations are the major drawback of such single-sensor based systems/algorithms. For instance, for air sensor based algorithms, a variety of situations (e.g., dancing micro air bubbles, stuck fluid droplet at the end-of-bag, etc.) exist which generate false alarms or mask the presence of air in front of the air-sensor leading to false negatives. Similarly, force sensor based algorithms can be fooled by variable distal/proximal pressure during delivery (e.g., kinked tubing due to patient movement). The measured force during a pumping cycle is affected by the pressure applied to both distal and proximal sides of the tubing. For instance, drop in a distal pressure will cause drop in the plunger force readings, which will be perceived as a transition from fluid to air in the chamber by the existing force algorithms and cause a false positive detection of air. Single-sensor based air-in-line detection systems ma y fail to detect an end-of-bag situation that can result in air in the line, or may incorrectly determine that the fluid in the line is air (i.e., causing nuisance alarms).

A system and method is needed to overcome one or more issues of one or more of the existing infusion systems or methods.

SUMMARY

In one embodiment, an infusion system is disclosed for being operatively connected to a fluid delivery line and to an infusion container containing an infusion fluid. The infusion system includes a pump, a plurality of different types of sensors connected to the pump or the fluid delivery line, at least one processor, and a memory. The plurality of different types of sensors are configured to indicate whether air is in the fluid delivery line. The at least one processor is in electronic communication with the pump and the plurality of different types of sensors. The memory is in electronic communication with the at least one processor. The memory includes programming code for execution by the at least one processor. The programming code is configured to, based on measurements taken by the plurality of different types of sensors, determine the following: (1) whether there is air in the fluid delivery line; (2) whether there is a partial occlusion or a total occlusion in the fluid delivery line; or (3) a percentage of the air present in the fluid delivery line or the probability of the air being in the fluid delivery line.

In another embodiment, a method for infusing an infusion fluid is disclosed. In one step, infusion fluid is pumped through a fluid delivery line of an infusion system. In another step, measurements are taken with a plurality of different types of sensors connected to the infusion system. In an additional step, at least one processor determines, based on the measurements taken by the plurality of the different types of the sensors, the following: (1) whether there is air in the fluid delivery line; (2) whether there is a partial occlusion or a total occlusion in the fluid delivery line; or (3) a percentage of the air present in the fluid delivery line or the probability of the air being in the fluid delivery line.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
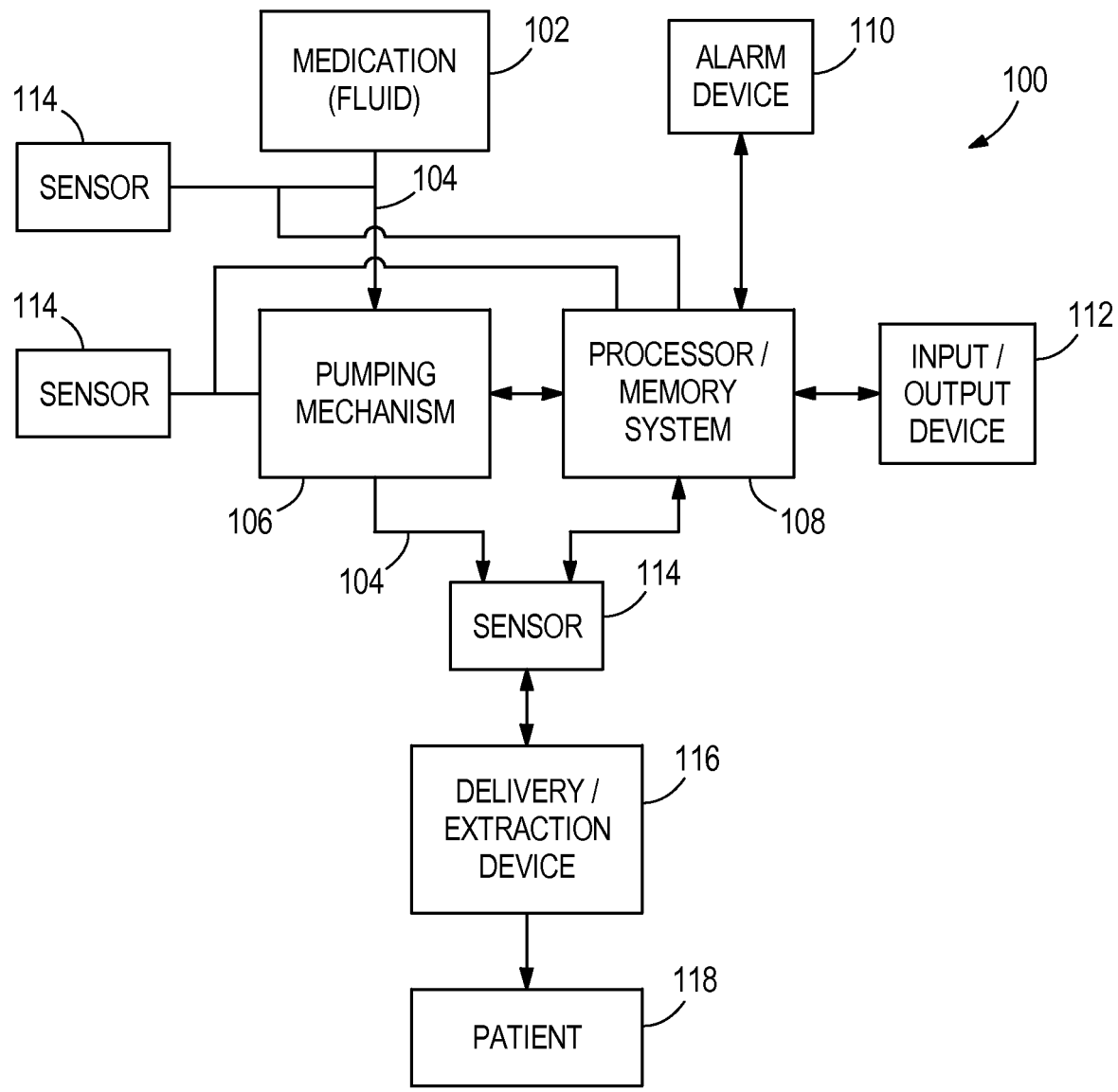
FIG. 1 illustrates a block diagram of one embodiment of an infusion system.

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims. It is noted that the Figures are purely for illustrative purposes and are not to scale.

In this disclosure, multi-sensor algorithms that utilize signals from at least two different sensors, such as air, force, and pressure sensors, are utilized. Further, methods are disclosed of combining and qualifying the signals from multi-sensors to improve the robustness and reliability (i.e., true negative and false positive performance) of air detection systems.

The disclosure is a software based solution for detecting the presence of air within a fluid delivery line. The target application is an air-in-line and end-of-bag detection system for IV medication infusion pumps (e.g., Symbig™, Gemstar™, or Plum™).

In the disclosure signals from multiple-sensors (i.e., acoustic air sensor, force sensor, distal and proximal pressure sensors) are integrated in order to improve the robustness, and the true negative and false positive performance of IV infusion air-in-line detection systems. Disclosed herein are methods of combining and qualifying the signals from multi-sensors to improve the reliability of air detection systems.

In an alternate embodiment, the disclosure can be used to fully characterize the type of fluid-air mixture present in the infusion line by using multiple-sensor signals to determine the percent of air present or the probability of the presence of air. In another alternate embodiment, the disclosure can be used to improve the robustness and reliability of occlusion detection systems by combining and qualifying the signals from multi-sensors.

The following is a summary of some distinguishing elements of this disclosure. An event detection and qualifier algorithm is disclosed which determines the presence of air in the line during delivery on the basis of air sensor and plunger force sensor observations. An event detection and qualifier algorithm is disclosed that determines the presence of air in the line during delivery on the basis of air sensor, plunger force sensor, and distal and proximal pressure sensor observations. An event detection and qualifier algorithm is disclosed that determines the presence of a partial or total distal/proximal occlusion in the fluid delivery line on the basis of plunger force and pressure sensor signals. A multivariate pattern recognition system is disclosed which determines the percent of air present or the probability of the presence of air in the line.

One problem addressed in this disclosure is to integrate signals from multi-sensors in order to improve the robustness, and the true negative and false positive performance of IV infusion air-in-line detection systems. Disclosed herein are methods of combining and qualifying the signals from multi-sensors to improve the reliability of air detection systems.

Another problem addressed in this disclosure is to fully characterize the type of fluid/air mixture present in the infusion line. Disclosed herein are methods that integrate signals from multi-sensors in order to determine t h e probability or the percent of air present in the line.

Still another problem addressed in this disclosure is the detection of partial and total distal/proximal occlusion in the fluid delivery line. Disclosed herein are methods of combining and qualifying the signals from multi-sensors to improve the robustness and reliability of occlusion detection systems. In current practice, distal/proximal occlusion algorithms are typically based on pressure readings only.

The disclosure improves the air detection capability of existing infusion pump systems that rely on sensors to make a real-time assessment. In doing so, the disclosed methods do not require additional hardware modifications but instead leverage the acquired multi-sensor signals. Additionally, the disclosure does not necessarily replace existing software modules for air detection but adds an additional safety layer.

The disclosure provides a method for improving the robustness of air detection systems by reducing the likelihood of a false positive air detection. This reduces the chances of an interruption of therapy due to a false alarm. The disclosure further provides a means to improve the sensitivity and specificity of air detection by fusing data collected by multiple sensors.

In current practice, air-in-line algorithms are typically based on air sensor signals only and are used to signify the presence of a single bubble, froth, stuck droplet, or cumulative air in the fluid delivery line. Similarly, plunger force algorithms that are based on plunger force signal only, are typically used to signify the presence of air in the plunger chamber. In this disclosure, plunger force algorithms are integrated with air-in-line algorithms to provide a more robust air-in-line detection system with improved true negative and false positive performance.

There is a delay between force and air sensor readings due to the physical location of the two sensors. For instance, for a Symbig™ pump, the force sensor is located on the plunger and the air sensor is located distal to the plunger, and the fluid volume between the two sensors is approximately 150 µL (or 2 full plunger strokes). The integrated system disclosed herein utilizes both force and air sensor signals to account for such delays.

FIG. 1 illustrates a block diagram of an infusion system 100 under one embodiment of the disclosure. The infusion system 100 comprises: an infusion container 102; a fluid delivery line 104; a pump device 106; a processing device 108; an alarm device 110 that generates an audio, visual, or other sensory signal or the like to a user; an input/output device 112; a plurality of different types of sensors 114; and a delivery/extraction device 116. The infusion system 100 may comprise an infusion system such as the Plum™, Gemstar™, Symbig™, or other type of infusion system.

The infusion container 102 comprises a container for delivering an infusion fluid such as IV fluid or a drug to a patient 118. The fluid delivery line 104 comprises one or more tubes, connected between the infusion container 102, the pump device 106, the plurality of different types of sensors 114, and the delivery/extraction device 116, for transporting infusion fluid from the infusion container 102, through the pump device 106, through the plurality of different types of sensors 114, through the delivery/extraction device 116 to the patient 118. The fluid delivery line 104 may also be used to transport blood, delivered to or extracted from the patient 118 using the delivery/extraction device 116, through the plurality of different types of sensors 114 as a result of a pumping action of the pump device 106. The pump device 106 comprises a pump for pumping infusion fluid from the infusion container 102 or for pumping blood to or from the patient 118. The pump device 106 may comprise a plunger based pump, a peristaltic pump, or another type of pump.

The processing device 108 comprises at least one processor for processing information received from the plurality of different types of sensors 114 and for executing one or more algorithms to determine: (1) whether there is air in the fluid delivery line 104; (2) whether there is a partial or total occlusion in the fluid delivery line 104; (3) or a percentage of air present in the fluid delivery line 104 or the probability of the air being in the fluid delivery line 104. The processing device 108 includes or is in electronic communication with a computer readable memory, containing programming code containing the one or more algorithms for execution by the processor, and a clock. The alarm device 110 comprises an alarm, triggered by the processing device 108, for notifying the clinician (also referred to as 'user' herein) of: (1) whether there is air in the fluid delivery line 104; (2) whether there is a partial or total occlusion in the fluid delivery line 104; (3) or a percentage of air present in the fluid delivery line 104 or the probability of the air being in the fluid delivery line 104. The alarm device 110 may be configured to stop the pump device 106 prior to a significant amount of air being delivered through the fluid delivery line 104 and the delivery/extraction device 116 to the patient 118.

The input/output device 112 comprises a device which allows a clinician to input or receive information. The input/output device 112 allows a clinician to input information such as: medication information regarding the infusion fluid being delivered from the infusion container 102; infusion information regarding the infusion of the infusion fluid being delivered from the infusion container 102; distance information regarding the distance(s) between the plurality of different type of sensors; delay information regarding the delay(s) in measurements between the plurality of different types of sensors 114; the selection of settings for the processing device 108 to apply in using the programming code containing the algorithm(s); or other information that is pertinent to the infusion. The medication information regarding the infusion fluid delivered from the infusion container 102 may comprise a formulation of the infusion fluid, a rate of the infusion fluid, a duration of the infusion fluid, a viscosity of the infusion fluid, a therapy of the infusion fluid, or a property of the infusion fluid. The infusion information regarding the infusion fluid delivered from the infusion container 102 may comprise a volume of the infusion fluid in the infusion container or another parameter regarding the infusion of the infusion fluid. The input/output device 112 may allow a clinician to select and/or confirm a user-inputted medication infusion program to be applied by the processing device 108. The input/output device 112 may further output information to the clinician. In other embodiments, any of the information inputted into the input/output device 112 may be pre-installed into the programming code or the processing device 108.

The plurality of different types of sensors 114 may comprise any number, combination, or configuration of pressure sensors, force sensors, air sensors, or other type of sensors. The pressure sensors may comprise one or more proximal or distal pressure sensors for detecting the amount of pressure in the fluid delivery line 104 proximal or distal to the pump device 106. The amount of pressure detected by the one or more pressure sensors is indicative of whether air, fluid, or some combination thereof is present in the fluid delivery line 104. For instance, U.S. Pat. No. 8,403,908 to Jacobson et al., which is commonly owned and hereby incorporated by reference, discloses the use of pressure sensors to determine whether air, fluid, or some combination thereof is present in the fluid delivery line 104. The one or more force sensors may comprise one or more force sensors for detecting the amount of force on a plunger of the pump device 106. The amount of force detected by the one or more force sensors is indicative of whether air, fluid, or some combination thereof is present in the fluid delivery line 104. For instance, U.S. Ser. No. 13/851,207 filed 27 Mar. 2013, which is commonly owned and hereby incorporated by reference, discloses the use of force sensors to determine whether air, fluid, or some combination thereof is present in the fluid delivery line 104. The one or more air sensors may comprise one or more air sensors for detecting whether air, fluid, or a combination thereof is present in the fluid delivery line 104. The strength of the signal that propagates from the one or more air sensors through the fluid delivery line 104 is indicative of whether air, fluid, or some combination thereof is present in the fluid delivery line 104. For instance, U.S. Pat. No. 7,981,082 to Wang et al., which is commonly owned and hereby incorporated by reference, discloses the use of air sensors to determine whether air, fluid, or some combination thereof is present in the fluid delivery line 104. In other embodiments, any number, types, combinations, or configurations of sensors 114 may be used to determine whether air, fluid, or some combination thereof is present in the fluid delivery line 104.

The delivery/extraction device 116 comprises a patient vascular access point device for delivering infusion fluid from the infusion container 102 to the patient 118, or for extracting blood from the patient 118. The delivery/extraction device 116 may comprise a needle, a catheter, a cannula, or another type of delivery/extraction device. In other embodiments, the infusion system 100 of FIG. 1 may be altered to vary the components, to take away one or more components, or to add one or more components.

Figure 2:
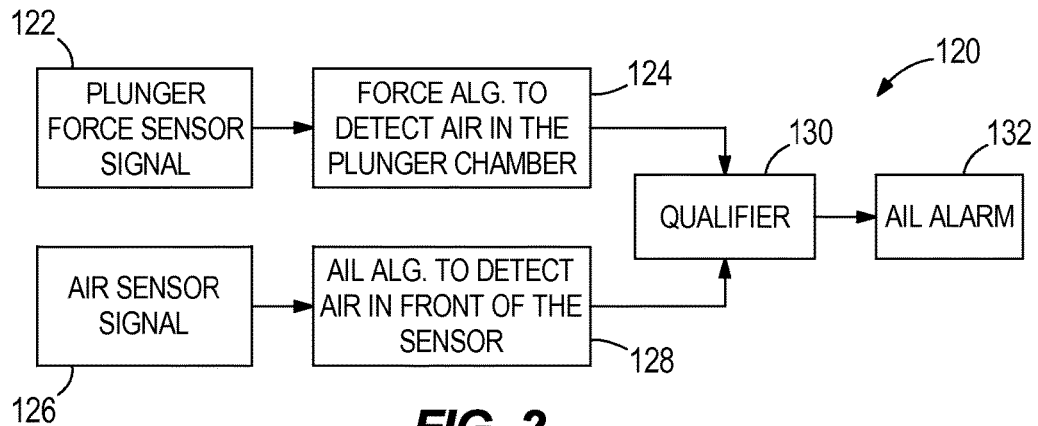
FIG. 2 illustrates a flowchart of one embodiment of a method for determining whether air is present in an infusion system.

FIG. 2 illustrates a flowchart of one embodiment of a method 120 for determining whether air is in an infusion system. The method 120 may utilize the system of FIG. 1. In other embodiments, the method 120 may utilize varying systems. In step 122, a force sensor determines how much force is acting upon a plunger or pumping member of a pump. In step 124, a force algorithm is applied using the force sensor measurements of step 122 in order to detect whether air is in a chamber of the pump based on the force sensor measurements. In step 126, an air sensor determines how much of a signal propagates through a fluid delivery line of the infusion system. In step 128, an air-in-line algorithm is applied using the air sensor measurements of step 126 in order to detect whether air is located in the fluid delivery line at the air sensor based on the air sensor measurements. In step 130, a single qualifier algorithm is applied which uses both the results of the application of the force algorithm in step 124 and the results of the application of the air-in-line algorithm of step 128 in order to determine whether air is in the infusion system. The qualifier algorithm of step 130 integrates the decisions of steps 124 and 128 which were based on the measurements of the force sensor and the air sensor and in doing so considers the delay between the force sensor and the air sensor which results due to the distance between them. In such manner, by considering the air results of different types of sensors at different locations a more accurate determination is made as to whether air is contained in the infusion system. In step 132, the alarm device turns on or generates an alarm if step 130 determines that air is in the infusion system. In other embodiments, the method 120 may be altered to vary the order or substance of any of the steps, to delete one or more steps, or to add one or more steps.

Figure 3:
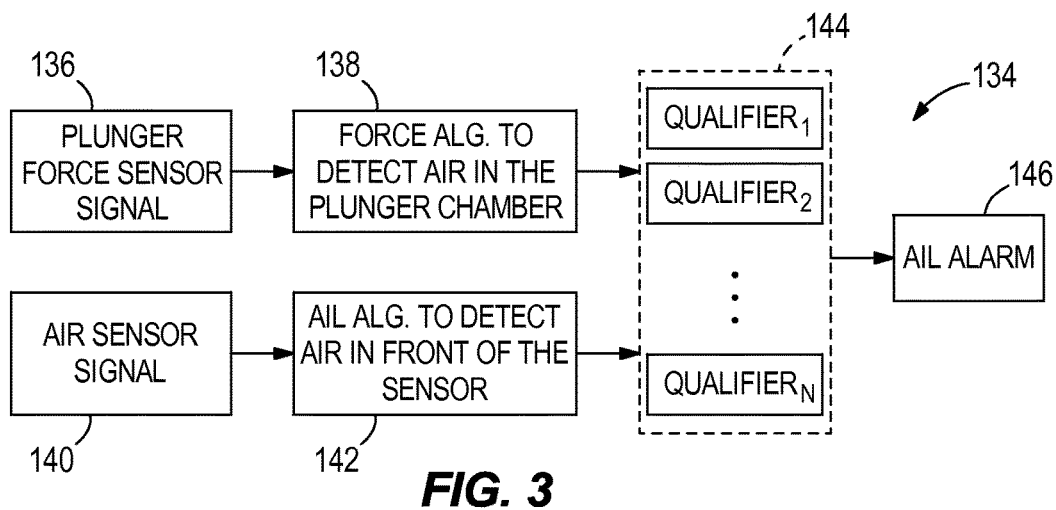
FIG. 3 illustrates a flowchart of another embodiment of a method for determining whether air is in an infusion system.

FIG. 3 illustrates a flowchart of another embodiment of a method 134 for determining whether air is in an infusion system. The method 134 may utilize the system of FIG. 1. In other embodiments, the method 134 may utilize varying systems. In step 136, a force sensor determines how much force is acting upon a plunger or pumping member of a pump. In step 138, a force algorithm is applied using the force sensor measurements of step 136 in order to detect whether air is in a chamber of the pump based on the force sensor measurements. In step 140, an air sensor determines how much of a signal propagates through a fluid delivery line of the infusion system. In step 142, an air-in-line algorithm is applied using the air sensor measurements of step 140 in order to detect whether air is located in the fluid delivery line at the air sensor based on the air sensor measurements. In step 144, multiple qualifier algorithms are applied which use both the results of the application of the force algorithm in step 138 and the results of the application of the air-in-line algorithm of step 142 in order to determine whether air is in the infusion system. The multiple qualifier algorithms of step 144 integrate the decisions of steps 138 and 142 which were based on the measurements of the force sensor and the air sensor and in doing so consider the delay between the force sensor and the air sensor which results due to the distance between them. In such manner, by considering the air results of different types of sensors at different locations a more accurate determination is made as to whether air is contained in the infusion system. In step 146, the alarm device generates or turns on an alarm if step 144 determines that air is in the infusion system. In other embodiments, the method 134 may be altered to vary the order or substance of any of the steps, to delete one or more steps, or to add one or more steps.

Figure 4:
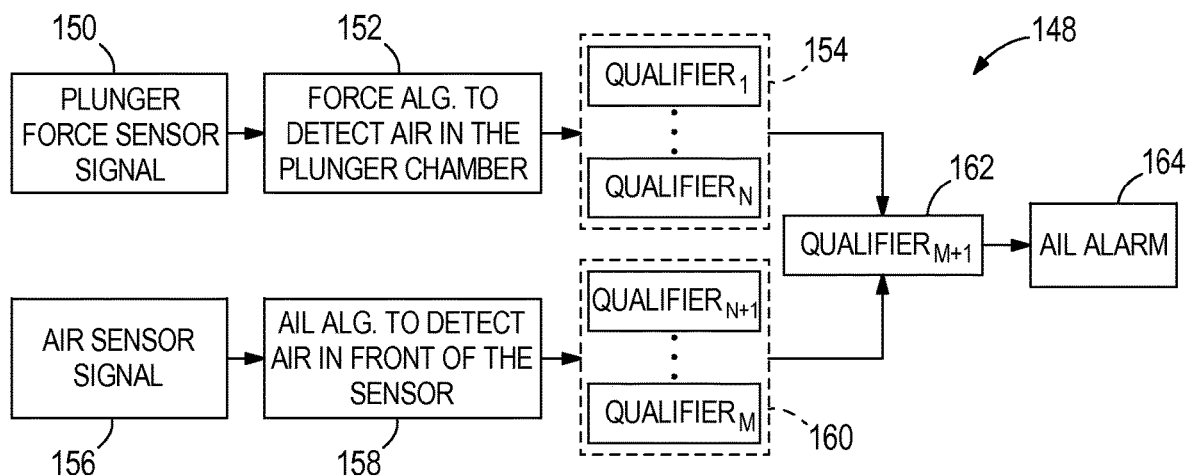
FIG. 4 illustrates a flowchart of still another embodiment of a method for determining whether air is in an infusion system.

FIG. 4 illustrates a flowchart of still another embodiment of a method 148 for determining whether air is in an infusion system. The method 148 may utilize the system of FIG. 1. In other embodiments, the method 148 may utilize varying systems. In step 150, a force sensor determines how much force is acting upon a plunger or pumping member of a pump. In step 152, a force algorithm is applied using the force sensor measurements of step 150 in order to detect whether air is in a chamber of the pump based on the force sensor measurements. In step 154, multiple qualifier algorithms are applied which use the results of the application of the force algorithm in step 152 in order to determine whether air is in the infusion system. In step 156, an air sensor determines how much of a signal propagates through a fluid delivery line of the infusion system. In step 158, an air-in-line algorithm is applied using the air sensor measurements of step 156 in order to detect whether air is located in the fluid delivery line at the air sensor based on the air sensor measurements. In step 160, multiple qualifier algorithms are applied which use the results of the application of the air-in-line algorithm in step 158 in order to determine whether air is in the infusion system. In step 162, a single qualifier algorithm is applied which uses both the results of the multiple qualifier algorithms of step 154 and the results of the multiple qualifier algorithms of step 160 in order to determine whether air is in the infusion system. The qualifier algorithm of step 162 integrates the decisions of steps 154 and 160 which were based on the measurements of the force sensor and the air sensor and in doing so considers the delay between the force sensor and the air sensor which results due to the distance between them. In such manner, by considering the air results of different types of sensors at different locations a more accurate determination is made as to whether air is contained in the infusion system. In step 164, the alarm device turns on or generates an alarm if step 162 determines that air is in the infusion system. In other embodiments, the method 148 may be altered to vary the order or substance of any of the steps, to delete one or more steps, or to add one or more steps.

Figure 5:
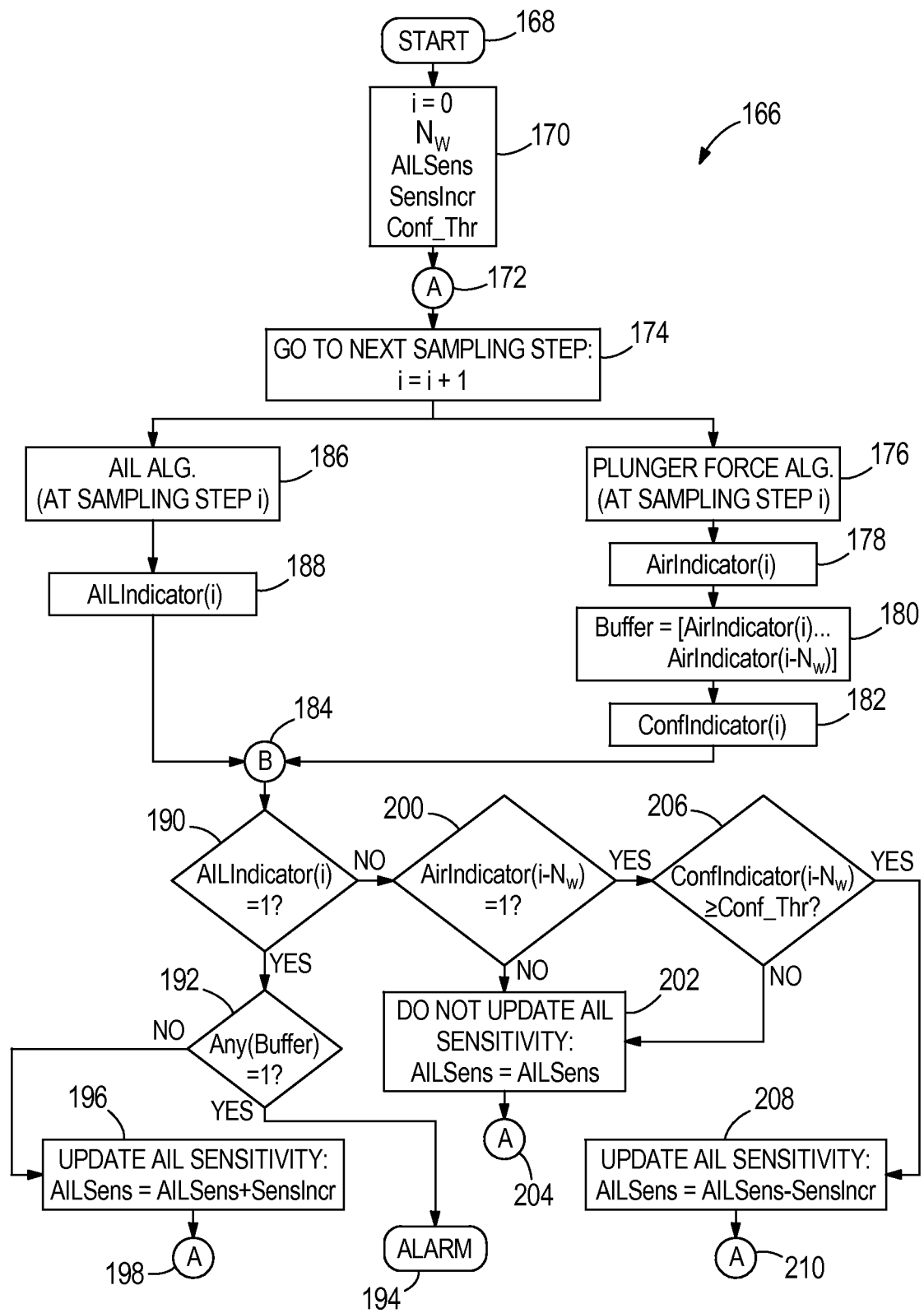
FIG. 5 illustrates a flowchart of another embodiment of a method for determining whether air is in an infusion system using both plunger force sensor readings and air-in-line sensor readings.

FIG. 5 illustrates a flowchart of another embodiment of a method 166 for determining whether air is in an infusion system using both plunger force sensor readings and air-in-line sensor readings. It can be applied to any air-in-line algorithm as long as it outputs an air-in-line indicator at each sampling step indicating whether air was detected in the line by the air-in-line sensor. Similarly, it can be applied to any force algorithm as long as it outputs an air indicator and a confidence indicator at each sampling step indicating whether air was detected in the line by the plunger force sensor and to what confidence level the air indicator based on the plunger force sensor determined that the air was present. The method 166 uses the force algorithm to adjust the sensitivity of the air-in-line algorithm during infusion (i.e. the sensitivity of the air-in-line algorithm is increased when the force algorithm detects air with high confidence and the air-in-line algorithm fails to detect the air; and the sensitivity of the air-in-line algorithm is decreased when the force algorithm does not detect air anywhere in a buffer and the air-in-line algorithm mistakenly detects the air). The method 166 takes into account delays between the air-in-line indicator and the air indicator which result from differences in locations of the air-in-line sensor and the plunger force sensor by utilizing a buffer that stores previous air indicators based on the plunger force sensor measurements. The method 166 may utilize the system of FIG. 1. In other embodiments, the method 166 may utilize varying systems.

In step 168, the method starts. The method proceeds from step 168 to step 170. In step 170, the variables are set including setting sampling step i=0, setting the number Nw of pumping strokes of delay between a plunger force sensor and an air-in-line sensor, setting the air-in-line sensitivity AILSens of the air-in-line sensor to an initial setting, setting the air-in-line sensitivity increment SensIncr of the air-in-line sensor to an initial setting, and setting the percent confidence threshold Conf_Thr to an initial setting. It is noted that throughout this disclosure that sampling step i represents one stroke of the pump of the infusion system. The method proceeds from step 170 through location step 172 to step 174. In step 174, sampling step i is reset to i=i+1. The method proceeds from step 174 to step 176.

In step 176, a plunger force algorithm is used to determine at sampling step i whether air is detected in a pumping chamber based on measurements of a plunger force sensor. The method proceeds from step 176 to step 178. In step 178, if air is detected in step 176 then an air indicator AirIndicator (i) is set to 1 and if air is not detected in step 176 then the air indicator AirIndicator(i) is set to 0. The method proceeds from step 178 to step 180. In step 180, a Buffer is saved as [AirIndicator(i) . . . AirIndicator(i−Nw)] saving the 1 or 0 setting made in step 178. For instance, if it takes 2 pumping strokes of the pump for the infusion fluid to travel from the plunger force sensor to the air-in-line sensor, then Nw is set to 2 to accommodate for this delay and the Buffer saves the AirIndicator(i) for the current sample i, the AirIndicator(i−1) for the previous sample i−1, and the AirIndicator(i−2) for two samples before. In step 182, a confidence indicator ConfIndicator(i) is set for the current sample i as to the percent confidence in the presence of air being present in the pumping chamber. The method proceeds from step 182 through location step 184 to step 190.

While the method proceeds from step 174 to 176, the method also simultaneously proceeds from step 174 to step 186. In step 186, an air-in-line algorithm is used to determine at sampling step i whether air is detected in a fluid-delivery-line of the infusion system based on measurements from the air-in-line sensor. The method proceeds from step 186 to step 188. In step 188, if air is detected in step 186 then an air-in-line AILIndicator(i) is set to 1 and if air is not detected in step 186 then the air-in-line AILIndicator(i) is set to 0. The method proceeds from step 188 through location step 184 to step 190.

In step 190, a determination is made as to whether the air-in-line indicator AILIndicator(i) equals 1. If a determination is made that the air-in-line indicator AILIndicator(i) does equal 1, then the method proceeds from step 190 to step 192. In step 192, if any of the buffer saved in step 180 is set to 1 (i.e. if any of AirIndicator(i) . . . AirIndicator(i−Nw) is set to 1), then the method proceeds from step 192 to step 194 and turns on the alarm indicating that air is disposed in the infusion system since both the air-in-line indicator (AILIndicator) and the plunger force indicator (AirIndicator) indicated that air was in the infusion system (i.e. AILIndicator(i)=1 and one or more of the entries saved in the AirIndicator buffer=1). When the alarm is turned on in step 194, the infusion system is turned off automatically or manually by the clinician to stop the infusion of the infusion fluid.

In step 192, if any of the buffer saved in step 180 is not set to 1 (i.e. if any of AirIndicator(i) . . . AirIndicator(i−Nw) is not set to 1), then the method proceeds from step 192 to step 196. In step 196, the air-in-line sensitivity AILSens is updated to decrease the sensitivity using the equation AILSens=AILSens+SensIncr. The air-in-line sensitivity is decreased in step 196 because air was detected by the air-in-line indicator AILIndicator (i.e. AILIndicator(i)=1) but air was not detected by the plunger force indicator AIRindicator (i.e. none of the entries in the AirIndicator buffer=1) which demonstrates that the air-in-line indicator AILIndicator caused a false positive. To increase the robustness of the air-detection system in step 196 the sensitivity of the air-in-line indicator is decreased to reduce the occurrence of false positives. It is noted that to decrease the air-in-line sensitivity in step 196 the AILSens is actually increased because the larger the AILSens is the less sensitive the algorithm will be causing it to only detect larger air-slugs. The method proceeds from step 196 through location step 198 though location step 172 to step 174 and repeats the process steps.

In step 190, if the air-in-line indicator AILIndicator(i) is not set to 1 the method proceeds from step 190 to step 200. In step 200, a determination is made whether AirIndicator (i−Nw) is set to 1 (i.e. whether the plunger force indicator Nw cycles ahead of the air-in-line detector determined that air was in the infusion system to accommodate for the delay between the plunger force sensor and the air-in-line sensor). If the determination is made in step 200 that the AirIndicator (i−Nw) is not set to 1 the method proceeds from step 200 to step 202. In step 202, the AIL Sensitivity is not updated (i.e. AILSens remains equal to AILSens since neither the air-in-line indicator (AILIndicator) nor the plunger force indicator (AirIndicator) indicated that air was in the infusion system). The method proceeds from step 202 through location step 204 through location step 172 to step 174 and repeats the process steps.

If the determination is made in step 200 that the AirIndicator(i−Nw) is set to 1 the method proceeds from step 200 to step 206. In step 206, a determination is made whether the confidence indicator ConfIndicator(i−Nw) of the force algorithm (indicating the confidence level that air has been detected in the infusion system by the plunger force sensor by applying the force algorithm Nw cycles ahead of the air-in-line sensor) is greater than or equal to the confidence threshold (Conf_Thr). If the determination is made in step 206 that the confidence indicator of the force algorithm is not greater than or equal to the confidence threshold, the method proceeds from step 206 to step 202. In step 202, the air-in-line sensitivity AILSens is not updated (i.e. AILSens remains equal to AILSens since the air-in-line indicator (AILIndicator) did not indicate that air was in the infusion system and the plunger force indicator (AirIndicator) only indicated with low confidence that air was in the infusion system). The method proceeds from step 202 through location step 204 through location step 172 to step 174 and repeats the process steps.

If the determination is made in step 206 that the confidence indicator ConfIndicator(i−Nw) of the force algorithm is greater than or equal to the confidence threshold Conf_Thr, the method proceeds from step 206 to step 208. In step 208, the air-in-line sensitivity is updated to increase the sensitivity using the equation AILSens=AILSens−SensIncr. The air-in-line sensitivity is increased in step 208 because air was not detected by the air-in-line indicator AILIndicator (i.e. AILIndicator(i) was not set to 1) but air was detected by the plunger force indicator AIRIndicator with a high confidence level (AirIndicator(i−Nw) was set to 1 and the ConfIndicator(i−Nw) was greater than or equal to Conf_Thr) which demonstrates that the air-in-line indicator AILIndicator was not sensitive enough and caused a missed air-in-line AILIndicator detection of air. To increase the robustness of the air-detection system in step 208 the sensitivity of the air-in-line indicator is increased to reduce the occurrence of missed positive detections of air in the infusion system. It is noted that to increase the air-in-line sensitivity in step 208 the AILSens is actually decreased because the smaller the AILSens is the more sensitive the algorithm will be causing it to detect smaller air-slugs. The method proceeds from step 208 through location step 210 through location step 172 to step 174 and repeats the process steps. In other embodiments, the method 166 may be altered to vary the order or substance of any of the steps, to delete one or more steps, or to add one or more steps.

Figure 6:
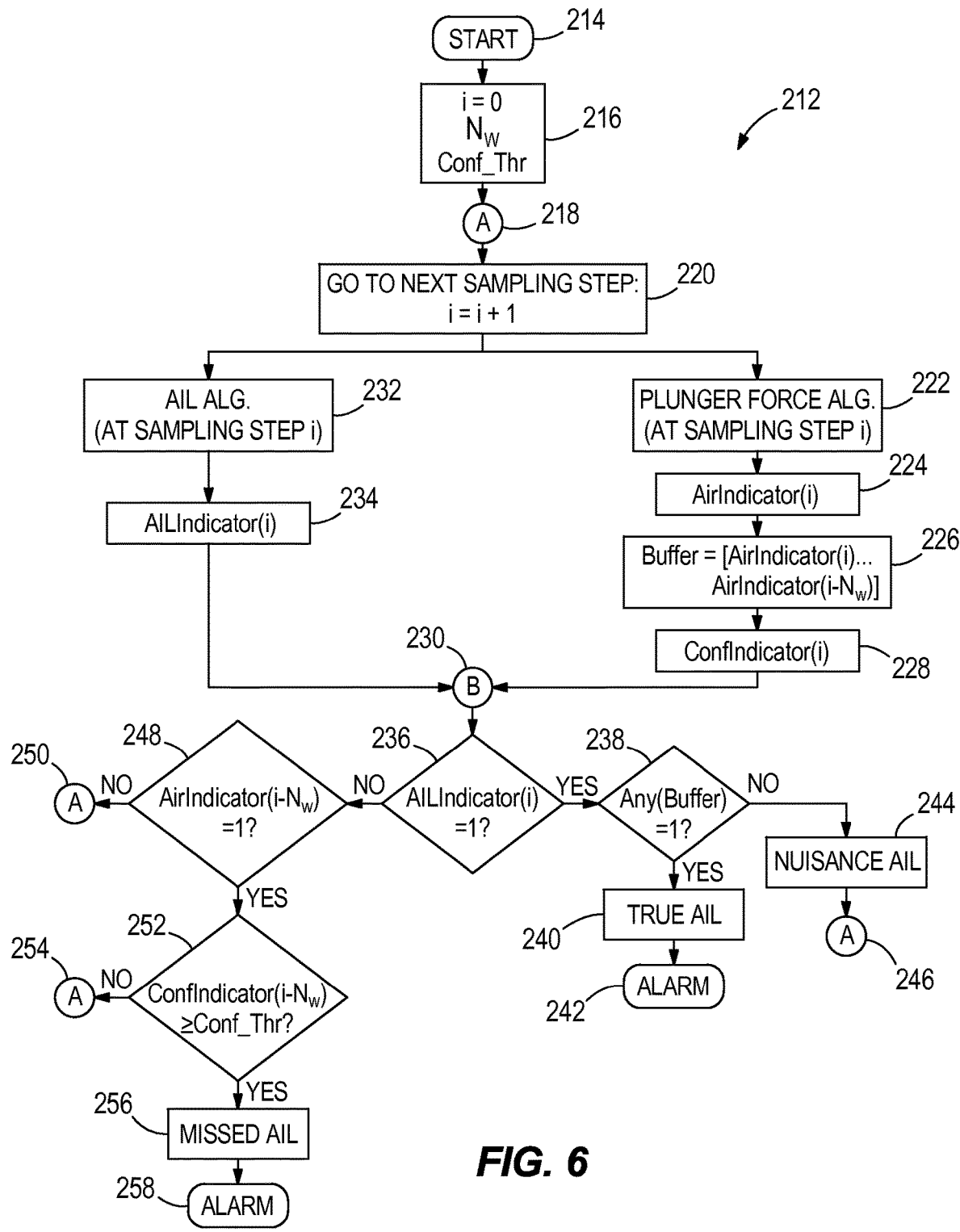
FIG. 6 illustrates a flowchart of another embodiment of a method for determining whether air is in an infusion system using both plunger force sensor readings and air-in-line sensor readings.

FIG. 6 illustrates a flowchart of another embodiment of a method 212 for determining whether air is in an infusion system using both plunger force sensor readings and air-in-line sensor readings. It can be applied to any air-in-line algorithm as long as it outputs an air-in-line indicator at each sampling step indicating whether air was detected in the line by the air-in-line sensor. Similarly, it can be applied to any force algorithm as long as it outputs an air indicator and a confidence indicator at each sampling step indicating whether air was detected in the line by the plunger force sensor and to what confidence level the air indicator based on the plunger force sensor determined that the air was present. The method 212 uses the force algorithm to declare true, missed, or nuisance/false air-in-line alarms. The method 212 takes into account delays between the air-in-line indicator and the air indicator which result from differences in locations of the air-in-line sensor and the plunger force sensor by utilizing a buffer that stores previous air indicators based on the plunger force sensor measurements. The method 212 may utilize the system of FIG. 1. In other embodiments, the method 212 may utilize varying systems.

In step 214, the method starts. The method proceeds from step 214 to step 216. In step 216, the variables are set including setting sampling step i=0, setting the number Nw of pumping strokes of delay between the plunger force sensor and an air-in-line sensor, and setting the percent confidence threshold Conf_Thr to an initial setting. The method proceeds from step 216 through location step 218 to step 220. In step 220, sampling step i is reset to i=i+1. The method proceeds from step 220 to step 222.

In step 222, a plunger force algorithm is used to determine at sampling step i whether air is detected in a pumping chamber based on measurements of a plunger force sensor. The method proceeds from step 222 to step 224. In step 224, if air is detected in step 222 then an air indicator AirIndicator(i) is set to 1 and if air is not detected in step 222 then the air indicator AirIndicator(i) is set to 0. The method proceeds from step 224 to step 226. In step 226, a Buffer is saved as [AirIndicator(i) . . . AirIndicator(i–Nw)] saving the 1 or 0 setting made in step 224. For instance, if it takes 2 pumping strokes of the pump for the infusion fluid to travel from the plunger force sensor to the air-in-line sensor, then Nw is set to 2 to accommodate for this delay and the Buffer saves the AirIndicator(i) for the current sample i, the AirIndicator(i–1) for the previous sample i–1, and the AirIndicator(i–2) for two samples before. In step 228, a confidence indicator ConfIndicator(i) is set for the current sample i as to the percent confidence in the presence of air being present in the pumping chamber. The method proceeds from step 228 through location step 230 to step 236.

While the method proceeds from step 220 to 222, the method also simultaneously proceeds from step 220 to step 232. In step 232, an air-in-line algorithm is used to determine at sampling step i whether air is detected in a fluid-delivery-line of the infusion system based on measurements from the air-in-line sensor. The method proceeds from step 232 to step 234. In step 234, if air is detected in step 232 then an air-in-line AILIndicator(i) is set to 1 and if air is not detected in step 232 then the air-in-line AILIndicator(i) is set to 0. The method proceeds from step 234 through location step 230 to step 236.

In step 236, a determination is made as to whether the air-in-line indicator AILIndicator(i) equals 1. If it is determined in step 236 that the air-in-line indicator AILIndicator (i) equals 1, the method proceeds from step 236 to step 238. In step 238, if any of the buffer saved in step 226 is set to 1 (i.e. if any of AirIndicator(i) . . . AirIndicator(i–Nw) is set to 1), the method proceeds from step 238 to step 240 and determines that there is air in the infusion system. The method proceeds from step 240 to step 242 and turns on the alarm indicating that air is disposed in the infusion system since both the air-in-line indicator (AILIndicator) and the plunger force indicator (AirIndicator) indicated that air was in the infusion system (i.e. AILIndicator(i)=1 and one or more of the entries saved in the AirIndicator buffer=1). When the alarm is turned on in step 242, the infusion system is turned off automatically or manually by the clinician to stop the infusion of the infusion fluid.

In step 238, if any of the buffer saved in step 226 is not set to 1 (i.e. if any of AirIndicator(i) . . . AirIndicator(i–Nw) is not set to 1), the method proceeds from step 238 to step 244. In step 244, a determination is made that the air-in-line indicator AILIndicator resulted in a nuisance air-in-line determination since although the air-in-line indicator indicated that air was present no AirIndicator in the buffer indicated that air was present. The method proceeds from step 244 through location step 246 through location step 218 to step 220 and repeats the process steps.

If it is determined in step 236 that the air-in-line indicator AILIndicator(i) does not equal 1, the method proceeds from step 236 to step 248. In step 248, a determination is made whether AirIndicator(i–Nw) is set to 1 (i.e. whether the plunger force indicator Nw cycles ahead of the air-in-line detector determined that air was in the infusion system to accommodate for the delay between the plunger force sensor and the air-in-line sensor). If the determination is made in step 248 that the AirIndicator(i–Nw) is not set to 1 the method proceeds from step 248 through location step 250 through location step 218 to step 220 and repeats the process steps (since neither the air-in-line indicator AILIndicator nor the air indicator AirIndicator indicated that air was in the infusion system).

If the determination is made in step 248 that the AirIndicator(i–Nw) is set to 1 the method proceeds from step 248 to step 252. In step 252, a determination is made whether the confidence indicator ConfIndicator(i–Nw) of the force algorithm (indicating the confidence level that air has been detected in the infusion system by the plunger force sensor by applying the force algorithm Nw cycles ahead of the air-in-line sensor) is greater than or equal to the confidence threshold (Conf_Thr). If the determination is made in step 252 that the confidence indicator of the force algorithm is not greater than or equal to the confidence threshold, the method proceeds from step 252 through location step 254 through location step 218 to step 220 and repeats the process steps (since the air-in-line indicator AILIndicator did not indicate that air was in the infusion system and the air indicator AirIndicator did not confidently predict that air was in the infusion system).

If the determination is made in step 252 that the confidence indicator of the force algorithm is greater than or equal to the confidence threshold, the method proceeds from step 252 to step 256. In step 256, a determination is made that the air-in-line indicator AILIndicator wrongly determined that air was not present in the infusion system (since the air-in-line indicator AILIndicator did not indicate that air was in the infusion system but the air indicator AirIndicator confidently determined that air was in the infusion system). The method proceeds from step 256 to step 258. In step 258, the alarm is turned on indicating that air is disposed in the infusion system. When the alarm is turned on in step 258, the infusion system is turned off automatically or manually by the clinician to stop the infusion of the infusion fluid. In other embodiments, the method 212 may be altered to vary the order or substance of any of the steps, to delete one or more steps, or to add one or more steps.

Figure 7:
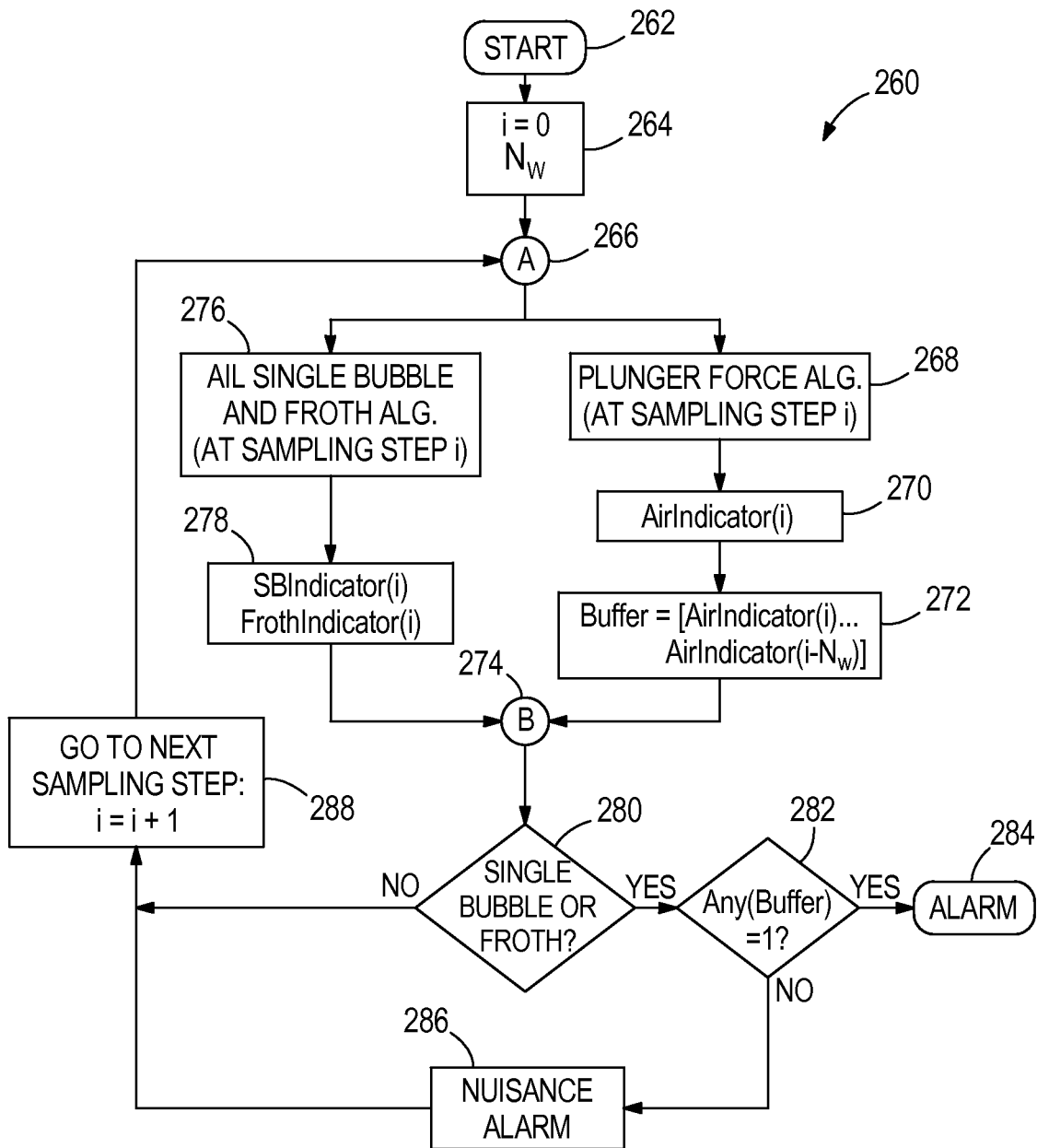
FIG. 7 illustrates a flowchart of another embodiment of a method for determining whether air is in an infusion system using both plunger force sensor readings and air-in-line sensor readings.

FIG. 7 illustrates a flowchart of another embodiment of a method 260 for determining whether air is in an infusion system using both plunger force sensor readings and air-in-line sensor readings. It can be applied to any air-in-line single bubble algorithm or froth algorithm as long as it outputs an air-in-line single bubble indicator and a froth indicator at each sampling step indicating whether a single bubble or froth was detected in the line by the air-in-line sensor. Similarly, it can be applied to any force algorithm as long as it outputs an air indicator at each sampling step indicating whether air was detected in the line by the plunger force sensor. The method 260 uses the force algorithm to declare true air alarms, or nuisance/false air-in-line single bubble or froth alarms. The method 260 takes into account delays between the air-in-line indicator and the air indicator which result from differences in locations of the air-in-line sensor and the plunger force sensor by utilizing a buffer that stores previous air indicators based on the plunger force sensor measurements. The method 260 may utilize the system of FIG. 1. In other embodiments, the method 260 may utilize varying systems.

In step 262, the method starts. The method proceeds from step 262 to step 264. In step 264, the variables are set including setting sampling step i=1 and setting the number Nw of pumping strokes of delay between a plunger force sensor and an air-in-line sensor. The method proceeds from step 264 through location step 266 to step 268. In step 268, a plunger force algorithm is used to determine at sampling step i whether air is detected in a pumping chamber based on measurements of a plunger force sensor. The method proceeds from step 268 to step 270. In step 270, if air is detected in step 268 then an air indicator AirIndicator(i) is set to 1 and if air is not detected in step 268 then the air indicator AirIndicator(i) is set to 0. The method proceeds from step 270 to step 272. In step 272, a Buffer is saved as [AirIndicator(i) . . . AirIndicator(i−Nw)] saving the 1 or 0 setting made in step 270. For instance, if it takes 2 pumping strokes of the pump for the infusion fluid to travel from the plunger force sensor to the air-in-line sensor, then Nw is set to 2 to accommodate for this delay and the Buffer saves the AirIndicator(i) for the current sample i, the AirIndicator(i−1) for the previous sample i−1, and the AirIndicator(i−2) for two samples before. The method proceeds from step 272 through location step 274 to step 280.

While the method proceeds from step 266 to step 268, the method also simultaneously proceeds from step 266 to step 276. In step 276, an air-in-line single bubble algorithm and an air-in-line froth algorithm is used to determine at sampling step i whether a single bubble or forth is detected in a fluid-delivery-line of the infusion system based on measurements from the air-in-line sensor. The method proceeds from step 276 to step 278. In step 278, if a single bubble is detected in step 276 then a single bubble indicator SBIndicator(i) is set to 1 and if the single bubble is not detected in step 276 then the SBIndicator(i) is set to 0. Similarly, in step 278, if froth is detected in step 276 then a froth indicator FrothIndicator(i) is set to 1 and if the froth is not detected in step 276 then the froth indicator FrothIndicator(i) is set to 0. The method proceeds from step 278 through location step 274 to step 280.

In step 280, a determination is made as to whether either the single bubble indicator SBIndicator(i) is set to 1 or the froth indicator FrothIndicator(i) is set to 1. If step 280 determines that either the single bubble indicator SBIndicator(i) is set to 1 or the froth indicator FrothIndicator(i) is set to 1, then the method proceeds from step 280 to step 282. In step 282, a determination is made as to whether any of the buffer saved in step 272 is set to 1 (i.e. if any of AirIndicator(i) . . . AirIndicator(i−Nw) is set to 1). If step 282 determines that any of the buffer saved in step 272 is set to 1, then the method proceeds from step 282 to step 284 and turns on the alarm indicating that air is disposed in the infusion system since the plunger force indicator (AirIndicator) indicated that air was in the infusion system and either the single bubble indicator (SBIndicator) or the froth indicator (FrothIndicator) indicated that a single bubble or froth was in the infusion system. When the alarm was turned on in step 284, the infusion system is turned off automatically or manually by the clinician to stop the infusion of the infusion fluid.

If step 282 determines that none of the buffer saved in step 272 is set to 1, then the method proceeds from step 282 to step 286. In step 286, a nuisance alarm is turned on because the plunger force indicator AirIndicator found that no air was in the infusion system but the single bubble indicator SBIndicator or the froth indicator FrothIndicator detected that a single bubble or froth was present in the infusion system. The method proceeds from step 286 to step 288. In step 288, sampling step i is incremented to i=i+1. The method proceeds from step 288 through location step 266 to steps 268 and 276 and repeats the process steps.

If step 280 determines that neither the single bubble indicator SBIndicator(i) is set to 1 nor the froth indicator FrothIndicator(i) is set to 1, then the method proceeds from step 280 to step 288. In step 288, sampling step i is incremented to i=i+1. The method proceeds from step 288 through location step 266 to steps 268 and 276 and repeats the process steps. In another embodiment, if step 280 determines that neither the single bubble indicator SBIndicator(i) is set to 1 nor the froth indicator FrothIndicator(i) is set to 1, then the method can determine whether the plunger force indicator AirIndicator found that air was in the infusion system and if it did then a missed alarm can be turned on. In other embodiments, the method 260 may be altered to vary the order or substance of any of the steps, to delete one or more steps, or to add one or more steps.

Figure 8:
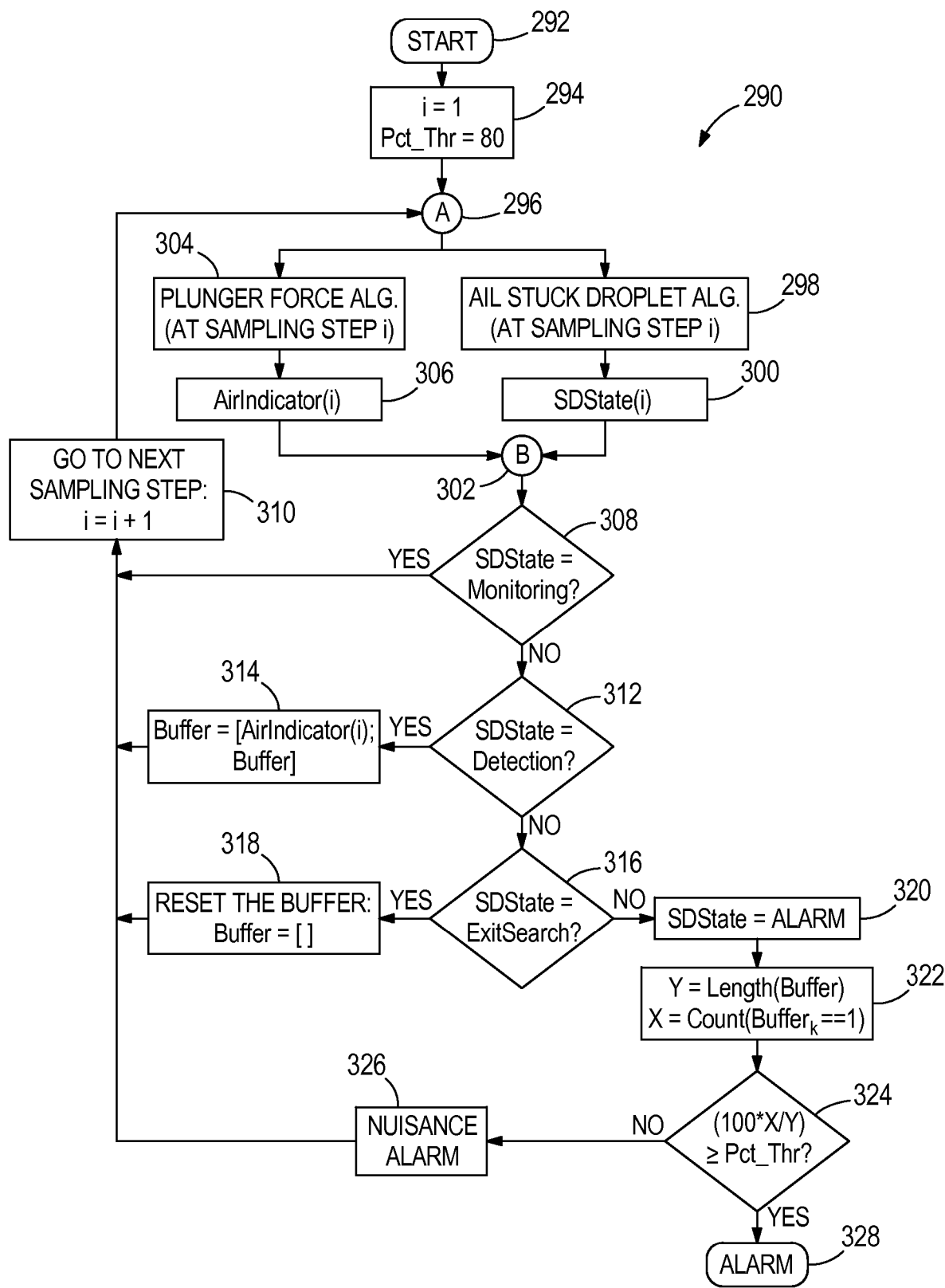
FIG. 8 illustrates a flowchart of another embodiment of a method for determining whether air is in an infusion system using both plunger force sensor readings and air-in-line sensor readings.

FIG. 8 illustrates a flowchart of another embodiment of a method 290 for determining whether air is in an infusion system using both plunger force sensor readings and air-in-line sensor readings. It can be applied to any force algorithm as long as it outputs an air indicator at each sampling step indicating whether air was detected in the line by the plunger force sensor. It can be applied to air-in-line stuck droplet algorithms which determine at each sampling step or pumping stroke whether it is in a monitoring state, a detection state, an exit state, or an alarm state. The method 290 uses the force algorithm and the various states of the air-in-line stuck droplet algorithm to declare true air alarms, or nuisance/false air alarms. The method 290 may utilize the system of FIG. 1. In other embodiments, the method 290 may utilize varying systems.

In step 292, the method starts. The method proceeds from step 292 to step 294. In step 294, the variables are set including setting sampling step i=1, and setting the percent threshold Pct_Thr=80. The method proceeds from step 294 through location step 296 to step 298. In step 298, an air-in-line stuck droplet algorithm is used to determine at sampling step i whether a stuck droplet is detected in the infusion system based on measurements of an air-in-line sensor. The method proceeds from step 298 to step 300. In step 300, the stuck droplet state at sampling step i SDState(i) is determined as being either in a monitoring state, in a detection state, in an exit search state, or in an alarm state. The method proceeds from step 300 through location step 302 to step 308.

While the method proceeds from location step 296 to step 298, the method also simultaneously proceeds from location step 296 to step 304. In step 304, a plunger force algorithm is used to determine at sampling step i whether air is detected in a pumping chamber based on measurements of a plunger force sensor. The method proceeds from step 304 to step 306. In step 306, if air is detected in step 304 then an air indicator AirIndicator(i) is set to 1 and if air is not detected in step 304 then the air indicator AirIndicator(i) is set to 0. The method proceeds from step 306 through location step 302 to step 308.

In step 308, a determination is made based on the determination of step 300 whether the stuck droplet state at sampling step i SDState(i) is in a monitoring state. In the monitoring state, the algorithm will search for a stuck droplet pattern. If in step 308 the determination is made that the stuck droplet state at sampling step i SDState(i) is in a monitoring state, then the method proceeds to step 310. In step 310, the sampling step i is set to i=i+1 in order to advance to the next sampling step in order to monitor the next sample (i.e. the next pumping stroke). The method proceeds from step 310 to location step 296 and repeats the process steps.

If in step 308 the determination is made that the stuck droplet state at sampling step i SDState(i) is not in a monitoring state then the method proceeds to step 312. In step 312, a determination is made based on the determination of step 300 whether the stuck droplet state at sampling step i SDState(i) is in a detection state. In the detection state, the algorithm detects a possible stuck droplet pattern and has to decide if it is a match or not. If in step 312 the determination is made that the stuck droplet state at sampling step i SDState(i) is in a detection state, then the method proceeds to step 314. In step 314, a Buffer is saved as [AirIndicator(i) . . . ] saving the AirIndicator(i) determination made in step 306 for the current sample i as being 1 or 0. The Buffer will continue to save all AirIndicator(i) determinations made in step 306 for all samples i until the Buffer is reset. It is noted that the values in the Buffer will later be used to determine in the alarm state whether the air-in-line algorithm decision as to whether air is in the infusion system is a nuisance or a true alarm. The method then proceeds from step 314 to step 310. In step 310, the sampling step i is set to i=i+1 in order to advance to the next sampling step in order to monitor the next sample (i.e. the next pumping stroke). The method proceeds from step 310 to location step 296 and repeats the process steps.

If in step 312 the determination is made that the stuck droplet state at sampling step i SDState(i) is not in a detection state, then the method proceeds to step 316. In step 316, a determination is made based on the determination of step 300 whether the stuck droplet state at sampling step i SDState(i) is in an exit search state. In the exit search state, the algorithm decides that the suspected stuck droplet pattern is not a match and therefore is not a stuck droplet. If in step 316 the determination is made that the stuck droplet state at sampling step i SDState(i) is in an exit search state, then the method proceeds to step 318. In step 318, the Buffer saved in 314 is reset/cleared so that all previously stored values are deleted. The method proceeds from step 318 to step 310. In step 310, the sampling step i is set to i=i+1 in order to advance to the next sampling step in order to monitor the next sample (i.e. the next pumping stroke). The method proceeds from step 310 to location step 296 and repeats the process steps.

If in step 316 the determination is made that the stuck droplet state at sampling step i SDState(i) is not in an exit search state, then the method proceeds to step 320. In step 320, a determination is made based on the determination of step 300 that the stuck droplet state at sampling step i SDState(i) is in an alarm state. The method proceeds from step 320 to step 322. In step 322, an X value is saved and a Y value is saved. The X value comprises the number of 1 values saved in the Buffer of step 314. The Y value comprises the overall number of values saved in the Buffer of step 314. For instance, if the Buffer of step 314 is saved as [1 0 0 1 0] then X=2 because there are two 1 values saved and Y=5 because there are five overall 1's and O's saved. The method proceeds from step 322 to step 324. In step 324, a determination is made as to whether 100 multiplied by X/Y is greater than or equal to the percent threshold Pct_Thr of 80 set in step 294 (whether 100*XIY is greater than or equal to Pct_Thr). If in step 324 the determination is made that 100 multiplied by X/Y is not greater than or equal to the percent threshold Pct_Thr of 80 set in step 294 then the method proceeds to step 326. For instance, if X=2 and Y=5 then 100*2/5=40 which is not greater than or equal to Pct_Thr of 80 so the method would proceed to step 326. In step 326, a nuisance alarm is turned on and the infusion is not stopped because less than the threshold number of the buffer determinations, made by the plunger force algorithm, determined that air was in the infusion system leading to the determination that the stuck droplet alarm state set in step 320 was a nuisance alarm. The method proceeds from step 326 to step 310. In step 310, the sampling step i is set to i=i+1 in order to advance to the next sampling step in order to monitor the next sample (i.e. the next pumping stroke). The method proceeds from step 310 to location step 296 and repeats the process steps.

If in step 324 the determination is made that 100 multiplied by X/Y is greater than or equal to the percent threshold Pct_Thr of 80 set in step 294 then the method proceeds to step 328. For instance, if the Buffer set in step 314 is [1 1 1 0 1] then X=4 and Y=5 and 100*4/5=80 which is greater than or equal to Pct_Tur of 80 so the method would proceed to step 328. In step 328, an alarm is turned on indicating that air is contained in the infusion system because greater than or equal to the threshold number of the buffer determinations, made by the plunger force algorithm, determined that air was in the infusion system leading to the determination that the stuck droplet alarm state set in step 320 was a true air alarm. When the alarm is turned on in step 328, the infusion system is turned off automatically or manually by the clinician to stop the infusion of the infusion fluid. In other embodiments, the method 290 may be altered to vary the order or substance of any of the steps, to delete one or more steps, or to add one or more steps.

Figure 9:
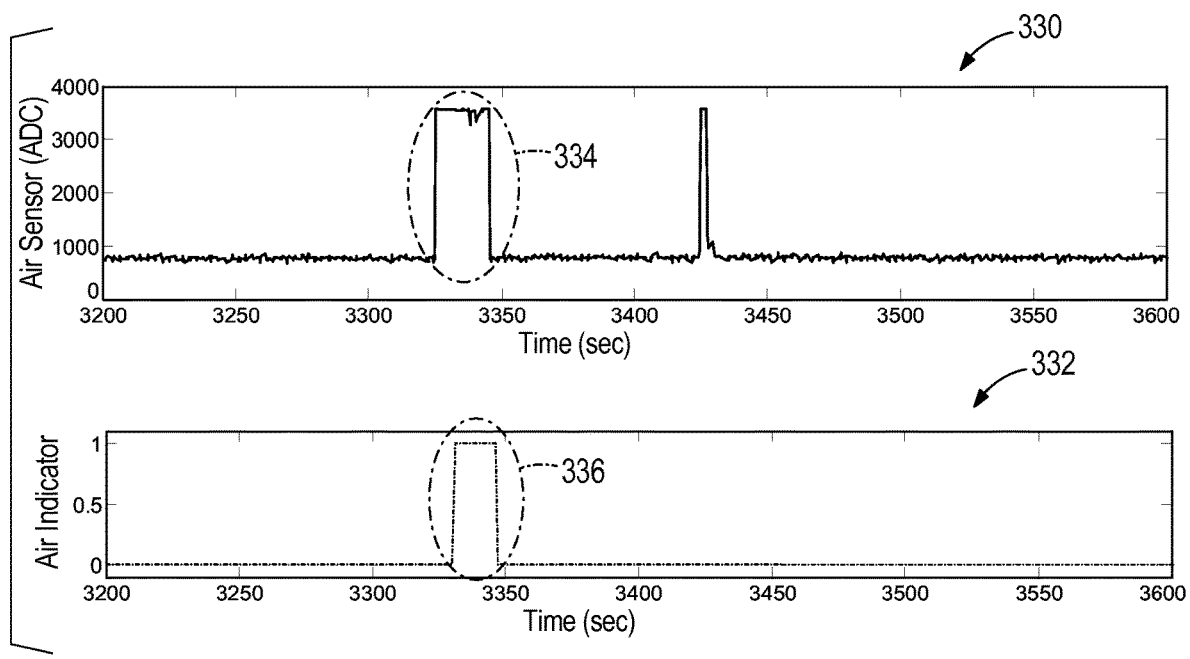
FIG. 9 illustrates two related graphs illustrating how the use of a single-sensor based algorithm for detecting the presence of air within an infusion system can lead to a false positive detection of air in the infusion system.

FIG. 9 illustrates two related graphs 330 and 332 illustrating how the use of a single-sensor based algorithm for detecting the presence of air within an infusion system can lead to a false positive detection of air in the infusion system. The graphs 330 and 332 were taken from an infusion system which did not contain a significant amount of air to warrant stopping the infusion system. The X-axis of graph 330 represents time in seconds during the infusion of infusion fluid delivered by the infusion system. The Y-axis of graph 330 represents air sensor readings of the single air-in-line sensor in analog-to-digital counts (ADC) for the infusion system during the infusion of the infusion fluid. The portion 334 of the plotted air-sensor readings shows that the air-sensor readings substantially increase and then decrease around 3,325 seconds to 3,350 seconds.

Similarly, the X-axis of graph 332 represents the corresponding time in seconds during the infusion of infusion fluid delivered by the infusion system. The Y-axis of graph 332 represents air indicator determinations made based on the air-in-line sensor readings of the corresponding graph 330. The portion 336 of the plotted air indicator readings shows that the air indicator readings substantially increase and then decrease around 3,325 seconds to 3,350 seconds based on the air-sensor readings of the corresponding graph 330. This portion 336 would result in a false positive detection of air when using a typical single-sensor based air-in-line algorithm. This false positive is caused by dancing micro bubbles of air in the infusion system. This is problematic as the infusion system would be shut down due to this false positive creating an improper delay in therapy to the patient.

Figure 10:
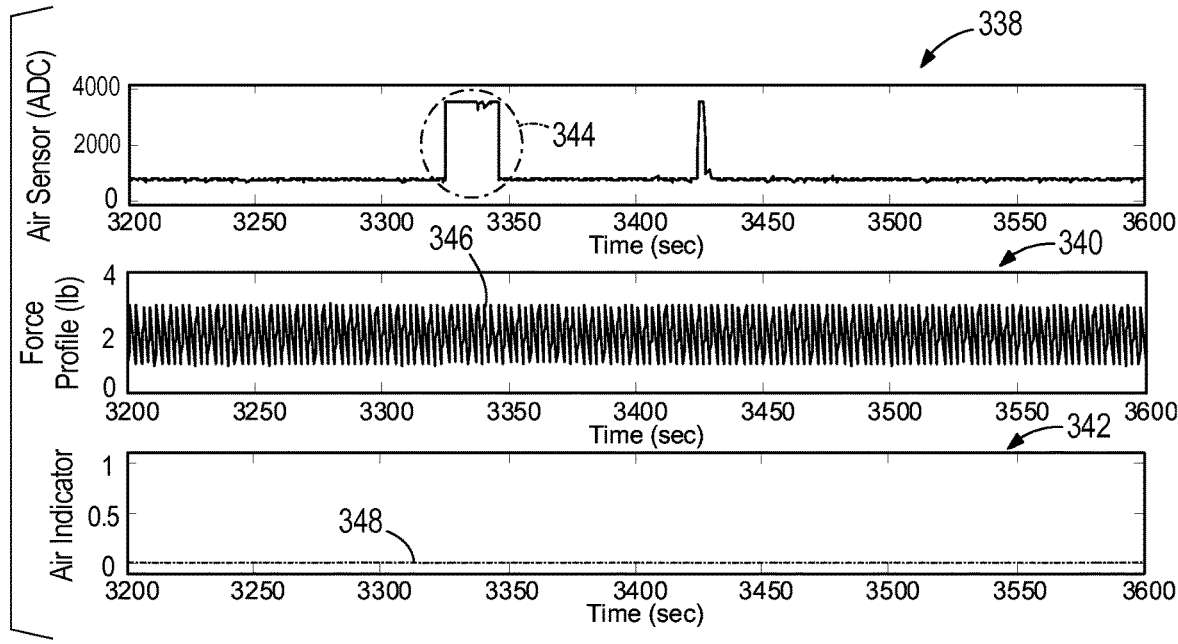
FIG. 10 illustrates three related graphs illustrating how the use of a multi-sensor based algorithm for detecting the presence of air within the infusion system tested in FIG. 9 eliminates the false positive detection of air in the in the infusion system.

FIG. 10 illustrates three related graphs 338, 340, and 342 illustrating how the use of a multi-sensor based algorithm for detecting the presence of air within the infusion system tested in FIG. 9 eliminates the false positive detection of air in the in the infusion system. The graphs 338, 340, and 342 were taken from the infusion system tested in FIG. 9 which did not contain a significant amount of air to warrant stopping the infusion system. The X-axis of graph 338 represents time in seconds during the infusion of infusion fluid delivered by the infusion system. The Y-axis of graph 338 represents air sensor readings of an air-in-line sensor in analog-to-digital counts (ADC) for the infusion system during the infusion of the infusion fluid. The portion 344 of the plotted air-sensor readings shows that the air-sensor readings substantially increase and then decrease around 3,325 seconds to 3,350 seconds.

Similarly, the X-axis of graph 340 represents the corresponding time in seconds during the infusion of infusion fluid delivered by the infusion system. The Y-axis of graph 340 represents force profile readings in pounds taken by a plunger force sensor connected to the infusion system. The plotted portion 346 of the force profile readings shows that the plot is substantially uniform during the entire time plotted from 3,200 seconds to 3,600 seconds which does not indicate that air is in the infusion system.

Similarly, the X-axis of graph 342 represents the corresponding time in seconds during the infusion of infusion fluid delivered by the infusion system. The Y-axis of graph 342 represents air indicator determinations made by integrating the air-sensor readings and the force profile readings of the corresponding graphs 338 and 340. The plotted portion 348 of the air indicator readings shows that the air indicator readings stayed at 0 during the entire time plotted from 3,200 seconds to 3,600 seconds based on the integrated air-sensor readings and force profile readings of the corresponding graphs 338 and 340. As a result, the use of multiple different types of sensors to monitor the infusion system has eliminated the false positive detection of air which occurred when the same infusion system was tested using only a single type of sensor. This improves accuracy and avoids unnecessary shut-downs of the infusion system.

Figure 11:
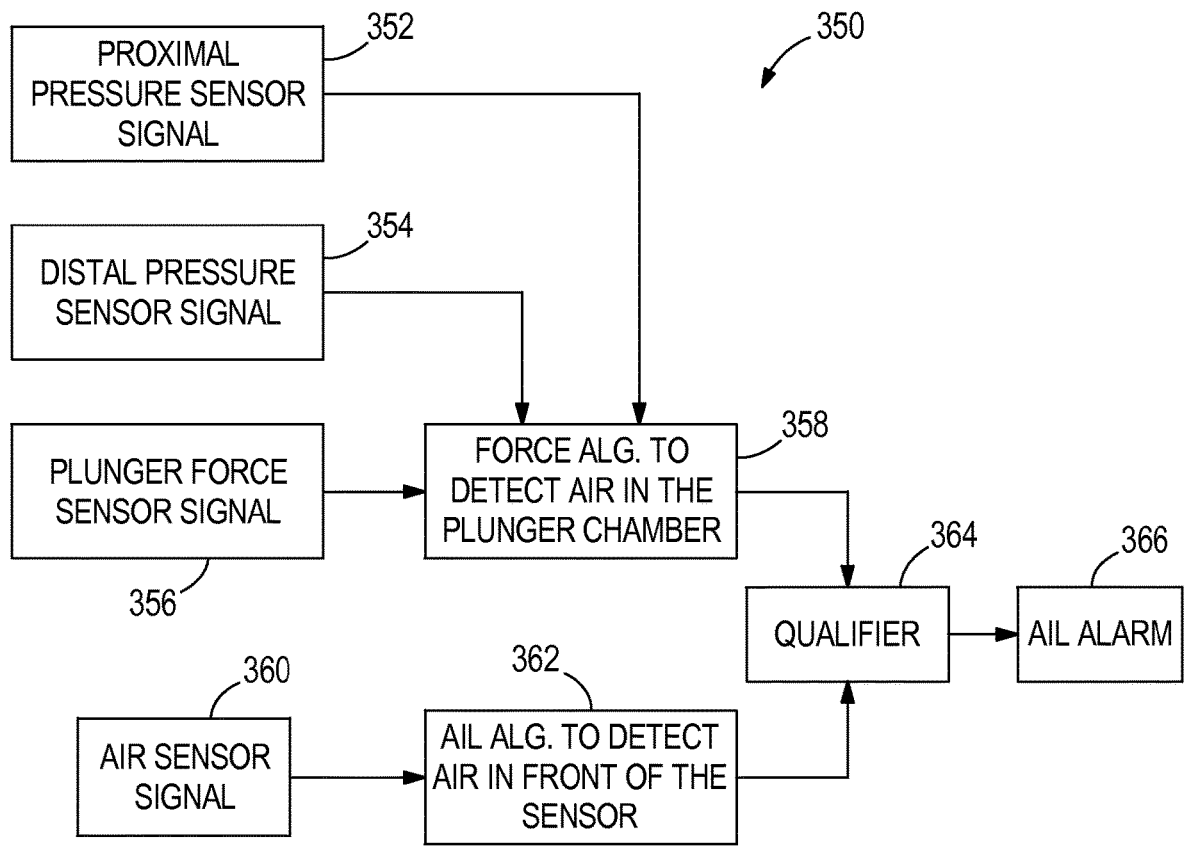
FIG. 11 illustrates a flowchart of one embodiment of a method for determining whether air is in an infusion system.

FIG. 11 illustrates a flowchart of one embodiment of a method 350 for determining whether air is in an infusion system. The method 350 may utilize the system of FIG. 1. In other embodiments, the method 350 may utilize varying systems. In step 352, a proximal pressure sensor determines the amount of pressure acting proximally on the infusion system. In step 354, a distal pressure sensor determines the amount of pressure acting distally on the infusion system. In step 356, a force sensor determines how much force is acting upon a plunger or pumping member of a pump. In step 358, a force algorithm is applied by integrating the proximal pressure measurements, the distal pressure measurements, and the force sensor measurements of steps 352, 354, and 356 in order to detect whether air is in a chamber of the pump. The force algorithm of step 358 integrates the readings of steps 352, 354, and 356 which were based on the measurements of the proximal pressure sensor, the distal pressure sensor, and the force sensor and in doing so considers the delays between the proximal force sensor, the distal pressure sensor, and the force sensor which results due to the distances between them.

In step 360, an air sensor determines how much of a signal propagates through a fluid delivery line of the infusion system. In step 362, an air-in-line algorithm is applied using the air sensor measurements of step 360 in order to detect whether air is located in the fluid delivery line at the air sensor based on the air sensor measurements. In step 364, a single qualifier algorithm is applied which uses both the results of the application of the force algorithm in step 358 and the results of the application of the air-in-line algorithm of step 362 in order to determine whether air is in the infusion system. The qualifier algorithm of step 364 integrates the decisions of steps 358 and 362 which were based on the measurements of the proximal pressure sensor, the distal pressure sensor, the force sensor, and the air sensor and in doing so considers the delays between the proximal force sensor, the distal pressure sensor, the force sensor, and the air sensor which results due to the distances between them.

In such manner, by considering the air results of different types of sensors at different locations a more accurate determination is made as to whether air is contained in the infusion system. This avoids false positives or nuisance alarms caused by a reading by one sensor at one location which is either inaccurate or caused by an issue such as bouncing air bubbles, a stuck droplet, or froth in the infusion system which otherwise would lead to an inaccurate determination as to the presence of air in the infusion system. In step 366, the alarm device turns on an alarm if step 364 determines that air is in the infusion system. In other embodiments, the method 350 may be altered to vary the order or substance of any of the steps, to delete one or more steps, or to add one or more steps.

Figure 12:
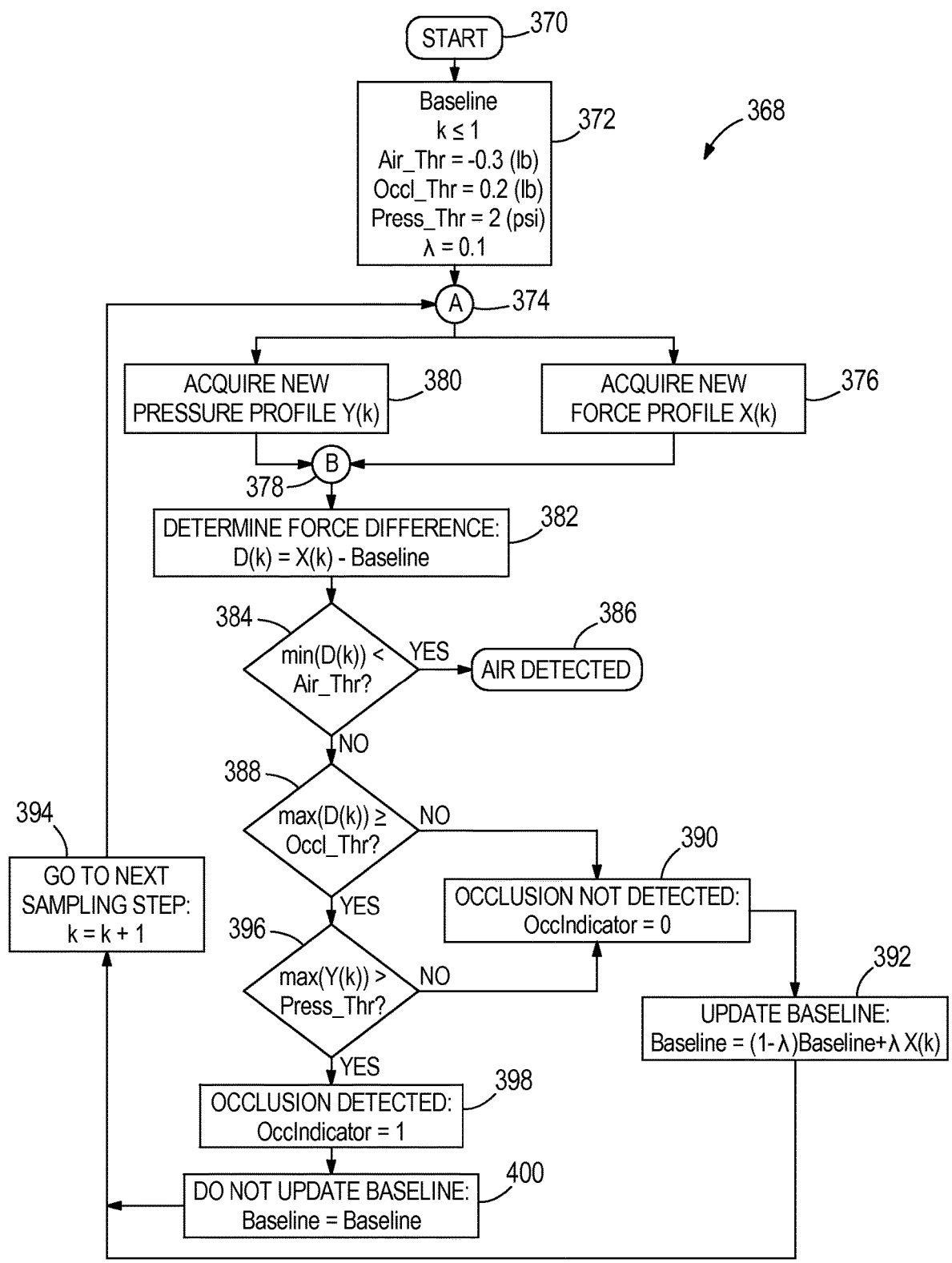
FIG. 12 illustrates a flowchart of another embodiment of a method for determining whether air is in an infusion system using plunger force sensor readings and pressure sensor readings.

FIG. 12 illustrates a flowchart of another embodiment of a method 368 for determining whether air is in an infusion system using plunger force sensor readings and pressure sensor readings. It can be applied as long as a plunger force profile and a pressure profile is taken at each sampling step. The method 368 uses the plunger force profile to determine whether there is air in the infusion system, and uses the plunger force profile and the pressure profile to determine whether or not an occlusion is present in the infusion system.

The method 368 may utilize the system of FIG. 1. In other embodiments, the method 368 may utilizing varying systems.

In step 370, the method starts. The method proceeds from step 370 to step 372. In step 372, the variables are set including setting a sampling step k=1, a baseline which is a force profile associated with fluid, setting a force threshold for air detection Air_Thr, setting a force threshold for occlusion detection Occl_Thr, setting a pressure threshold Press_Thr, and setting a forgetting factor λ. It is noted that throughout this disclosure that k represents one stroke of the pump of the infusion system. The method proceeds from step 372 through location step 374 to step 376. In step 376, a force profile X(k) is acquired for the current sample of the pumping cycle of the infusion system. It is noted that the force profile X(k) represents a plurality of force readings which are taken during each stroke k of the pump. For instance, in one embodiment six force readings may be taken at various points of each stroke k of the pump. In other embodiments, any number of force readings may be taken throughout each stroke k of the pump. The method proceeds from step 376 through location step 378 to step 382.

While the method proceeds from location step 374 to step 376, the method also simultaneously proceeds from location step 374 to step 380. In step 380, a pressure profile Y(k) is acquired for the current sample of the pumping cycle of the infusion system. It is noted that the pressure profile Y(k) represents a plurality of pressure readings which are taken during each stroke k of the pump. For instance, in one embodiment six pressure readings may be taken at various points of each stroke k of the pump. In other embodiments, any number of pressure readings may be taken throughout each stroke k of the pump. The method proceeds from step 380 through location step 378 to step 382.

In step 382, a force difference D(k) for the current sample k of the pumping cycle is determined by subtracting the baseline from the force profile X(k) for the current sample k, wherein the equation is D(k)=X(k)−baseline. The method proceeds from step 382 to step 384. In step 384, a determination is made as to whether the minimum value of the force difference min(D(k)) for the current sample k is less than the force threshold for air detection Air_Tur. If the determination is made in step 384 that the minimum value of the force difference min(D(k)) for the current sample k is less than the force threshold for air detection Air_Tur then the method proceeds to step 386. This drop in the force profile indicates a transition from fluid to air since air is more compressible than fluid resulting in less force. In step 386, a determination is made that air has been detected and a qualifier algorithm may be applied to determine whether to stop the infusion.

If the determination is made in step 384 that the minimum value of the force difference min(D(k)) for the current sample k is not less than the force threshold for air detection Air_Thr then the method proceeds to step 388. In step 388, a determination is made whether the maximum value of the force difference max(D(k)) for the current sample k is greater than or equal to the force threshold for occlusion detection Occl_Thr. If the determination is made in step 388 that the maximum value of the force difference max(D(k)) for the current sample k is not greater than or equal to the force threshold for occlusion detection Occl_Thr then the method proceeds to step 390. It is noted that during an occlusion the plunger force readings are higher than in non-occlusion conditions. In step 390, a determination is made that an occlusion has not been detected and the occlusion indicator OccIndicator is set to 0 because air was not detected and a significant increase in the force difference was not detected. The method proceeds from step 390 to step 392. In step 392, the baseline is updated using the equation baseline=((1−forgetting factor λ)*baseline)+(forgetting factor λ*force profile X(k)). It is noted that unless an occlusion is detected, the method updates the baseline to account for the variability seen in the force-profiles due to medication type, tubing type, PMC, ambient temperature, or other factors. The method proceeds from step 392 to step 394. In step 394, the sampling step k is increased using the equation k=k+1. The method proceeds from step 394 to location step 374 and repeats the process steps.

If the determination is made in step 388 that the maximum value of the force difference max(D(k)) for the current sample k is greater than or equal to the force threshold for occlusion detection Occl_Thr then the method proceeds to step 396. In step 396, a determination is made as to whether the maximum value of the pressure profile max(Y(k)) for the current sample k is greater than the pressure threshold Press_Thr. If the determination is made in step 396 that the maximum value of the pressure profile max(Y(k)) for the current sample k is not greater than the pressure threshold Press_Thr then the method proceeds to step 390. In step 390, a determination is made that an occlusion has not been detected and the occlusion indicator OccIndicator is set to 0 because air was not detected, and although a significant increase in the force difference was detected a significant increase in the pressure profile was not detected. The method proceeds from step 390 to step 392. In step 392, the baseline is updated using the equation baseline=((1−forgetting factor λ)*baseline)+(forgetting factor λ*force profile X(k)). It is noted that unless an occlusion is detected, the method updates the baseline to account for the variability seen in the force-profiles due to medication type, tubing type, PMC, ambient temperature, or other factors. The method proceeds from step 392 to step 394. In step 394, the sampling step k is increased using the equation k=k+1. The method proceeds from step 394 to location step 374 and repeats the process steps.

If the determination is made in step 396 that the maximum value of the pressure profile max(Y(k)) for the current sample k is greater than the pressure threshold Press_Thr then the method proceeds to step 398. In step 398, a determination is made that an occlusion has been detected and the occlusion indicator OccIndicator is set to 1 because air was not detected, a significant increase in the force profile was detected, and a significant increase in the pressure profile was detected. The method proceeds from step 398 to step 400. In step 400, the baseline is not updated so that the baseline=baseline. The baseline is not updated to eliminate/discard the changes in the force measurement which may be caused by the applied pressure/occlusion in order to eliminate false air-detections. The method proceeds from step 400 to step 394. In step 394, the sampling step k is increased using the equation k=k+1. The method proceeds from step 394 to location step 374 and repeats the process steps. In other embodiments, the method 368 of FIG. 12 may be altered to vary the order or substance of any of the steps, to delete one or more steps, or to add one or more steps.

Figure 13:
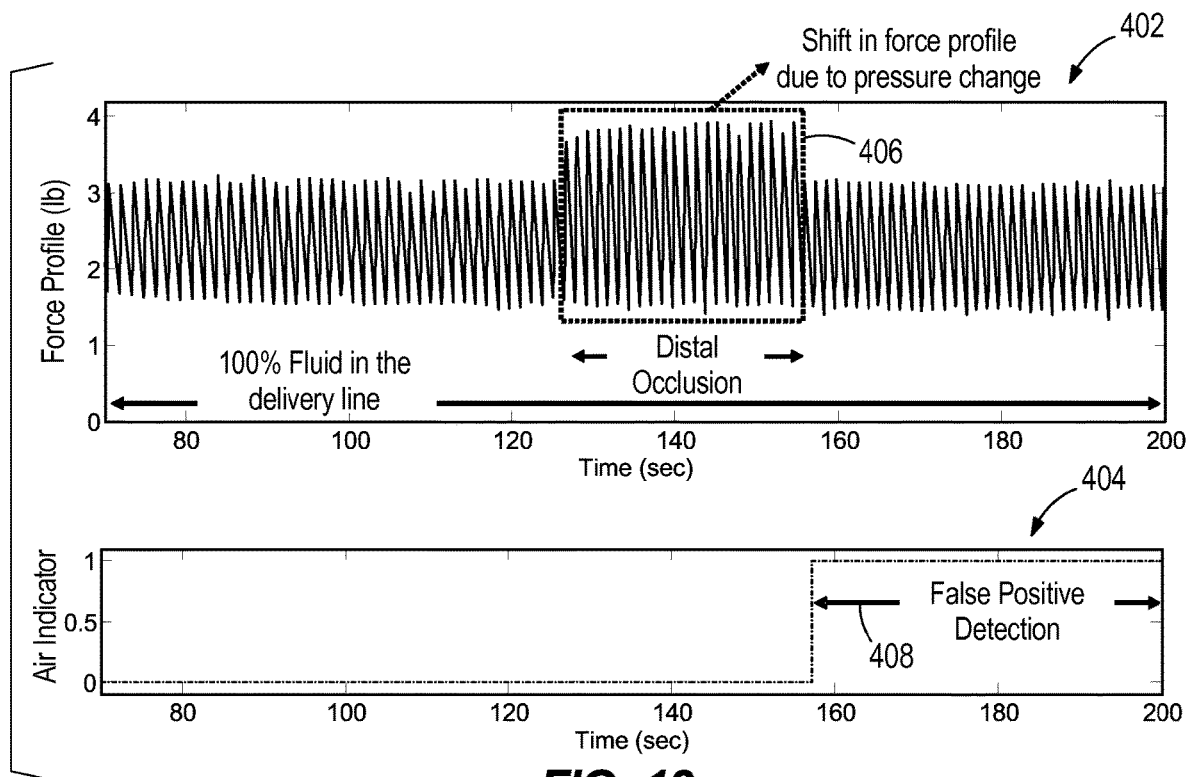
FIG. 13 illustrates two related graphs illustrating how the use of a single-sensor based algorithm for detecting the presence of air within an infusion system can lead to a false positive detection of air in the infusion system.

FIG. 13 illustrates two related graphs 402 and 404 illustrating how the use of a single-sensor based algorithm for detecting the presence of air within an infusion system can lead to a false positive detection of air in the infusion system. The graphs 402 and 404 were taken from an infusion system which did not contain a significant amount of air to warrant stopping the infusion system but rather underwent a temporary distal occlusion during a portion of the testing. The X-axis of graph 402 represents time in seconds during the infusion of infusion fluid delivered by the infusion system. The Y-axis of graph 402 represents force sensor readings of the single force sensor in pounds for the infusion system during the infusion of the infusion fluid. The portion 406 of the plotted force profile readings shows that the force profile readings substantially increase and then decrease around 125 seconds to 155 seconds when the distal occlusion occurred.

Similarly, the X-axis of graph 404 represents the corresponding time in seconds during the infusion of infusion fluid delivered by the infusion system. The Y-axis of graph 404 represents air indicator determinations made based on the force profile sensor readings of the corresponding graph 402. The portion 408 of the plotted air indicator readings shows that the air indicator readings substantially increase around 155 seconds based on the force profile sensor readings of the corresponding graph 402 which were due to the temporary distal occlusion. This portion 404 would result in a false positive detection of air when using a typical single-sensor based force-profile algorithm. This false positive is caused by the temporary occlusion. This is problematic as the infusion system would be shut down due to this false positive creating an improper delay in therapy to the patient.

Figure 14:
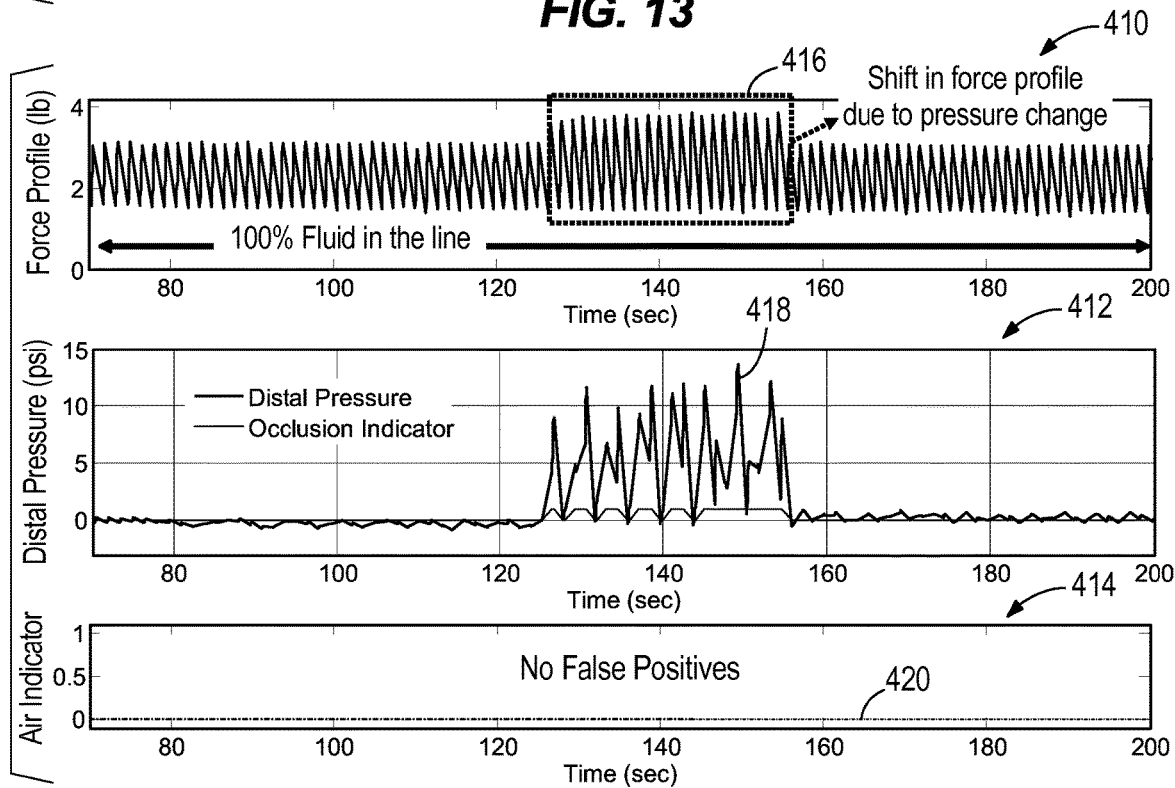
FIG. 14 illustrates three related graphs illustrating how the use of a multi-sensor based algorithm for detecting the presence of air within the infusion system tested in FIG. 13 eliminates the false positive detection of air in the in the infusion system.

FIG. 14 illustrates three related graphs 410, 412, and 414 illustrating how the use of a multi-sensor based algorithm for detecting the presence of air within the infusion system tested in FIG. 13 eliminates the false positive detection of air in the in the infusion system. The graphs 410, 412, and 414 were taken from the infusion system tested in FIG. 13 which did not contain a significant amount of air to warrant stopping the infusion system but which underwent a temporary occlusion during a portion of the testing. The X-axis of graph 410 represents time in seconds during the infusion of infusion fluid delivered by the infusion system. The Y-axis of graph 410 represents force profile sensor readings in pounds for the infusion system during the infusion of the infusion fluid. The portion 416 of the plotted force profile sensor readings shows that the force-sensor readings substantially increase and then decrease around 125 seconds to 155 seconds due to the temporary occlusion.

Similarly, the X-axis of graph 412 represents the corresponding time in seconds during the infusion of infusion fluid delivered by the infusion system. The Y-axis of graph 412 represents distal pressure readings in psi taken by a distal pressure sensor connected to the infusion system. The plotted portion 418 of the distal pressure readings shows that the distal pressure substantially increases and then decreases around 125 seconds to 155 seconds which indicates that an occlusion was present and then dissolved and may have been the reason that the force profile of graph 410 increased from the period of around 125 seconds to 155 seconds. The decrease of the force profile of graph 410 around 155 seconds may have been due to the release of the occlusion rather than air being in the infusion system.

Similarly, the X-axis of graph 414 represents the corresponding time in seconds during the infusion of infusion fluid delivered by the infusion system. The Y-axis of graph 414 represents air indicator determinations made by integrating the force profile readings and the distal pressure readings of the corresponding graphs 410, and 412. The plotted portion 420 of the air indicator readings shows that the air indicator readings stayed at 0 during the entire time plotted from 0 seconds to 200 seconds based on the integrated force profile readings and the distal pressure readings of the corresponding graphs 410 and 412. As a result, the use of multiple different types of sensors to monitor the infusion system has eliminated the false positive detection of air which occurred when the same infusion system was tested using only a single type of sensor when a temporary occlusion was present. This improves accuracy and avoids unnecessary shut-downs of the infusion system.

Figure 15:
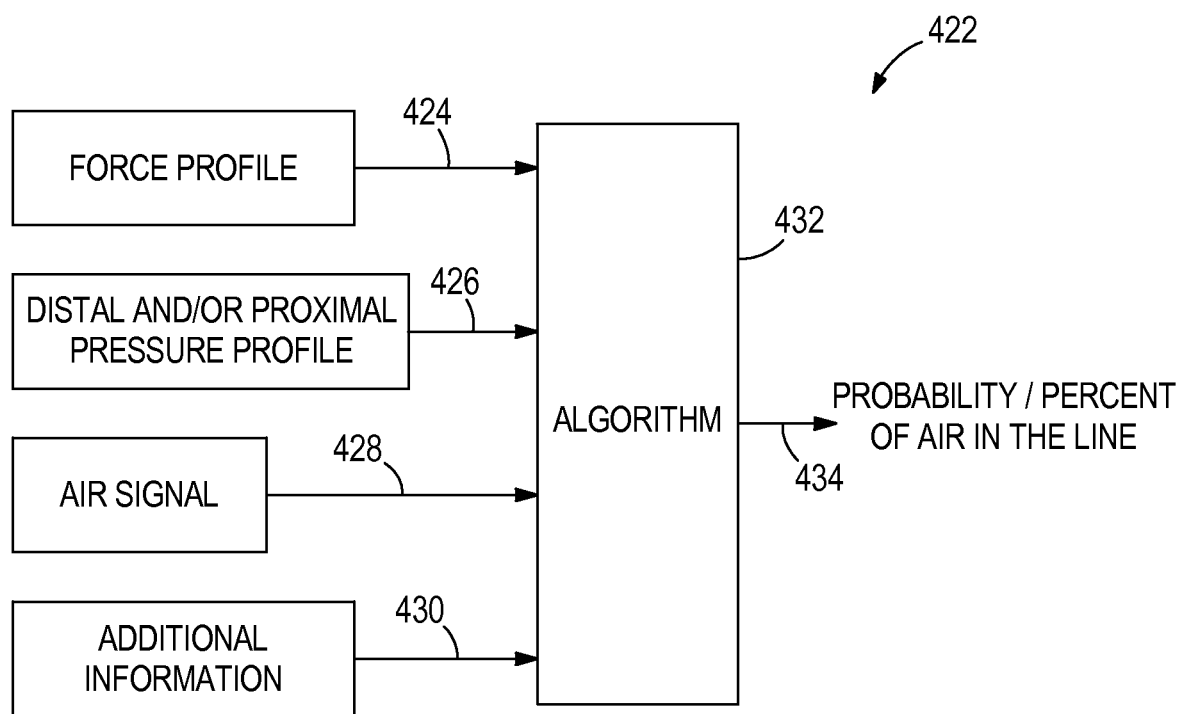
FIG. 15 illustrates a flowchart of an embodiment of a method for determining a probability of air being in an infusion system.

FIG. 15 illustrates a flowchart of an embodiment of a method 422 for determining a probability of air being in an infusion system. The method 422 may utilize the system of FIG. 1. In other embodiments, the method 422 may utilize varying systems. In step 424, a force sensor determines how much force is acting upon a plunger or pumping member of a pump of the infusion system. In step 426, a distal pressure sensor and/or a proximal pressure sensor determines the distal pressure and/or the proximal pressure acting upon the infusion system. In step 428, an air-in-line sensor determines how much of a signal propagates through a fluid-delivery line of the infusion system. In step 430, additional information is determined. The additional information may comprise medication information regarding the infusion fluid. The medication information may comprise a formulation of the infusion fluid, a rate of the infusion fluid, a duration of the infusion fluid, a viscosity of the infusion fluid, a therapy type of the infusion fluid, or a property of the infusion fluid. The additional information may comprise infusion information regarding the infusion of the infusion fluid. The infusion information may comprise a volume of the infusion fluid in the infusion container or another parameter regarding the infusion. In step 432, the measurements and information from steps 424, 426, 428, and 430 are used in an algorithm to integrate the measurements and information. In step 434, a determination is made as to the probability/percent chance of air being disposed in the fluid delivery line of the infusion system based on the results of the algorithm applied in step 432. In other embodiments, the method 422 of FIG. 15 may be altered to vary the order or substance of any of the steps, to delete one or more steps, or to add one or more steps.

Figure 16:
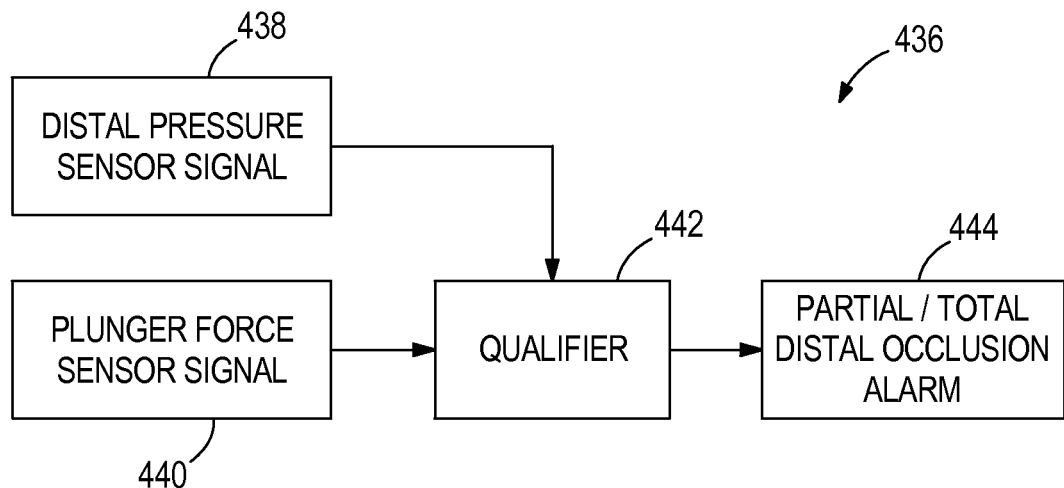
FIG. 16 illustrates a flowchart of an embodiment of a method for determining whether a partial or total distal occlusion is present in an infusion system.

FIG. 16 illustrates a flowchart of an embodiment of a method 436 for determining whether a partial or total distal occlusion is present in an infusion system. The method 436 may utilize the system of FIG. 1. In other embodiments, the method 436 may utilize varying systems. In step 438, a distal pressure sensor determines the amount of distal pressure acting on the infusion system. In step 440, a plunger force sensor determines how much force is acting upon a plunger or pumping member of a pump of the infusion system. In step 442, a qualifier integrates the results of steps 438 and 440 using one or more algorithms. In step 444, a determination is made as to whether there is a partial or total distal occlusion in the infusion system based on the qualifier used in step 442 and if there is an alarm is turned on allowing the infusion system to be turned off. The use of the results of multiple different types of sensors in one or more algorithms improves the robustness and false positive performance of the occlusion detection system. In other embodiments, the method 436 of FIG. 16 may be altered to vary the order or substance of any of the steps, to delete one or more steps, or to add one or more steps.

Figure 17:
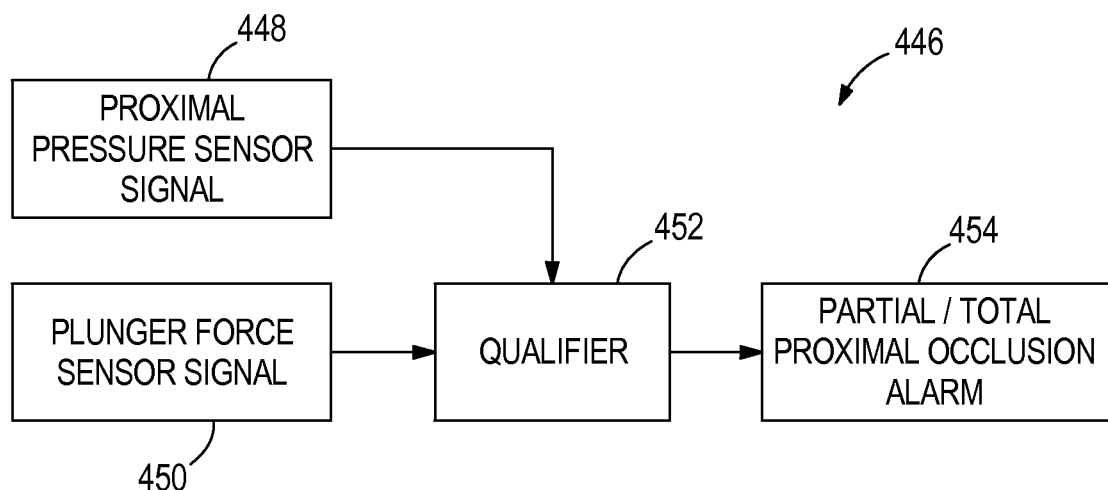
FIG. 17 illustrates a flowchart of another embodiment of a method for determining whether a partial or total proximal occlusion is present in an infusion system.

FIG. 17 illustrates a flowchart of another embodiment of a method 446 for determining whether a partial or total proximal occlusion is present in an infusion system. The method 446 may utilize the system of FIG. 1. In other embodiments, the method 446 may utilize varying systems. In step 448, a proximal pressure sensor determines the amount of proximal pressure acting on the infusion system. In step 450, a plunger force sensor determines how much force is acting upon a plunger or pumping member of a pump of the infusion system. In step 452, a qualifier integrates the results of steps 448 and 450 using one or more algorithms. In step 454, a determination is made as to whether there is a partial or total proximal occlusion in the infusion system based on the qualifier used in step 452 and if there is an alarm is turned on allowing the infusion system to be turned off. The use of the results of multiple different types of sensors in one or more algorithms improves the robustness and false positive performance of the occlusion detection system. In other embodiments, the method 446 of FIG. 17 may be altered to vary the order or substance of any of the steps, to delete one or more steps, or to add one or more steps.

Figure 18:
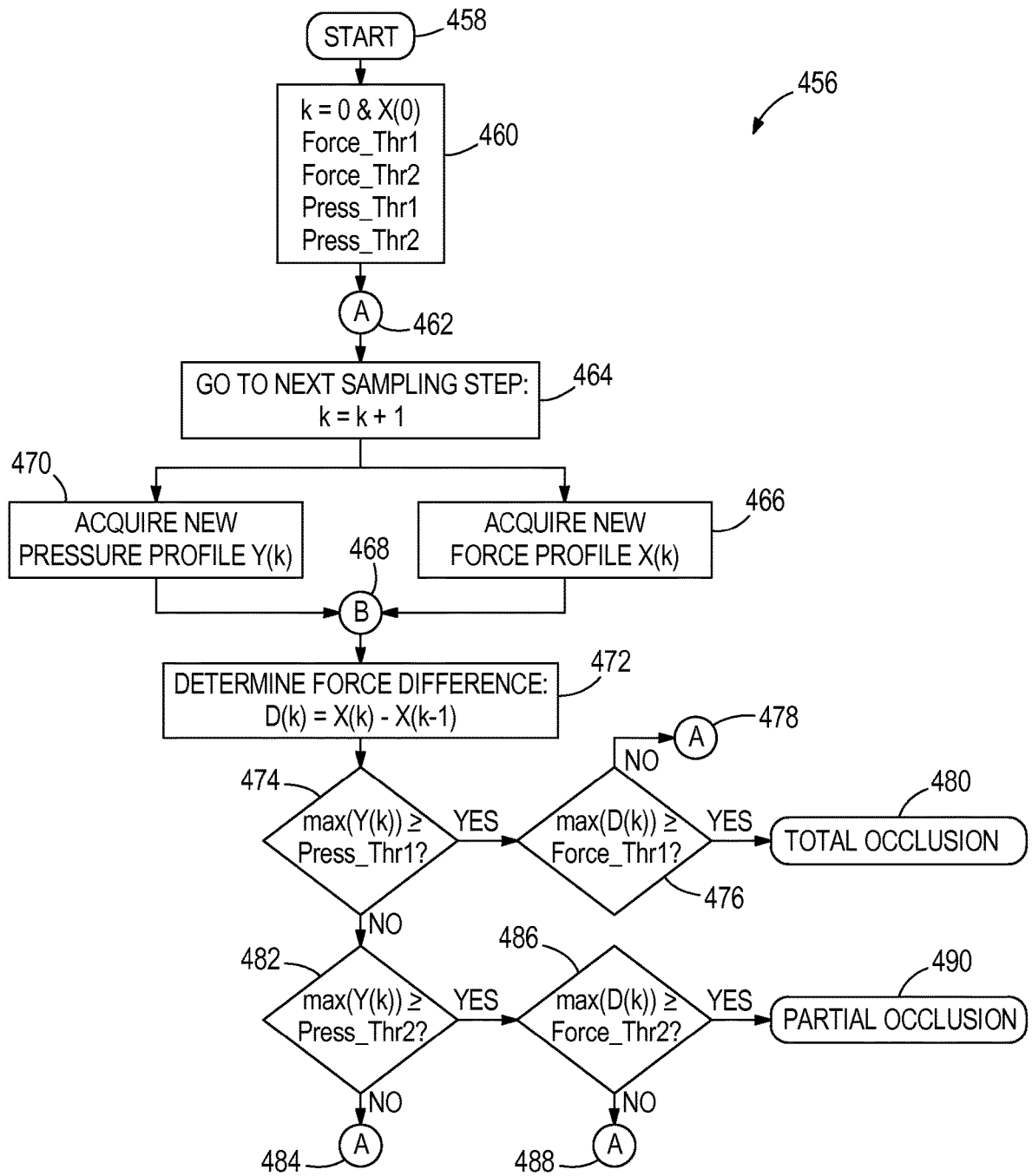
FIG. 18 illustrates a flowchart of another embodiment of a method of detecting a partial or total occlusion in an infusion system.

FIG. 18 illustrates a flowchart of another embodiment of a method 456 of detecting a partial or total occlusion in an infusion system. It can be applied as long as a plunger force profile and a pressure profile is taken at each sampling step. The method 456 uses the plunger force profile and the pressure profile to determine whether or not a partial or total occlusion is present in the infusion system. The method 456 may utilize the system of FIG. 1. In other embodiments, the method 456 may utilizing varying systems.

In step 458, the method starts. The method proceeds from step 458 to step 460. In step 460, the variables are set including sampling step k=0, setting the initial force profile associated with fluid X(O), setting the force threshold for total occlusion Force_Thr1, setting the force threshold for partial occlusion Force_Thr2, setting the pressure threshold for total occlusion Press_Thr1, and setting the pressure threshold for partial occlusion Press_Thr2. It is noted that the force threshold for total occlusion Force_Thr1 is greater than the force threshold for partial occlusion Force_Thr2. It is further noted that the pressure threshold for total occlusion Press_Thr1 is greater than the pressure threshold for partial occlusion Press_Thr2. The method proceeds from step 460 through location step 462 to step 464. In step 464, the sampling step k is set to k=k+1. The method proceeds from step 464 to step 466. In step 466, a force sensor is used to determine a force profile X(k) at sampling step k based on measurements of the force sensor. It is noted that the force profile X(k) represents a plurality of force readings which are taken during each stroke k of the pump. For instance, in one embodiment six force readings may be taken at various points of each stroke k of the pump. In other embodiments, any number of force readings may be taken throughout each stroke k of the pump. The method proceeds from step 466 through location step 468 to step 472.

While the method proceeds from step 464 to step 466, the method also simultaneously proceeds from step 464 to step 470. In step 470, a pressure sensor is used to determine a pressure profile Y(k) at sampling step k based on measurements of the pressure sensor. It is noted that the pressure profile Y(k) represents a plurality of pressure readings which are taken during each stroke k of the pump. For instance, in one embodiment six pressure readings may be taken at various points of each stroke k of the pump. In other embodiments, any number of pressure readings may be taken throughout each stroke k of the pump. The method proceeds from step 470 through location step 468 to step 472. In step 472, a force difference D(k) at sampling step k is determined by using the equation force profile X(k)–force profile X(k–1) (i.e. subtracting the force profile for the previous sampling step X(k–1) from the current sampling step force profile X(k)). The method proceeds from step 472 to step 474. In step 474, a determination is made as to whether the maximum pressure profile max(Y(k)) for the current sample k is greater than or equal to the pressure threshold for total occlusion Press_Thr1. If in step 474 a determination is made that the maximum pressure profile max(Y(K)) for the current sample k is greater than or equal to the pressure threshold for total occlusion Press_Thr1 then the method proceeds to step 476. In step 476, a determination is made as to whether the maximum force difference max(D(k)) for the current sample k is greater than or equal to the force threshold for total occlusion Force_Thr1. If step 476 determines that the maximum force difference max(D(k)) for the current sample k is not greater than or equal to the force threshold for total occlusion Force_Thr1 then the method proceeds through location step 478 through location step 462 to step 464 and repeats the process steps.

If step 476 determines that the maximum force difference max(D(k)) for the current sample k is greater than or equal to the force threshold for total occlusion Force_Thr1 then the method proceeds to step 480 and determines that there is a total occlusion. At this point, an alarm may be turned on and/or the infusion system may be turned off.

If in step 474 a determination is made that the maximum pressure profile max(Y(K)) for the current sample k is not greater than or equal to the pressure threshold for total occlusion Press_Thr1 then the method proceeds to step 482. In step 482, a determination is made as to whether the maximum pressure profile max(Y(k)) for the current sample k is greater than or equal to the pressure threshold for partial occlusion Press_Thr2. If step 482 determines that the maximum pressure profile max(Y(k)) for the current sample k is not greater than or equal to the pressure threshold for partial occlusion Press_Thr2 then the method proceeds from step 482 through location step 484 though location step 462 to step 464 and repeats the process steps.

If step 482 determines that the maximum pressure profile max(Y(k)) for the current sample k is greater than or equal to the pressure threshold for partial occlusion Press_Thr2 then the method proceeds from step 482 to step 486. In step 486, a determination is made as to whether the maximum force difference max(D(k)) for the current sample k is greater than or equal to the force threshold for partial occlusion Force_Thr2. If step 486 determines that the maximum force difference max(D(k)) for the current sample k is not greater than or equal to the force threshold for partial occlusion Force_Thr2 then the method proceeds through location step 488 through location step 462 to step 464 and repeats the process steps.

If step 486 determines that the maximum force difference max(D(k)) for the current sample k is greater than or equal to the force threshold for partial occlusion Force_Thr2 then the method proceeds to step 490 and determines that there is a partial occlusion. At this point an alarm may be generated or turned on and/or the infusion system may be turned off. In other embodiments, the method 456 of FIG. 18 may be altered to vary the order or substance of any of the steps, to delete one or more steps, or to add one or more steps.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. Furthermore, it is to be understood that the disclosure is defined by the appended claims. Accordingly, the disclosure is not to be restricted except in light of the appended claims and their equivalents.

The invention claimed is:

1. A method for infusing an infusion fluid comprising:
pumping infusion fluid through a fluid delivery line of an infusion system;
taking measurements with a plurality of different types of sensors connected to the infusion system; and
determining, with at least one processor, based on an application of a first algorithm on the measurements taken by a first sensor there is air in the fluid delivery line with a confidence above a high confidence threshold;
determining, with the at least one processor, based on an application of a second algorithm the measurements taken by a second sensor that there is no air in the fluid delivery line; and
adjusting a sensitivity parameter of the second algorithm based on an inconsistency in the determinations of air in the fluid delivery between the first sensor and the second sensor.

2. The method of claim 1 wherein the plurality of different types of sensors comprise at least two different types of sensors from a group comprising a pressure sensor, a force sensor, and an air sensor.

3. The method of claim 1 wherein the determining with the at least one processor, based on the measurements taken by the plurality of the different types of the sensors, comprises determining whether there is the partial occlusion or the total occlusion in the fluid delivery line.

4. The method of claim 1 wherein the determining with the at least one processor, based on the measurements taken by the plurality of the different types of the sensors, comprises determining the percentage of the air present in the fluid delivery line or the probability of the air being in the fluid delivery line.

5. The method of claim 4 wherein the determining the percentage of the air present in the fluid delivery line or the probability of the air being in the fluid delivery line is based additionally on medication information regarding the infusion fluid or on infusion information regarding the infusion of the infusion fluid.

6. The method of claim 5 wherein the determining the percentage of the air present in the fluid delivery line or the probability of the air being in the fluid delivery line is based on the medication information comprising a formulation of the infusion fluid, a rate of the infusion fluid, a duration of the infusion fluid, a viscosity of the infusion fluid, a therapy of the infusion fluid, or a property of the infusion fluid.

7. The method of claim 5 wherein the determining whether the percentage of the air present in the fluid delivery line or the probability of the air being in the fluid delivery line is based on the infusion information comprising a volume of the infusion fluid in an infusion container or another parameter regarding the infusion.

8. The method of claim 1 further comprising compensating, with the at least one processor, for at least one distance between the plurality of the different types of sensors by using or comparing the measurements taken by the plurality of the different types of sensors at different portions of cycles of the pumping to accommodate for one or more delays in the measurements.

* * * * *